United States Patent [19]
DeMartino et al.

[11] Patent Number: 5,847,076
[45] Date of Patent: Dec. 8, 1998

[54] REGULATORS OF THE PROTEASOME

[75] Inventors: George N. DeMartino; Clive A. Slaughter; Patricia J. Willy; Ma Chu-Ping, all of Dallas, Tex.

[73] Assignee: Board of Regents, The University of Texas System, Austin, Tex.

[21] Appl. No.: 64,694

[22] Filed: May 20, 1993

[51] Int. Cl.$^6$ .................. C07K 14/435; C07K 14/47; C12N 15/12
[52] U.S. Cl. ............... 530/350; 514/12; 536/23.5
[58] Field of Search ............... 530/350; 514/12; 536/23.5

[56] References Cited

FOREIGN PATENT DOCUMENTS

WO 92/20804  11/1992  WIPO ............... C12N 15/57

OTHER PUBLICATIONS

J.M. Fagan et al. FASEB J. 6(5) A1968 (Feb. 1992).
W. Dubiel et al. "Purification of an 11 S Regulator of the Multicatalytic Protease" J. Biol. Chem. 267(31) 22369–22377 (Nov. 1992).
L. Hoffman et al. "Multiple Forms of the 20 S Multicatalytic and the 26 S Ubiquitin/HTP–dependent Protease from Rabbit Reticulocytes" J. Biol Chem. 267(31) 22362–22368 (Nov. 1992).
Driscoll et al., "An ATP–Stabilized Inhibitor of the Proteasome Is a Component of the 1500–kDa Ubiquitin Conjugate–Degrading Complex," *Proc. Natl. Acad. Sci. USA*, 89:4986–4990, 1992, published in USA.
Goldberg et al., "Hormonal Regulation of Protein Degradation and Synthesis in Skeletal Muscle," *Federation Proc.*, 39(1):31–36, 1980, published in USA.
Lin et al., "Isolation and Characterization of a Novel Endogenous Inhibitor of the Proteasome," *Biochemistry*, 30:9709–9715, 1991, published in USA.
Li, Xiaochong S. and Etlinger, Joseph D., "Ubiquitinated Proteasome Inhibitor Is a Component of the 26 S Proteasome Complex," *Biochemistry*, 31(48):11963–11967, published in USA.
Chu–Ping et al., "Purification and Characterization of a Protein Inhibitor of the 20S Proteasome (Macropain)," *Biochim. Biophys. Acta*, 1119:303–311, 1992, published in Europe.
Chu–Ping et al., "Identification, Purification, and Characterization of a Protein Activator (PA28) of the 20 S Proteasome (Macropain)," *J. Biol. Chem.*, 267(15):10515–10523, 1992, published in USA.
Vinitsky et al., "Inhibition of the Chymotrypsin–Like Activity of the Pituitary Multicatalytic Proteinase Complex," *Biochemstry*, 31:9421–9428, 1992, published in USA.
Yukawa et al., "Proteasome and Its Novel Endogeneous Activator in Human Platelets," *Biochem. Biophys. Res. Commun.*, 178(1):256–262, 1991, published in USA.
Dialog Search Report dated Apr. 16, 1993, printed in USA.
DeMartino, et al., "PA700, an ATP–dependent Activator of the 20 S Proteasome, Is an ATPase Containing Multiple Members of a Nucleotide–binding Protein Family," *J. Biol. Chem.*, 269(33):20878–20884 (1994).
Gray, et al., "PA28 Activator Protein Forms Regulatory Caps on Proteasome Stacked Rings," *J. Mol. Biol.*, 236:7–15 (1994).
Mott, et al., "PA28, an Activator of the 20 S Proteasome, Is Composed of Two Nonidentical But Homologous Subunits," *J. Biol. Chem.*, 269(0):1–6 (1994).

*Primary Examiner*—Robert A. Wax
*Assistant Examiner*—Rebecca Prouty
*Attorney, Agent, or Firm*—Arnold, White & Durkee

[57] ABSTRACT

Regulators of the activation of the 20S proteasome for hydrolysis of peptide and protein substrates. Proteasome activating factors PA28 and PA700 are described and a carboxy-terminal fragment of a protein activator PA28 is described that is an effective inhibitor of the activation of the proteasome. The carboxy-terminal fragment binds to the proteasome and prevents the binding of PA28 and PA700 thereby preventing activation of the proteasome. Methods of treatment for muscle wasting are described wherein compositions of the present invention are administered to prevent unwanted protein degradation. Conversely, compositions of the present invention may be used to activate protein breakdown in situations where unwanted proteins accumulate in, for example, aging and Alzheimer's Disease.

8 Claims, 42 Drawing Sheets

$Mr \times 10^{-3}$

```
  10              20              30              40              50              60              70
GGAATTCCGACATCCCAGTGCCTGATCCCAGTCCAAGTCAAGGAGAAAGGAGAAGAGAAGGAGCGGAGGAAACAGCAGGAGA
  N  S  D  I  P  V  P  D  P  V  K  E  K  E  K  E  E  R  R  K  Q  Q  E 80              90             100             110             120             130             140
AGGAAGACAAGGATGAAAGAAAAGAAGAGAAAGGGGAAGATGAAGACAAAGGTCCTCCATGTGGCCCAGTGAGCTGCA
  K  E  D  K  D  E  K  K  K  G  E  D  E  D  K  G  P  P  C  G  P  V  S  C 150             160             170             180             190             200             210
ATGAGAAGATTGTGGTCCTCCTGCAGCGGGTAAAGCCTGAGATCAAGGATGTCATTGAGAAGCTCAACCTGG
  N  E  K  I  V  V  L  L  Q  R  V  K  P  E  I  K  D  V  I  E  K  L  N  L 220             230             240             250             260             270             280
TCACCACCTGGCTGCAGCTGCAAATACCCTCGGATTGAGGATGGGAATAATTTTGGAGTGGCTGTCCAGGAGA
  V  T  T  W  L  Q  L  Q  I  P  R  I  E  D  G  N  N  F  G  V  A  V  Q  E 290             300             310             320             330             340             350             360
AGGTGTTTGAGCTGATGACTGCTCTTCACACTAAGCTGGAAGGCTTCCACACTCAAATTTCCAAGTATTTCT
  K  V  F  E  L  M  T  A  L  H  T  K  L  K  G  F  H  T  Q  I  S  K  Y  F
```

FIG. 16A

```
370-        380-        390-        400-        410-        420-        430-
CTGAGGCGGTGATGCTGTAACCAAAGCAGCCAAGCAGCCCATGTGGGTGATTATCGGCAACTGGTACACG
 S  E  R  G  D  A  V  T  K  A  A  K  Q  P  H  V  G  D  Y  R  Q  L  V  H 440-        450-        460-        470-        480-        490-        500-
AGCTGGATGAGGCAGAGTACCGGGATATCCGGCTGATGGTCATGGAGATCGCAACGTACGCTGTGTTATATG
 E  L  D  E  A  E  Y  R  D  I  R  L  M  V  M  E  I  A  T  Y  A  V  L  Y 510-        520-        530-        540-        550-        560-        570-
ACATCATCCTGAAGAACTTCGAGAAGCTCAAGAAGCCCAGGGGAGAAACAAAGGGAATGATCTATTGAGACC
 D  I  I  L  K  N  F  E  K  L  K  K  P  R  G  E  T  K  G  M  I  Y  -

580-        590-        600-        610-        620-        630-        640-
CTCCCTCTCATTCTGTGATGGCTCCAACAGAGACCTTCTGACTTTTACAGGGACTCCAGACTTCCCCACCT 650-        660-        670-        680-        690-        700-        710-        720-
TCTGCCCTGTGTTGGTTTCTCCCCTTACCTCCCCAGGCACAATAAATATAGTCATTACCATTGCCAAAAAAA
```

The nucleotide sequence is SEQ ID No. 1 and the amino acid sequence is SEQ No. 2

FIG. 16B

REGULATORS OF THE PROTEASOME

Research relating to the development of this invention was supported in part by National Institutes of Health grant HL-06296. The U.S. government, therefore, has certain rights in the invention.

BACKGROUND OF THE INVENTION

Intracellular protein degradation plays a number of critical roles in the regulation of cellular protein metabolism. Most proteins are continuously synthesized and degraded within the life-span of the cell and, therefore, rates of degradation are important determinants of cellular levels of individual proteins. Furthermore, rates of degradation of many proteins often change significantly under various physiological and pathological conditions. The consequences of such changes can range from the specific regulation of key cellular processes to the net growth or atrophy of tissues. Examples of physiological or pathological conditions associated with atrophy of tissues such as skeletal muscle caused by increased rates of protein degradation include: muscular dystrophy, sepsis, cancer, thyrotoxicosis, diabetes, exposure to microgravity (spaceflight), AIDS, aging and others. Conversely, the lack of appropriate breakdown of proteins can lead to a detrimental accumulation of protein in, for example, Alzheimer's disease. Despite the physiological importance of protein degradation, the biochemical mechanisms by which it occurs are poorly understood. Even such fundamental features of protein degradation as the identities and relative roles of the proteases that catalyze the process have been unclear. Three important features of intracellular protein degradation are reviewed briefly here.

Non-lysosomal compartments are important sites for intracellular protein degradation. Protein degradation occurs by multiple cellular pathways that are located in multiple cellular compartments. The relative contributions and importance of these pathways seem to depend on the specific degraded protein and on the physiological state of the cell. For example, lysosomes, which historically were thought to mediate most intracellular proteolysis, degrade cellular proteins by processes which are particularly prominent during nutritional starvation and during certain hormonal states associated with tissue catabolism. Lysosomes also appear to degrade many membrane-bound proteins including cell surface receptors. Many other cellular proteins, however, are degraded by non-lysosomal mechanisms. For example, even when lysosomal proteolysis is maximally active, inhibition of this pathway reduces overall rates of protein degradation by only 20–50% (57). Under these same conditions, the degradation of may specific proteins, such as contractile proteins of muscle, is unaltered. Under "basal" metabolic conditions, where lysosomal autophagy is minimized, inhibition of lysosomal function has relatively little effect on overall rates of proteolysis, suggesting that other cellular pathways normally catalyze this major proteolytic process. In fact, the degradation of many proteins microinjected into cultured cells occurs in the cytoplasm. Finally, the regulated degradation of specific proteins such as cyclins, the tumor suppressor p53, and various transcription factors in the nucleus represents an important cellular control mechanism located in this organelle.

Intracellular protein degradation requires ATP. An apparently universal feature of protein degradation in intact cells is its dependence on metabolic energy. Part of ATP's role in protein degradation may be accounted for by its control of lysosomal function. The ATP-dependent proton pump of lysosomes lowers intralysosomal pH, a requirement for the action of lysosomal proteases. ATP also appears to be required for a recently discovered mechanism for the degradation of certain classes of proteins that are selectively target for lysosomal degradation. Nevertheless, the degradation of proteins known to occur by non-lysosomal pathways also requires ATP. Furthermore, protein degradation requires cellular energy even in cells that lack lysosomes. Such results suggest that other, perhaps more fundamental mechanisms, are responsible for this phenomenon. The multiple roles of ATP in the regulation of substrate ubiquitination and proteasome function (see below) may represent such mechanisms.

The degradation of intracellular proteins is selective. The normal rates of degradation of constituent cellular proteins are remarkably heterogeneous, varying by more than 1000-fold. Furthermore, alterations in protein structure resulting from mutations, chemical modifications or incorporation of amino acid analogs during synthesis greatly alter rates of proteolysis. Such results suggest that physical and chemical features of proteins determine protein half-lives and that cells contain degradative mechanisms which recognize these features. A number of studies have correlated specific biochemical features of proteins with degradative rates, although detailed biochemical bases for these correlations are unclear. Nevertheless, at least one of these features, the so-called "N-end rule", may be related to the ATP-ubiquitin-dependent pathway catalyzed by the proteasome system.

Within the past several years, important and rapid progress has been made in understanding the biochemical basis of aspects of each of the three features described above. First, non-lysosomal proteases with possible roles in protein degradation have been identified and characterized. These include the calpains and the proteasome; each of these proteases has been identified in the cytoplasm and in the nucleus of a wide variety of cells and species. A second area of important progress has been the development of cell-free systems that demonstrate selective, ATP-dependent proteolysis. The most extensively studied system, and one that appears to be a prototype for most eukaryotic cells, is soluble extracts of reticulocytes, where exogenous proteins are degraded by a complex, multicomponent pathway. A key component of this pathway is the protein ubiquitin which is hypothesized to serve as a molecular "marker" for proteolysis of certain substrates. Three enzymes catalyze a sequence of reactions that results in the covalent conjugation of ubiquitin to protein substrates. This reaction is obligatory for the subsequent degradation of various classes of proteins, including those known to be rapidly degraded in intact cells. Importantly, at least two steps in the ubiquitin pathway require ATP. The first step in this process, the activation of ubiquitin by the El ubiquitin-activating enzyme, requires ATP. Furthermore, the subsequent degradation of ubiquitinated proteins also requires ATP; the exact role of this latter effect is poorly understood but appears to involve the regulation of the responsible protease. Thus, this proteolytic pathway incorporates the key features of both energy dependence and substrate selectivity observed in intact cells.

The altered degradation of ubiquitinated proteins is a feature of aged cells and cells from patients with Alzheimer's Disease. Aged cells are known to accumulate specific proteins with identified amino acid deletions or substitutions that result in their decreased catalytic or functional activity. One explanation for such results is that the normal mechanism for the selective removal of these aberrant proteins is diminished in the aged cells. Alzheimer's Disease is characterized by the cellular accumulation of structures termed paired helical filaments in neurons in the brain. These paired helical filaments result in so-called inclusion bodies that are characteristic of a number of neurodegenerative diseases. In Alzheimer's Disease these inclusions are termed neurofibrillary tangles. One surprising but consistent feature of these inclusion bodies is that they have ubiquitin as a principal component. Numerous studies have shown that ubiquitin is markedly elevated in various brain areas in patients with Alzheimer's Disease. Although the exact relationship of inclusion bodies and associated ubiquitin to diseases such as Alzheimer's Disease is unclear, it is likely that the abnormal accumulation of dysfunctional proteins would interfere with normal cellular functions. It is also likely that the basis for the accumulation of such proteins is a defect in the cellular mechanism that is normally responsible for their removal. The ATP/ubiquitin/system is a likely candidate for this process and the proteasome is the principal if not the sole protease that catalyzes this pathway.

Despite the important role of protein degradation in these processes, the biochemical mechanisms of protein degradation are not completely clear. Recent evidence, however, indicates an important role for a specific intracellular protease, the proteasome.

The proteasome (also known as macropain, the multicatalytic protease, and 20 S protease) is a high molecular weight, multisubunit protease which has been identified in every examined species from an archaebacterium to human. The enzyme has a native molecular weight of approximately 650,000 and, as revealed by electron microscopy, a distinctive cylinder-shaped morphology (1,2). The proteasome subunits range in molecular weight from 20,000 to 35,000 (3–5), and are homologous to one another but not to any other known protease.

The proteasome enzyme is "multicatalytic," i.e. it has at least three distinctly different catalytic sites including: a peptidylglutamyl-peptide hydrolyzing site, which cleaves peptides with glutamic acid in the P1 position (e.g. CBZ-Leu-Leu-Glu-X); a "trypsin-like" site, which cleaves peptides with basic amino acids in the Pi position (e.g. CBZ-Val-Leu-Arg-X); and a "chymotrypsin-like" site, which cleaves peptides with leucine or other hydrophobic amino acids in the P1 position (e.g. CBZ-Gly-Gly-Leu-X). The proteasome has been identified in both cytoplasmic and nuclear compartments and appears to play a central role in non-lysosomal pathways of intracellular protein degradation, including those mediated by ATP and ubiquitin (17–20, 44). Its activity is high in muscle wasting diseases that involve protein breakdown such as muscular dystrophy, cancer and AIDS. Yeast with mutant proteasomes exhibit a decreased rate of degradation of normal short-lived and abnormal proteins and an accumulation of ubiquitinated proteins (16). The proteasome has also been implicated in ATP-dependent, ubiquitin-independent pathways of protein degradation, although its relative contribution to these various processes is unclear. Evidence also suggests a possible role for the proteasome in the processing of antigens for the class I MHC molecules (45).

The proteasome has been purified in two functionally distinct forms (21). One form displays all of the characteristic catalytic features described above, and has been termed the "A", or active proteasome. The second form displays all of the characteristic peptidase activities of the active proteasome, but has no activity toward large protein substrates. This proteolytically inactive form has been termed the "L", or latent proteasome because several treatments, including dialysis against water, exposure to certain polycations, or exposure to low concentrations of SDS, activate protease activity. The biochemical basis for proteasome activation by such diverse means is not defined, but probably results from conformational alterations of the enzyme. Rapid immunoprecipitation of the proteasome from various cell types indicated that cells normally contain the latent form of the proteasome (19). These results suggest that cells also contain physiological regulators of the proteasome that are required for enzyme activation.

In fact, several distinct proteasome regulatory proteins have been identified and characterized. These proteins include activators (46) and inhibitors (24, 27, 47) of the various hydrolytic activities of the multicatalytic proteasome, as well as proteins that confer upon it additional regulatory properties such as requirement for ATP and specificity for ubiquitinated substrates (26, 48). Yukawa et al. described a proteasome and its endogenous activator in human platelets (58). The activator enhanced chymotrypsin- or trypsin-like activities of the proteasome in a dose related manner and was inactivated by heating at 56° C. for 30 min. The activator did not enhance activity toward the substrates Z-ArgArg-AMC and Z-PheArg-AMC (58). No other information on this activator from platelets was available. Peptide aldehydes and peptide α-keto esters containing a hydrophobic residue in the P1 position were tested as potential inhibitors of the peptidase activities of the pituitary multicatalytic proteinase complex by Vinitsky et al. (59). Driscoll et al. (60) discusses an ATP-stabilized inhibitor of the proteasome from rabbit reticulocytes. Li et al. (47,56) isolated and characterized a 50-kDa inhibitor and a 40-kDa inhibitor of the proteasome.

An inhibitor protein, termed PI31, of the proteasome has been identified and purified from bovine red blood cells (27). PI31 has an apparent native Mr=60,000. On SDS-PAGE it consisted of a single polypeptide with an apparent Mr=31,000, and thus appears to be a homodimer. PI31 inhibited all of the peptidase and protease activities of both the latent and active forms of the proteasome by a non-competitive mechanism. This result suggests that PI31 may function as an allosteric regulator of the proteasome. The inhibitor and proteasome appear to interact in a 1:1 molar ratio. PI31 was specific for the proteasome, and this result suggests a physiological role for it in the regulation of the proteasome. Edman degradation of 6 tryptic peptides (containing a total of 65 amino acids) suggests that PI31 is an unique protein which has no homology with other known proteins. This inhibitor protein does not block the regulation of other activator proteins. Despite the important implications of these studies for proteasome regulation, little is known about the relative interaction of the different regulatory proteins with the proteasome. Furthermore, the tissue distribution of these regulatory proteins, which have been identified and studied only in red blood cells, is not known. Because such information would provide insight about their cellular roles, the present inventors sought to identify, purify and characterize such regulatory factors.

ABBREVIATIONS

AMC: 7-amido-4-methylcoumarin
βNA: β-naphthylamide
DTT: Dithiothreitol
MNA: 4-methoxy-β-naphthylamide
MOPS: 4-morpholinepropanesulfonic acid
$M_r$: molecular weight
PAGE: polyacrylamide gel electrophoresis PIR: database for sequence searches
SDS: sodium dodecyl sulfate
Suc-: succinyl
Z-: benzyloxycarbonyl-

SUMMARY OF THE INVENTION

The present invention provides a proteasome activating factor, separated from proteasome, which activates hydrolysis by proteasomes of substrates comprising Z-Arg-Arg-AMC. "Separated from proteasome" means having insufficient proteasome present to cause undesired proteolysis. The proteasome activating factor may elute from a DEAE ion-exchange column at a sodium chloride concentration of about 100 mM. The proteasome activating factor may require ATP for activation of proteasomal hydrolysis of substrates. The proteasome activating factor may be ATP-independent in its activation of proteasomes. A preferred proteasome activating factor is separated from proteasome and has a molecular weight between 25,000 and 30,000 daltons, in particular, a molecular weight of about 28,000 daltons. This factor elutes from an ion-exchange column at a sodium chloride concentration of about 100 mM. The proteasome activating factor is defined further as substantially comprising the amino acid sequence of FIG. 16. The proteasome activating factor is defined further as having activating activity for proteasome hydrolysis of trypsin-like, chymotrypsin-like and peptidylglutamyl-like substrates.

A further aspect of the present invention is an ATP-dependent proteasome activating factor separated from proteasome and having a native molecular weight between 600,000 and 800,000 daltons, in particular, about 700,000 daltons. The ATP-dependent proteasome activating factor is defined further as having activating activity for proteasome hydrolysis of trypsin-like, chymotrypsin-like and peptidylglutamyl-like substrates.

A further embodiment of the present invention is a method for preparing a proteasome activating factor comprising the steps of i) fractionating an extract from eukaryotic cells; and ii) collecting fractions containing proteasome activating activity eluting from a DEAE ion exchange column at a sodium chloride concentration of about 100 mM. One skilled in the art would recognize that a proteasome activating factor could also be prepared from prokaryotic sources containing a proteasome activating factor, since the proteasome has been identified in every examined species from an archaebacterium to human. In particular, a method is claimed for preparing a proteasome activating factor from mammalian red blood cells, comprising the steps of i) lysing mammalian red blood cells to obtain a cell lysate; ii) separating cellular debris to obtain a lysate supernatant; iii) chromatographically fractionating an activating factor from the supernatant; and iv) collecting chromatography fractions rich in activating factor eluting from a DEAE ion exchange column at a sodium chloride concentration of about 100 mM. The chromatographic fractionation may include successive chromatography steps on Sephacryl S-300, DEAE-Sephacel, Hydroxylapatite, and Phenyl-Sepharose.

An embodiment of the present invention is a method for treating an individual for disease in which ubiquitinated proteins accumulate. The method comprises the administration of a therapeutically effective amount of a proteasome activator or fragment thereof which activates proteasome activity to thereby increase degradation of ubiquitinated proteins.

A further aspect of the invention is a method for preparing an ATP-dependent proteasome activating factor, comprising the steps of i) fractionating an extract from eukaryotic cells; and ii) collecting fractions containing ATP-dependent proteasome activating activity. In particular, a method is claimed for preparing an ATP-dependent proteasome activating factor from mammalian red blood cells, comprising the steps of i) lysing mammalian red blood cells to obtain a cell lysate; ii) separating cellular debris to obtain a lysate supernatant; iii) chromatographically fractionating an ATP-dependent activating factor from the supernatant; and iv) collecting chromatography fractions rich in ATP-dependent activating activity. The chromatographic fractionation may include successive chromatography steps on Sephacryl S-300, DEAE-Fractogel, and Hydroxylapatite.

A further embodiment of the present invention is a first polynucleotide purified free from total cellular DNA having the sequence of SEQ ID NO. 1, a second polynucleotide complementary to the first polynucleotide, a polynucleotide differing from the first or second polynucleotide by codon degeneracy, a polynucleotide which hybridizes with the first or second polynucleotide, or an oligonucleotide probe for the first or second polynucleotide which hybridizes with said polynucleotide. In particular, a polynucleotide in substantially pure form is claimed which encodes proteasome activator PA28 comprising the sequence of SEQ ID NO. 1:

A recombinant nucleic acid molecule comprising a polynucleotide encoding proteasome activator PA28 is a further aspect of the present invention. The recombinant nucleic acid molecule may be an expression vector for the overproduction of proteasome activator PA28 or fragment thereof. Also claimed is a host cell comprising an expression vector for said activator or fragment thereof. A further embodiment of the present invention is a method for preparing a purified recombinant proteasome activating factor, PA28, or fragment thereof, comprising i) culturing said host cells; ii) fractionating an extract from the host cells; and iii) collecting fractions containing recombinant proteasome activating activity.

A preferred embodiment of the present invention is a carboxy-terminal PA28 fragment having inhibitory activity for the activation of proteasomes by a proteasome activator and defined further as containing a carboxy-terminal Ile-Tyr sequence. The carboxy-terminal fragment of PA28 may contain from 2 to about 50 amino acids, more particularly, 2 to about 20 amino acids, and most particularly, about 18 amino acids. The carboxy-terminal fragment of PA28 is defined further as comprising the sequence of SEQ ID NO. 3: Lys Asn Phe Glu Lys Leu Lys Lys Pro Arg Gly Glu Thr Lys Gly Met Ile Tyr. The N-terminal Lys may be acetylated. Also claimed is a peptide inhibitor of proteasome activation comprising the sequence of SEQ ID NO. 3; the N-terminal Lys may be acetylated. The carboxy-terminal fragment of PA28 is defined further as comprising an amino acid sequence corresponding to residues 172 to 189 of FIG. 16A and FIG. 16B. The carboxy-terminal PA28 fragment may comprise less than 18 amino acids or may comprise functionally equivalent amino acid replacements which allow similar binding activity. One skilled in the art would realize that the human sequence of PA28 may have different but functionally equivalent amino acids compared to the bovine sequence and that the pharmaceutically desired composition would include the human sequence.

Another embodiment of the present invention is a method of inhibiting the activation of proteasome activity. The method comprises exposing proteasomes in a biological fluid to an amount of a carboxy-terminal PA28 fragment having inhibitory activity for the activation of proteasomes by a proteasome activator. The carboxy-terminal PA28 fragment is defined further as containing a carboxy-terminal Ile-Tyr sequence of amino acids. The amount of PA28 fragment is sufficient to inhibit activation of proteasome activity. In particular, a method is claimed for treating an individual to inhibit undesired muscle wasting. The method comprises the administration of a pharmaceutically acceptable composition comprising a therapeutically effective amount of the carboxy-terminal PA28 peptide which inhibits the activation of proteasome activity and thereby inhibits the degradation of muscle proteins. The undesired muscle wasting may result from muscular dystrophy, sepsis, thyrotoxicosis, diabetes, exposure to microgravity, cancer, AIDS or aging. The pharmaceutically acceptable composition may comprise a therapeutically effective amount of the peptide having the sequence of SEQ ID NO. 3: Lys Asn Phe Glu Lys Leu Lys Lys Pro Arg Gly Glu Thr Lys Gly Met Ile Tyr, which inhibits the activation of proteasome activity and thereby inhibits degradation of muscle proteins. The undesired muscle wasting may result from muscular dystrophy, sepsis, thyrotoxicosis, diabetes, cancer, AIDS or aging. A therapeutically effective amount of an inhibitor is a sufficient amount to maintain an in vitro concentration in vivo in the locale of the proteasome inactivating the activity of said proteasome. The administering is preferably parenteral, i.e., intravascular, intracisternal or intramuscular. If peptides having the essential characteristics are resistant to the digestive tract, enteral administration may be used.

A further embodiment of the present invention is a PA28inactivating protein substantially purified from total cellular protein which degrades a PA28 proteasome activating activity of PA28 by removing carboxy-terminal amino acids of PA28. The PA28inactivating protein is defined further as being isolatable from red blood cells. A PA28-inactivating protein which inactivates a PA28 proteasome activating activity of PA28 by removing carboxy-terminal amino acids may be prepared by a method comprising the steps of i) fractionating an extract from eukaryotic cells; and ii) collecting fractions containing a PA28-inactivating protein. The PA28-inactivating protein may be prepared from mammalian red blood cells, comprising the steps of i) separating cellular debris from a mammalian red blood cell lysate to obtain a lysate supernatant; ii) chromatographically fractionating a PA28inactivating protein from the supernatant; and iii) collecting chromatography fractions rich in PA28-inactivating protein. The chromatographic fractionation may include successive chromatography steps on Hydroxylapatite, DEAE-Fractogel and Sephacryl S-100.

A most preferred embodiment is a composition comprising PA700 and PA28 wherein the composition activates proteasomes for the degradation of protein substrates.

BRIEF DESCRIPTION OF THE DRAWINGS

" FIG. 6A, purified 20 S proteasome A (85 μg) was incubated at 25° C. for 10 min. and then centrifuged. Fifty-μl samples of the fractions were assayed for Suc-Leu-Leu-Val-Tyr-AMC hydrolyzing activity. FIG. 6B, purified PA28 (4.5 μg, 1600 units) was incubated at 25° C. for 10 min. and then centrifuged. Samples (50 μl) of the fractions were assayed for PA28 activity in the presence of 1.3 μg (0.4 units) of purified 20 S proteasome A. FIG. 6C, purified 20 S proteasome (85 μg) and purified PA28 (4.5 μg) were preincubated for 10 min. at 25° C. and then centrifuged. Samples of the fractions were assayed for proteasome activity in the presence (▲) and absence (●) of exogenous proteasome, under the same conditions as in FIGS. 6A and 6B, respectively. Protein standards: thyroglobulin ($M_r$= 669,000); aldolase ($M_r$=158,000). Similar results were obtained in two independent experiments.

FIG. 7A, Z-Val-Leu-Arg-MNA, 3.7 nM proteasome, 15 nM PA28. FIG. 7B, Z-Gly-Gly-Leu-AMC, 0.4 nM proteasome, 1 nM PA28. FIG. 7C, Z-Leu-Leu-Glu-βNA, 0.4 nM proteasome, 1 nM PA28. FIG. 7D, Suc-Leu-Leu-Val-Tyr-AMC, 0.2 nM proteasome, 4 nM PA28 (note difference in scales in FIG. 7D).

FIG. 8A, Z-Val-LeuArg-MNA, 3.7 nM proteasome, 15 nM PA28. FIG. 8B, Z-Gly-Gly-Leu-AMC, 2.0 nM proteasome, 11 nM PA28. FIG. 8C, Z-Leu-Leu-Glu-βNA, 0.4 nM proteasome, 1 nM PA28. FIG. 8D, Suc-Leu-Leu-Val-Tyr-AMC, 0.2 nM proteasome, 4 nM PA28 (note difference in scales in panel D).

FIG. 9A, Z-Val-Leu-Arg-MNA (50 μM), proteasome, 4 nM. FIG. 9B, Z-Gly-Gly-Leu-AMC, (50 μM), proteasome, 2 nM. FIG. 9C, Z-Leu-Leu-Glu-βNA, (250 μM), proteasome, 2 nM. FIG. 9D, Suc-Leu-Leu-Val-Tyr-AMC (50 μM), proteasome, 1 nM.

FIG. 12A, Carboxypeptidase B-treated PA28, without proteasome; FIG. 12B, Carboxypeptidase B-treated PA28, with proteasome; FIG. 12C, Untreated PA28, with proteasome; and FIG. 12D, Untreated PA28, without proteasome.

FIG. 14 shows SDS-PAGE of purified PA28-inactivating protein. Purified PA28-inactivating protein (1.5 μg) was subjected to SDS-PAGE in 12.5% gels.

FIG. 16A and FIG. 16B show the nucleotide sequence and amino acid sequence of a partial clone encoding the PA28 activator protein. A bovine brain cDNA library was screened with antibodes against PA28. The positive clone with the largest insert was isolated and sequenced. The open reading frame includes codons for 189 amino acids ($M_r$=21,893). The underlined residues correspond to tryptic peptides of PA28 sequenced by automated Edman degradation. All are in complete agreement with the deduced sequences.

DETAILED DESCRIPTION OF THE PREFERRED EMBODIMENTS

Figure 1A:
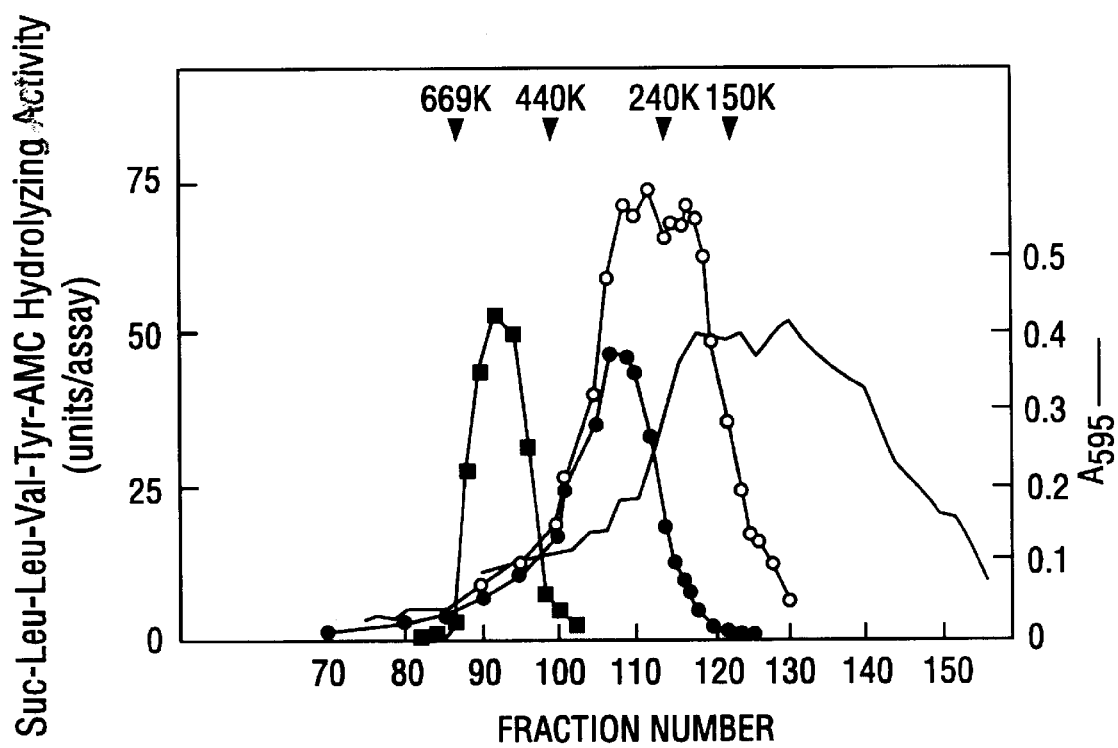
FIG. 1A and FIG. 1B provide the identification of a proteasome activator on Sephacryl S-300 column chromatography. An ammonium sulfate fraction (proteins precipitating between 40–85% saturation) of a bovine red blood cell lysate, prepared as described under "Materials and Methods," was chromatographed on Sephacryl S-300. The eluted fractions were assayed for the ability to hydrolyze the peptide substrate Suc-Leu-Leu-Val-Tyr-AMC (50 μM) under two different conditions. In the first, 5 μl of the column fractions were assayed for hydrolyzing activity under standard conditions (●). In the second, 5 μl of the column fractions were assayed in the presence of 1.3 μg (0.4 units) of purified bovine red blood cell 20 S proteasome A (○). Inset, the Suc-Leu-Leu-Val-Tyr-AMC hydrolyzing activity measured in the absence of exogenous proteasome was subtracted from the activity measured in the presence of exogenous proteasome and the values are plotted as shown. In a separate chromatographic experiment, 250 μg of purified bovine red blood cell 20 S proteasome A was chromatographed under the same column conditions, and 200 μl of the column fractions was assayed (■). Five-μl samples of column fractions were assayed for total protein as described under "Materials and Methods" (–). The column was calibrated with proteins of known molecular weight: thyroglobulin ($M_r$=669,000); apoferritin ($M_r$=440,000); catalase ($M_r$=240,000); alcohol dehydrogenase ($M_r$=150,000).

A protein, PA28, that greatly stimulates the multiple peptidase activities of the 20 S proteasome has been purified from bovine red blood cells and from bovine heart. The activator protein is a single polypeptide with an apparent molecular weight of 28,000 as determined by sodium dodecyl sulfate-polyacrylamide gel electrophoresis, and has a native molecular weight of approximately 180,000. This protein regulated all three of the putatively distinct peptidase activities displayed by each of two functionally different forms of the proteasome. This regulation usually included both an increase in the maximal reaction velocity and a decrease in the concentration of substrate required for half-maximal velocity and indicated that PA28 acted as a positive allosteric effector of the proteasome. PA28 failed, however, to stimulate the hydrolysis of large protein substrates such as casein and lysozyme. These results suggested that the hydrolysis of protein substrates occurred at a site or sites distinct from those that hydrolyzed small peptides and that the regulation of the two processes could be uncoupled. Evidence for direct binding of PA28 to the proteasome was obtained by glycerol density gradient centrifugation. Example I describes the purification and characterization of PA28.

In order to determine whether PA28 is as widely distributed as the proteasome, PA28 content and activity were examined in various eukaryotic tissues by immunoblot analysis and by functional assays of tissue extracts. PA28 protein was present in all sources examined, indicating that it, like the proteasome, is widely distributed. PA28 activity, however, was not detected in many of these sources including those with the highest level of PA28 protein. In order to determine the biochemical basis of this result, PA28 was purified from extracts of rat liver, which had high levels of PA28 protein but no PA28 activity. The resulting purified PA28 had no detectable activity but had native and subunit molecular weights (180,000 and 28,000, respectively) indistinguishable from the active PA28 of bovine red blood cells. It appeared that some tissues contained a protein that inactivated PA28 either in intact cells or during preparation of the extract. Using the inactivation of purified PA28 as an assay, a protein that inactivated PA28 without altering its apparent molecular weight on SDS-PAGE was identified, purified, and characterized from bovine liver. It had biochemical and catalytic characteristics similar to lysosomal carboxypeptidase B. When leupeptin, an inhibitor of lysosomal carboxypeptidase B, was included in the buffers used for the preparation of PA28, PA28 activity was detected in tissues which otherwise failed to demonstrate this activity. A similar result was obtained when extracts were prepared in a manner that minimized disruption of lysosomes. Other carboxypeptidases such as carboxypeptidase Y from yeast and bovine pancreatic carboxypeptidase B also inactivated PA28 without altering its apparent molecular weight. Both active and inactive PA28 were blocked to N-terminal amino acid sequencing, providing further evidence for the modification occurred at the carboxyl terminus of the protein. Active PA28 binds to the proteasome to form a protease-activator complex that can be isolated after velocity sedimentation centrifugation through glycerol density gradients. Carboxypeptidase-inactivated PA28 failed to form such a complex, suggesting that the carboxyl terminus of PA28 is required for binding to the proteasome. These results indicate the importance of the carboxyl terminus of PA28 for proteasome activation. Example II describes the identification, purification and characterization of a protein that inactivates PA28.

Example III describes the cloning, nucleotide sequence and amino acid sequence of PA28. Example IV describes the identification, purification and characterization of a high molecular weight, ATP-dependent activator (PA700) of the 20S Proteasome. It has endogenous ATPase activity as an isolated protein and has no protease or peptidase activity by itself. Example V describes a peptide inhibitor of proteasome activation. Example VI describes synergism with PA700 and PA28 activating the proteasome to degrade large protein substrates.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. Unless mentioned otherwise, the techniques employed herein are standard methodologies well known to one of ordinary skill in the art.

EXAMPLE I

PA28, an Activator Protein for the Proteasome

The present example describes the identification and characterization of an activator protein, PA28, for the 20 S proteasome.

Materials And Methods

Purification of a Protein Activator of the 20 S Proteasome—Fresh bovine blood was obtained from a packing house using sodium citrate as an anticoagulant. The red cells were collected by centrifugation at 2000×g for 1 h. The cells were resuspended in 4 volumes of phosphate-buffered saline and recentrifuged. This procedure was repeated three times. A typical preparation started with 1500–1800 ml of packed cells. All of the following procedures were carried out at 4° C. The cells were lysed with 3 volumes of a buffer containing 20 mM Tris-HCl, pH 7.6, 20 mM NaCl, 1 mM EDTA, and 1 mM β-mercaptoethanol (buffer H). After gentle mixing for 15 min., the lysate was centrifuged for 60 min. at 13,000×g. The supernatant was removed, mixed with 1000 ml of DEAE-cellulose (DE52, Whatman), and stirred gently for 30 min. The DE52 was filtered on a Buchner funnel using Whatman 1 paper and washed with 1500 ml of buffer H. The washed resin was then added to 500 ml of buffer H containing 0.5M NaCl, mixed for 15 min., refiltered, and washed with more buffer. The filtrate was brought to 40% saturation with respect to ammonium sulfate. The precipitated proteins were collected by centrifugation and discarded. The supernatant was brought to 85% saturation with respect to ammonium sulfate, and the precipitated proteins were collected by centrifugation. The resulting pellet was dissolved in a small amount of buffer H and dialyzed overnight against 2000 ml of buffer H containing 100 mM NaCl.

The dialyzed sample was centrifuged at 30,000×g for 30 min to remove any undissolved material and chromatographed on a column of Sephacryl S-300 (110×5-cm), equilibrated, and eluted with buffer H containing 100 mM NaCl. Fractions of 11 ml were assayed for proteasome activity using the synthetic peptide substrate Suc-Leu-Leu-Val-Tyr-AMC (see below) in the presence and absence of exogenous purified proteasome (see FIG. 1A and FIG. 1B). The fractions containing the proteasome activator were pooled, dialyzed against a buffer composed of 20 mM MOPS, pH 7.0, 50 mM NaCl, 1 mM EDTA, and 1 mM β-mercaptoethanol.

The dialyzed material was applied to an 8×2.5-cm column of DEAE-Sephacel, equilibrated with the dialysis buffer. After the column was washed with 2 column volumes of the started buffer, the bound proteins were eluted with a 320-ml linear gradient of NaCl (50–350 mM) in the MOPS buffer. Fractions of 5 ml were collected, and samples were assayed for the activator as described below. The active fractions were pooled and dialyzed against 5 mM potassium phosphate buffer, pH 7.6, 1 mM β-mercaptoethanol.

The dialyzed sample was applied to a 2.5-cm diameter column containing 8 g of hydroxylapatite, equilibrated with the 5 mM phosphate buffer. After the column was washed with 2 column volumes of the starting buffer, the bound proteins were eluted with a 320-ml linear gradient of phosphate (5–200 mM). Fractions of 5 ml were collected, and samples were assayed for the proteasome activator. The active fractions were pooled and dialyzed against buffer H containing 150 mM NaCl.

The dialyzed sample was applied to a 2.5×10-cm column of phenyl-Sepharose CL-4B, equilibrated with buffer H containing 150 mM NaCl. The column was washed with 1 column volume of starting buffer. The bound proteins were eluted with 320 ml of a linear gradient that decreased all components of the starting buffer to 0 mM and increased ethylene glycol from 0–25%. Fractions of 5 ml were collected and samples were assayed for the proteasome activator. The active fractions were pooled, dialyzed extensively against buffer H, concentrated, and used for further analysis as described in the text. The activator was stored frozen at −70° C. No loss of activity has been detected after more than 6 months of storage under these conditions.

Purification of the Proteasome--Highly purified proteasome A (active form) and highly purified proteasome L (latent form) were prepared from bovine red blood cells or bovine heart, as described (5,21).

Assays for the Proteasome and the Proteasome Activator, PA28—The proteasome was assayed by the hydrolysis of proteins or synthetic peptide substrates. Proteasome activity against protein substrates such as [methyl-$^{14}$C]casein (2800 dpm/$\mu$g) and [methyl-$^{14}$C]lysozyme (6200 dpm/$\mu$g) was determined as described, except the final assay volume was 70 $\mu$l (5,21). Each assay contained 7.5 $\mu$g of protein substrate. One unit of proteasome activity is defined as the release of 1 dpm of acid soluble radioactivity/minute under standard assay conditions (5,21). Proteasome activity against synthetic peptide substrates Z-Val-Leu-Arg-MNA, Z-Gly-Gly-Leu-AMC, Suc-Leu-Leu-Val-Tyr-AMC, Z-LeuLeu-Glu-βNA and Z-Arg-Arg-MNA (purchased from Enzyme Systems Products or Bachem) was determined in assays that directly and continuously monitored the appearance of fluorescent products of hydrolysis. The fluorescent reporter compounds were monitored as follows: 4-methoxy-β-naphthylamide (MNA), excitation 340 nm/emission 425 nm; β-naphthylamide (βNA), excitation 335 nm/emission 410 nm; 7-amido-4-methylcoumarin (AMC), excitation 380 nm/emission 460 nm. The assays contained 50 mM Tris-HCl, pH 7.8, 1 mM dithiothreitol, substrate, and enzyme concentrations as indicated in legends for specific experiments in a final volume of 1.0 ml. Incubations were carried out at 30° C. Steady state rates of substrate hydrolysis were determined from the initial, linear portions of progress curves. These assays were typically conducted for 5–10 min. One unit of proteasome activity is defined as the change in concentration of fluorescent product of 1.0 nM/min under standard assay conditions. Standard curves were prepared for each reporter compound. Except for the assays of column fractions, all data points represent the average of duplicate assays.

Protein Determinations—Protein was determined by the Bradford assay using commercially prepared reagents from Bio-Rad (28).

Polyacrylamide Gel Electrophoresis—Polyacrylamide gel electrophoresis was carried out in 10% acrylamide gels in the presence of SDS as described (21).

Glycerol Density Gradient Centrifugation—Glycerol density gradient centrifugation was conducted with 10–40% glycerol gradients containing 20 mM Tris-HCl, pH 7.6, and 1 mM dithiothreitol. The gradient volume was 4.55 ml. Samples were centrifuged for 16 h at 30,000 rpm in Beckman SW 50.1 rotor. Aliquots of 200 μl were collected from each tube and subjected to analysis as described in the text. Some tubes contained marker proteins as indicated in the figures.

Results and Discussion

Figure 1B:
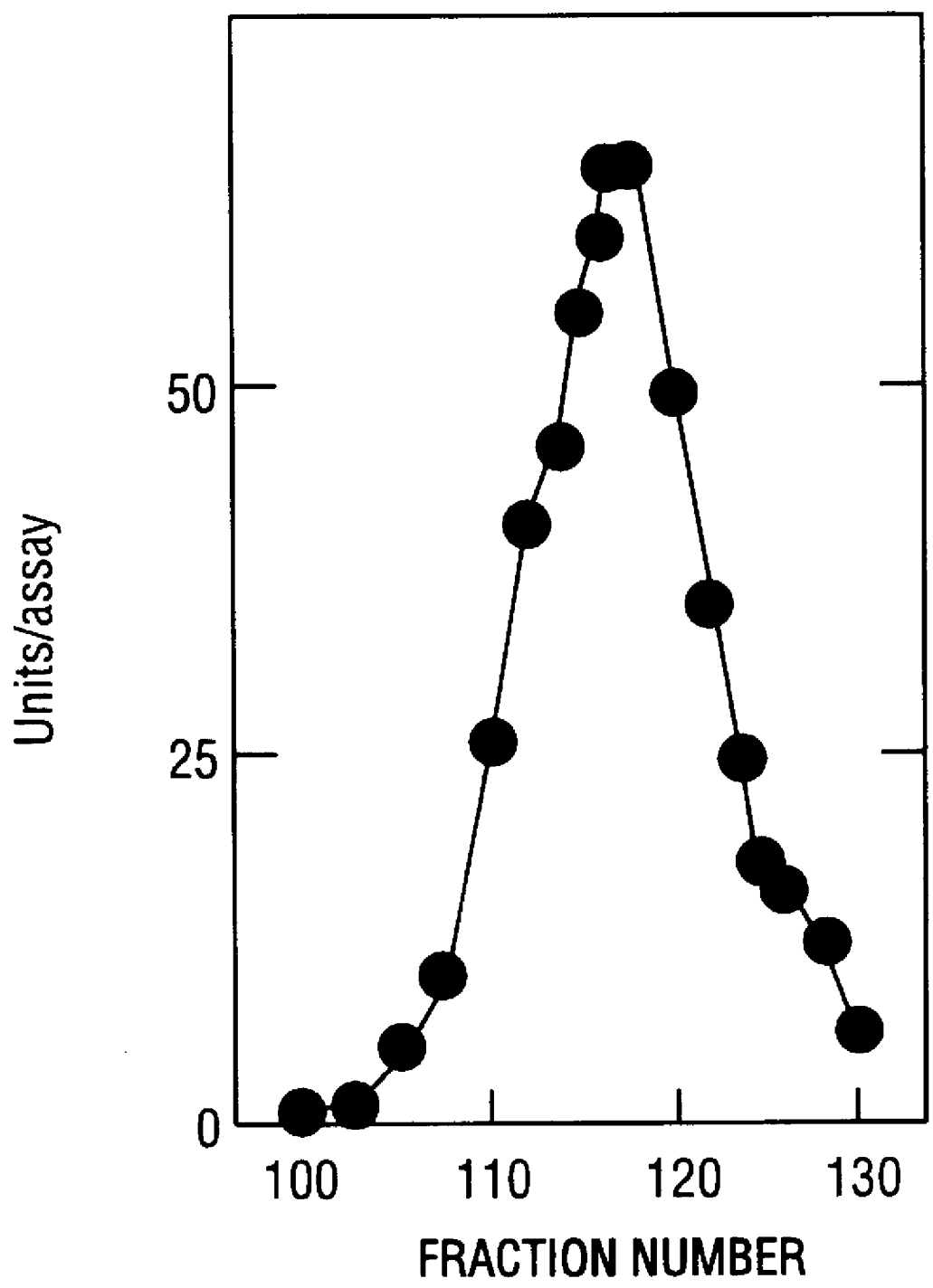

Identification and Purification of PA28, a Protein Activator of the 20 S Proteasome—In order to identify proteins that regulate the 20 S proteasome, the present inventors have tested the ability of fractionated cell and tissue extracts to influence the hydrolytic activities of the purified enzyme. In the present example, an ammonium sulfate fraction (proteins precipitated between 40 and 85% saturation, see "Materials and Methods") of a soluble lysate of bovine red blood cells was subjected to gel filtration chromatography on Sephacryl S-300. Samples of the eluted fractions were added to purified 20 S proteasome to determine their effect on the hydrolysis of Suc-Leu-Leu-Val-Tyr-AMC, a synthetic peptide substrate for this protease. Because the protein sample applied to the column was known to contain the 20 S proteasome, the eluted fractions were also assayed directly for endogenous proteasome activity with the same substrate. Thus, the two sets of assays differed only by the presence or absence of exogenous purified proteasome. Suc-Leu-Leu-Val-Tyr-AMC hydrolyzing activity endogenous to the column fractions appeared as a single peak corresponding to an apparent molecular weight of 300,000 (see FIG. 1A and FIG. 1B). This result was surprising because control experiments demonstrated that the purified 20 S proteasome eluted from this column with an apparent molecular weight of 650,000, the expected value for this protease (FIG. 1A and FIG. 1B) (5). The observed results have several possible explanations. First, the fractions might have contained a 300,000 molecular weight enzyme with much more Suc-Leu-Leu-Val-Tyr-AMC hydrolyzing activity than that of the endogenous proteasome. Alternatively, the column fractions could contain a proteasome activator protein with a molecular weight lower than 300,000. In this case, the overlapping portions of the elution profiles of the hypothetical activator protein and the endogenous proteasome would produce a peak of Suc-Leu-Leu-Val-Tyr-AMC hydrolyzing activity at a point between these individual peaks. Support for this latter possibility was obtained by the assays of column fractions conducted in the presence of the exogenous, purified proteasome. Because the activity of the exogenously added proteasome by itself was insignificant (0.4 units/assay) compared to the endogenous Suc-Leu-Leu-Val-Tyr-AMC hydrolyzing activity of the column fractions, the total observed activity was much greater than that expected for the simple additive effect. Furthermore, a second peak of peptide hydrolyzing activity was detected with a lower apparent molecular weight than that of the endogenous activity (FIG. 1A and FIG. 1B). Each of these features could be explained by the presence of a protein that greatly enhanced the activity of the proteasome. This stimulatory activity can be represented by calculating the difference between the total peptidase activity in the presence of the added proteasome and the endogenous activity of the column fractions. In fact, this calculation demonstrated an activity with a symmetrical elution profile at an apparent molecular weight of approximately 200,000, a position consistent with the explanations provided above (FIG. 1A and FIG. 1B, inset).

Figure 2:
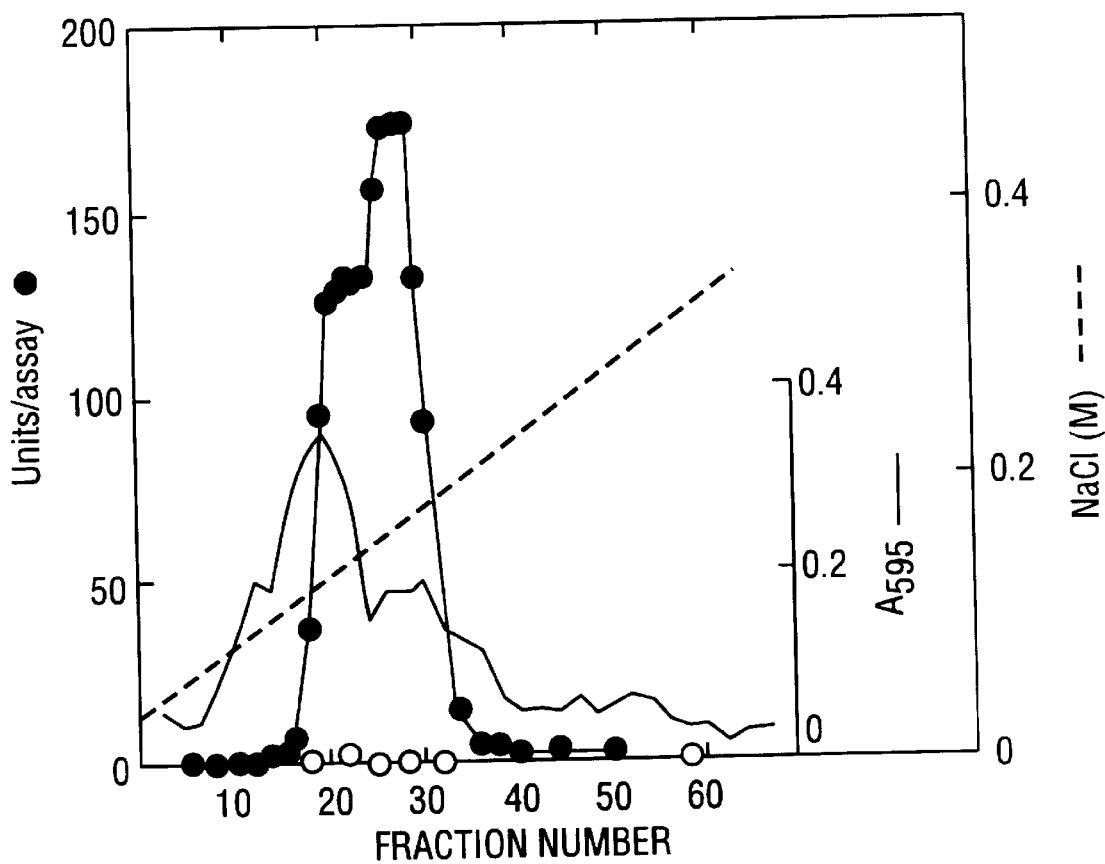
FIG. 2 shows DEAE-Sephacel ion-exchange chromatography. Fractions 110–121 from the Sephacryl S-300 column (FIG. 1) were pooled and subjected to ion-exchange chromatography of DEAE-Sephacel as described under "Materials and Methods." Five-μl samples of the fractions were assayed for Suc-Leu-Leu-Val-Tyr-AMC hydrolyzing activity (50 μM substrate) in the presence (●) and absence (○) of 1.3 μg (0.4 units) of purified 20 S proteasome A, as in the legend to FIG. 1.
Figure 3:
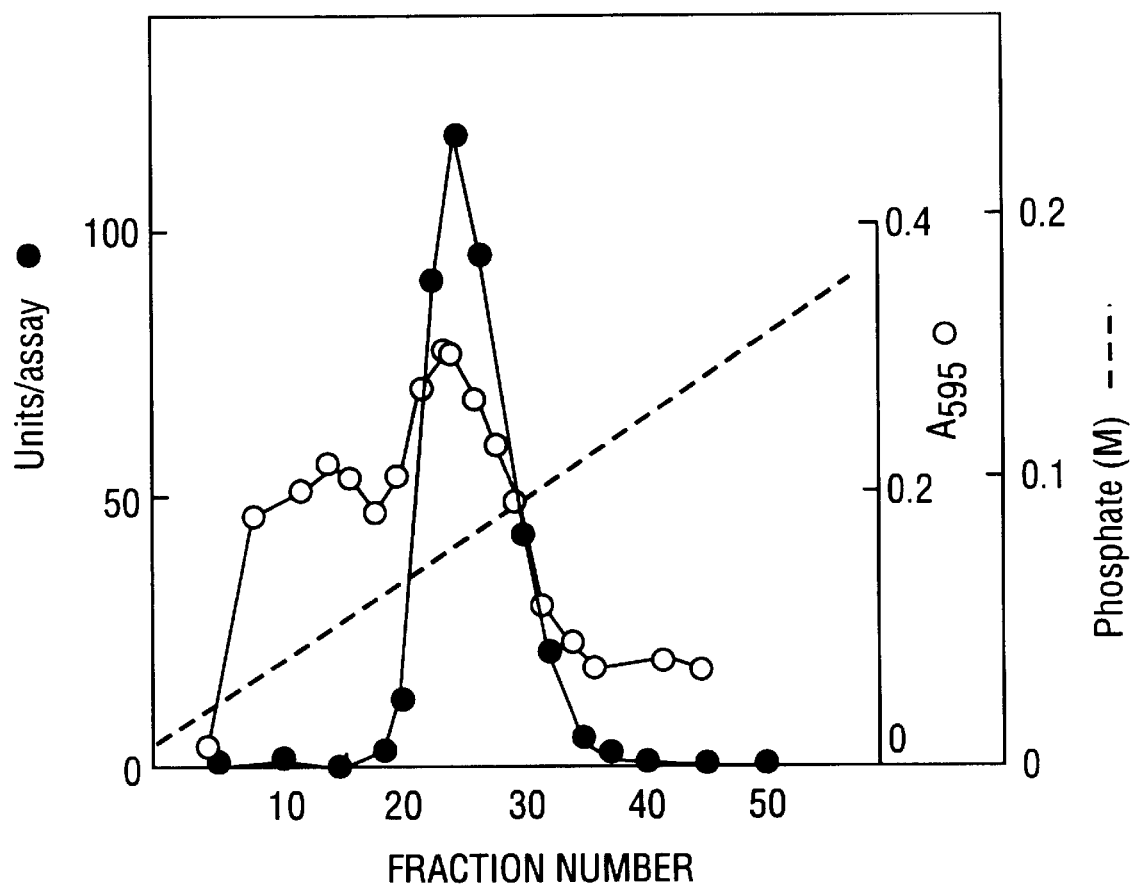
FIG. 3 shows hydroxylapatite chromatography. Fractions 21–31 from the ion-exchange chromatography (FIG. 2) were pooled and subjected to hydroxylapatite chromatography as described under "Materials and Methods." Five-μl samples of the fractions were assayed for Suc-Leu-Leu-Val-Tyr-AMC hydrolyzing activity (50 μM substrate) in the presence of 1.3 μg (0.4 units) of purified 20 S proteasome A (●). Protein (○).
Figure 4:
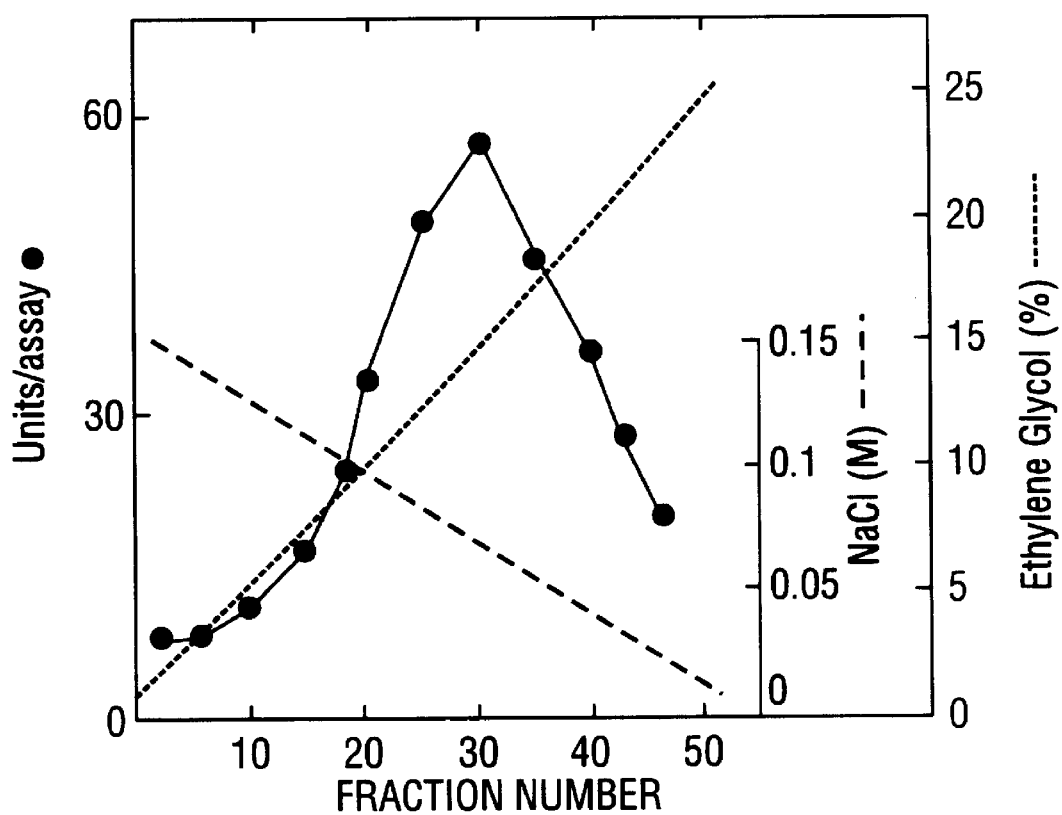
FIG. 4 shows hydrophobic interaction chromatography on phenyl-Sepharose. Fractions 21–32 from the hydroxylapatite chromatography (FIG. 3) were pooled and subjected to chromatography on phenyl-Sepharose as described under "Materials and Methods." Five-μl samples of the fractions were assayed for Suc-Leu-Leu-Val-Tyr-AMC hydrolyzing activity (50 μM substrate) in the presence of 1.3 μg (0.4 units) of purified 20 S proteasome A (●).

In order to further test the hypothesis of the existence of a proteasome activator, the fractions containing this putative protein were pooled and subjected to a series of chromatographic separations including, ion-exchange chromatography on DEAE-Sephacel (FIG. 2), hydroxylapatite chromatography (FIG. 3), and hydrophobic interaction chromatography on phenyl-Sepharose (FIG. 4), as described under "Materials and Methods" and summarized in Table 1.

TABLE 1

Purification summary of PA28 from bovine red blood cells.[1]

| Stage | Volume | Protein | Total activity | Specific activity |
|---|---|---|---|---|
|  | ml | mg | units × $10^{-3}$ | units/mg × $10^{-3}$ |
| Lysate supernatant | 2000 | 5500 |  |  |
| Ammonium sulfate (40–85%) | 50 | 3900 |  |  |
| Sephacryl S-300 | 132 | 700 | 1580 | 1.9 |
| DEAE-Sephacel | 55 | 210 | 1320 | 6.3 |
| Hydroxylapatite | 60 | 50 | 840 | 16.8 |
| Phenyl-Sepharose | 50 | 1.0 | 356 | 356 |

[1]Summary of a typical purification scheme for PA28 from bovine red blood cells, as detailed under "Materials and Methods." Activity measurements were made with the substrate Suc—Leu—Leu—Val—Tyr—AMC (50 μM) and active 20 S proteasome. Similar results were obtained in three independent preparations.

Figure 5:
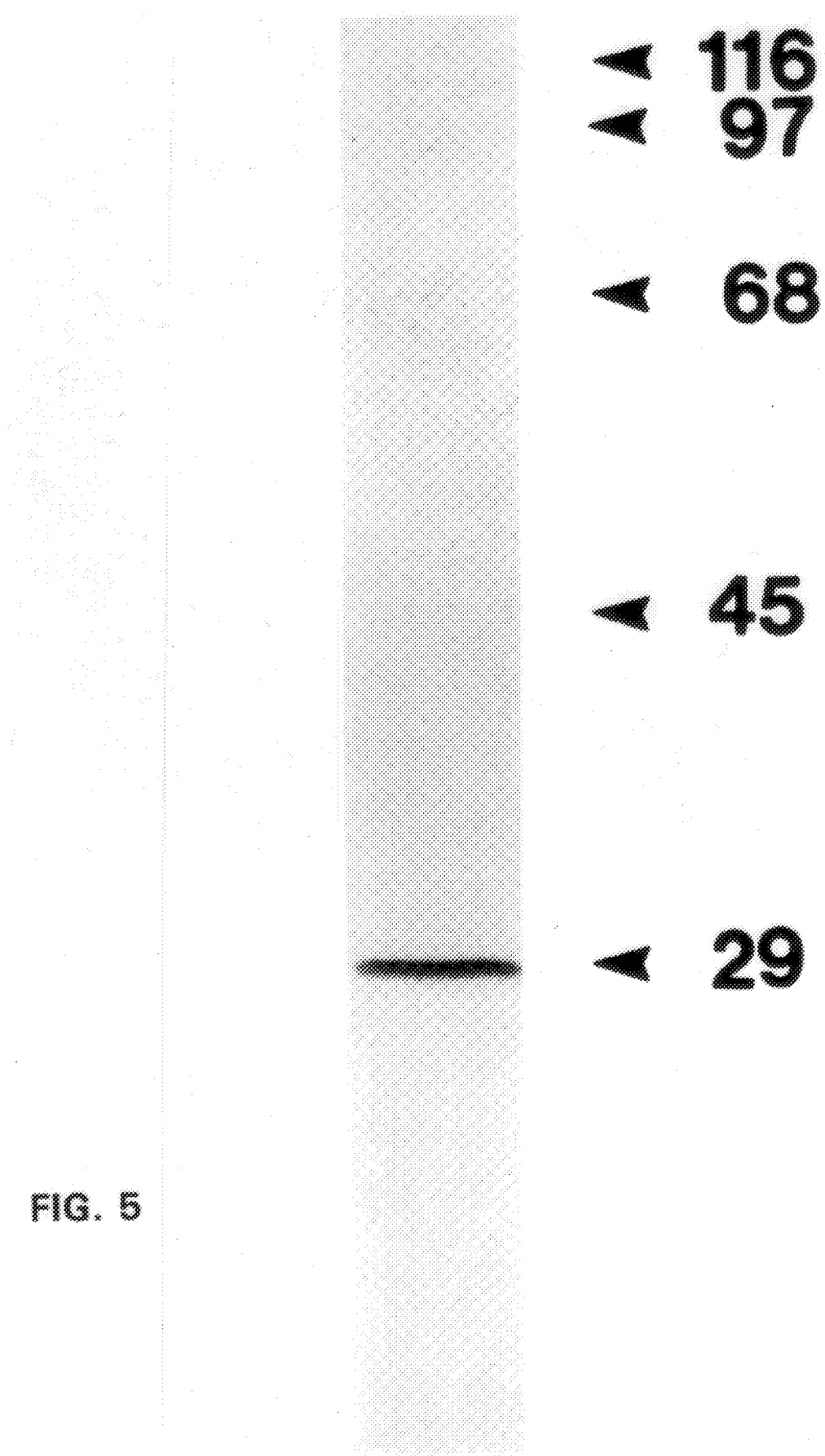
FIG. 5 shows SDS-PAGE of PA28. PA28 (3μg), prepared through the phenyl-Sepharose step, was subjected to SDS-PAGE. Protein standards of known molecular masses are indicated: β galactosidase ($M_r$=116,000); phosphorylase b ($M_r$=97,000); bovine serum albumin ($M_r$=66,000); ovalbumin ($M_r$=45,000); carbonic anhydrase ($M_r$=29,000).

At each step, a peak of proteasome stimulatory activity was observed. Because most of the endogenous Suc-Leu-Leu-Val-Tyr-AMC hydrolyzing activity was removed after the initial gel filtration step, the calculation required to identify the activator, described above, was not necessary for these remaining steps. Proteasome activation could not be assessed at preparative stages prior to the gel filtration step because of the high background from endogenous hydrolytic activity and possibly because of interference from other proteins present in these crude extracts. Therefore, estimates for the efficiency of this purification may be considerably underestimated. In any case, this purification scheme resulted in a single protein band with an apparent $M_A$=28,000 on SDS-PAGE (FIG. 5). This same protein band was coincident with the elution profiles of the proteasome activation at each stage of the purification, as judged by SDS-PAGE. Chromatography of the purified protein on Sephacryl S-200 indicated an apparent native molecular weight of approximately 180,000. During centrifugation through 10–40% glycerol gradients, the activator migrated coincidentally with an aldolase standard ($M_r$=158,000) (see FIG. 6A, FIG. 6B and FIG. 6C). Thus, the native activator may be a hexamer of a 28,000-dalton polypeptide. This new proteasome activator protein has been termed PA28.

The apparent subunit molecular weight of PA28 lies within the range of those of the proteasome subunits (2–6). Because all proteasome subunits examined thus far seem to be homologous (6–16), these data raise questions about the possible relationship between PA28 and the proteasome. In order to address this issue, the amino acid sequence data for PA28 was obtained. The N terminus of purified PA28 was blocked to automated Edman degradation. Therefore, PA28 was subjected to solid-phase tryptic digestion (6). The resulting peptides were isolated by reverse-phase high pressure liquid chromatography, and selected peptides were analyzed by automated Edman degradation. Five different peptides provided sequences of 10, 11, 16, 17, and 24 amino acids, respectively. Computer-aided comparison of these sequences with those in PIR and Swiss-Prot databases failed to identify significant similarities with any known protein. Thus, PA28 is a novel polypeptide.

Characterization of the Function of the PA28 Activator. The purified PA28 activator was tested for its ability to regulate the various hydrolytic activities of both the active and latent forms of the proteasome. Each of these proteasome forms displays three distinct hydrolytic activities, as characterized by the hydrolysis of different peptide substrates (1,2). These include: a "trypsin-like" activity, characterized by the hydrolysis of the substrate Z-Val-Leu-Arg-MNA and Z-Arg-Arg-MNA; a "chymotrypsin-like" activity, characterized by the hydrolysis of the substrate Z-Gly-Gly-Leu-AMC; and a peptidylglutamyl-peptide hydrolyzing activity, characterized by hydrolysis of the substrate Z-Leu-Leu-Glu-βNA. The hydrolysis of commonly used proteasome substrates, Suc-Leu-Leu-Val-Tyr-AMC and hippuryl-Phe-Ala-Ala-Phe-p-aminobenzoate have been alternatively ascribed to either the peptidylglutamyl-peptide hydrolyzing site (29) or the chymotrypsin-like site (16), and therefore the former was also included in the current analysis. The PA28 activated proteasome hydrolyzed Z-Arg-Arg-MNA at a rate of 42 units/µg where 1 unit is 1 nmol/min. The substrate concentration was 25 µM and the control level was at 2.6 units/µg. The active, but not the latent form of the proteasome also hydrolyzes large protein substrates such as casein and lysozyme to acid-soluble peptides, although the relationship of this activity to the peptide hydrolyzing activities is unclear (21). The present inventors systematically examined the effect of the PA28 activator on each of the substrates described above for each proteasome form over a range of substrate and activator concentrations. The results are shown in FIGS. 7A, 7B, 7C, 7D, 8A, 8B, 8C, 8D, 9A, 9B, 9C and 9D and Table 2.

some displays positive cooperativity, a feature not unexpected of a multisubunit enzyme. The substrate concentrations required for half-maximal reaction velocity ($K_{0.5}$, estimated from FIGS. 7 and 8) for the two proteasome forms for given substrates were similar, but the latent proteasome had higher maximal reaction velocities against these small synthetic peptide substrates than did the active proteasome. Thus, as shown previously, the characteristic feature of proteasome latency is an inability to hydrolyze large protein substrates (21). The PA28 activator greatly stimulated rates of hydrolysis of each peptide substrate by each proteasome form. Although this effect was demonstrable at all substrate concentrations, the maximal reaction velocity in the presence of PA28 was achieved at lower substrate concentrations than in its absence. This resulted in a shift of the velocity versus substrate concentration curves to the left and in a change in the shape of these curves from sigmoidal (in the absence of PA28) to hyperbolic (in the presence of PA28), suggesting that the activator functioned as a positive allosteric effector of the proteasome. In other words, the PA28 activator had the general effect of increasing the maximal reaction velocity and decreasing the apparent $K_{0.5}$ for these reactions (Table 2). The only exception to this general conclusion was the hydrolysis of Z-GlyGly-Leu-AMC, for which the activator increased the reaction velocity but had no effect on the apparent $K_{0.5}$. This substrate, however, was poorly soluble above concentrations of 50 µM, thus limiting any firm conclusions regarding the shape of the curve. At fixed substrate concentrations, the PA28 activator increased reaction velocity for the hydrolysis of each substrate by each proteasome form in a concentration-dependent manner

TABLE 2

EFFECT OF PA28 ON CATALYTIC PROPERTIES OF THE 20 S PROTEASOME[1]

|  | $V_{max}$ | | $K_{0.5}$ | |
| --- | --- | --- | --- | --- |
|  | Control | +PA28 | Control | +PA28 |
|  | units/µg | | µM | |
| Proteasome L | | | | |
| Z—Val—Leu—Arg—MNA | 20 | 105 | 35 | 7 |
| Z—Gly—Gly—Leu—AMC | 55 | 165 | 65 | 40 |
| Z—Leu—Leu—Glu—βNA | 300 | 675 | 125 | 60 |
| Suc—Leu—Leu—Val—Tyr—AMC | 50 | 1200 | 200 | 40 |
| [methyl-$^{14}$C]Casein | 1.5 | 1.5 | | |
| Proteasome A | | | | |
| Z—Val—Leu—Arg—MNA | 5.0 | 34 | 8 | 3 |
| Z—Gly—Gly—Leu—AMC | 4.5 | 19 | 30 | 30 |
| Z—Leu—Leu—Glu—βNA | 50 | 105 | 180 | 50 |
| Suc—Leu—Leu—Val—Tyr—AMC | 4.5 | 205 | 220 | 60 |
| [methyl-$^{14}$C]Casein | 125 | 130 | 2.4 | 2.5 |

[1]Purified 20 S proteasome (latent, L, or active, A, from bovine red blood cells) was assayed with the indicated substrates in the presence and absence of PA28 under the conditions described in FIGS. 7 and 8. $V_{max}$ (maximal reaction velocity) and $K_{0.5}$ (substrate concentration required for half-maximal reaction velocity) were estimated from the data shown in FIGS. 7 and 8.

In the absence of PA28, the proteasome displayed complex kinetic features; plots of reaction velocity versus substrate concentration for both the active and latent proteasome forms produced sigmoidal curves, which varied in degree among the different substrates. Thus, double-reciprocal plots of these data yielded concave curves that prevented graphical determination of $V_{max}$ and $K_m$ values. Such kinetic features, demonstrated previously for the Z-Leu-Leu-Glu-substrate (30,31), indicate that the proteasome (FIG. 9A, 9B, 9C and 9D). The magnitude of the effect differed among the various substrates, ranging from over 200-fold for Suc-Leu-Leu-Val-Tyr-AMC to 6-fold for Z-Gly-Gly-Leu-AMC. Proteasome regulation by PA28 was achieved at nanomolar concentrations of each protein, suggesting that PA28 acted as a tight-binding effector (FIGS. 7A, 7B, 7C, 7D, 8A, 8B, 8C, 8D, 9A, 9B, 9C, and 9D). The data in FIGS. 9A, 9B, 9C and 9D also demonstrate that half-maximal increases in proteasome activity occurred at molar ratios of protease to PA28 of approximately 1:1. Preincubation of PA28 with the proteasome for various times prior to assay had no effect on any of these results, making it unlikely that PA28 acted catalytically to modify proteasome function.

Despite the large effects of PA28 on the peptidase activities of the proteasome, no effect was detected on proteasome-catalyzed degradation of protein substrates such as casein, lysozyme, or albumin, either by the active proteasome, which has high proteolytic activity, or by latent proteasome, which has no activity toward protein substrates. This result was not influenced by a number of variations in assay conditions (e.g. pH, temperature, and substrate concentrations) or by the presence of potential proteasome regulators such as ATP or ubiquitin (Table 2). These results provide a distinction between the peptidase activities and the protein hydrolyzing activities of the proteasome. Neither the binding of PA28 to the proteasome nor the PA28 stimulation of the proteasome requires ATP. This observation distinguishes PA28 from partially purified proteasome regulatory proteins previously described in the literature (26, 48).

The PA28 activator appeared to be specific for the proteasome and had no effect on any other protease tested, including trypsin and chymotrypsin. Because assays of these enzymes were conducted with some of the same synthetic peptide substrates employed for the proteasome, it is unlikely that the PA28-increased peptidase activities of the proteasome resulted artifactually by some unknown interaction of PA28 with these substrates or their fluorescent products. Furthermore, no detectable peptidase activity was observed in the purified PA28 activator samples, even when they were assayed for extended periods of time at concentrations over 50 times greater than those used for maximal proteasome activation.

Figure 6A:
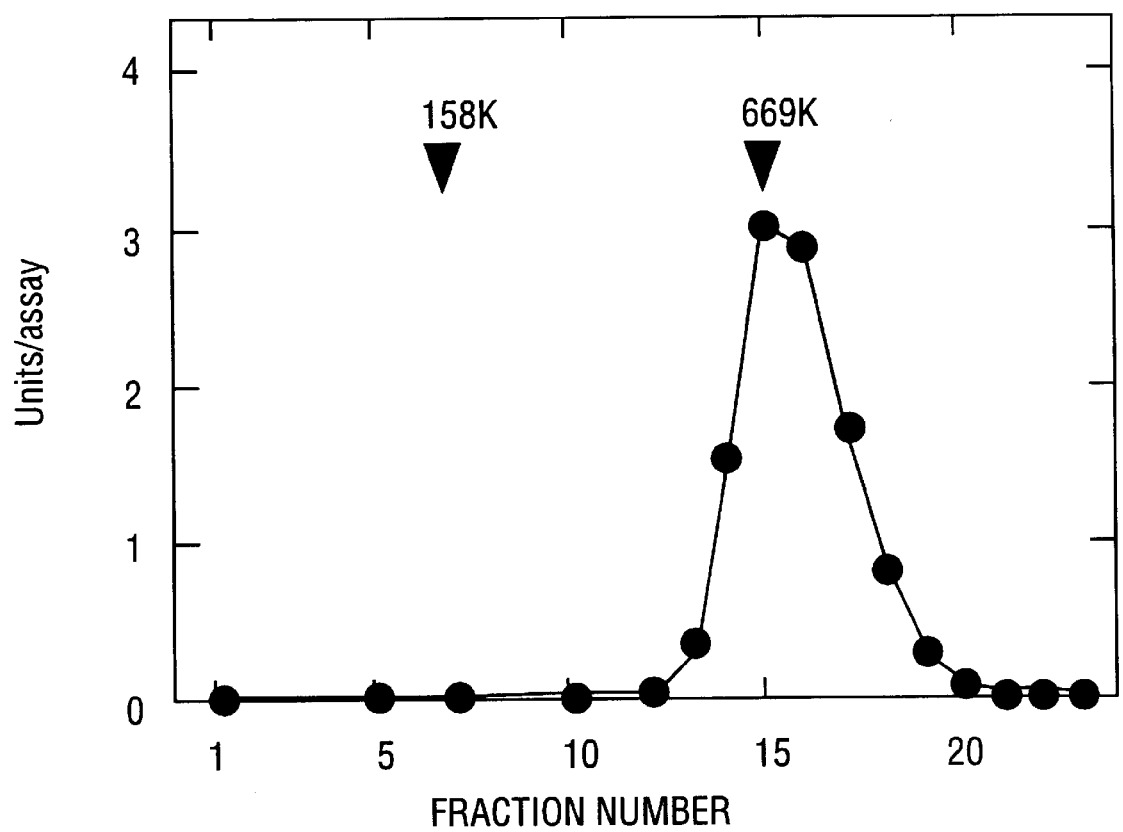
FIG. 6A, FIG. 6B and FIG. 6C show glycerol density gradient centrifugation of PA28 and PA28 proteasome complexes. All panels represent centrifugation conditions described under "Materials and Methods.
Figure 6B:
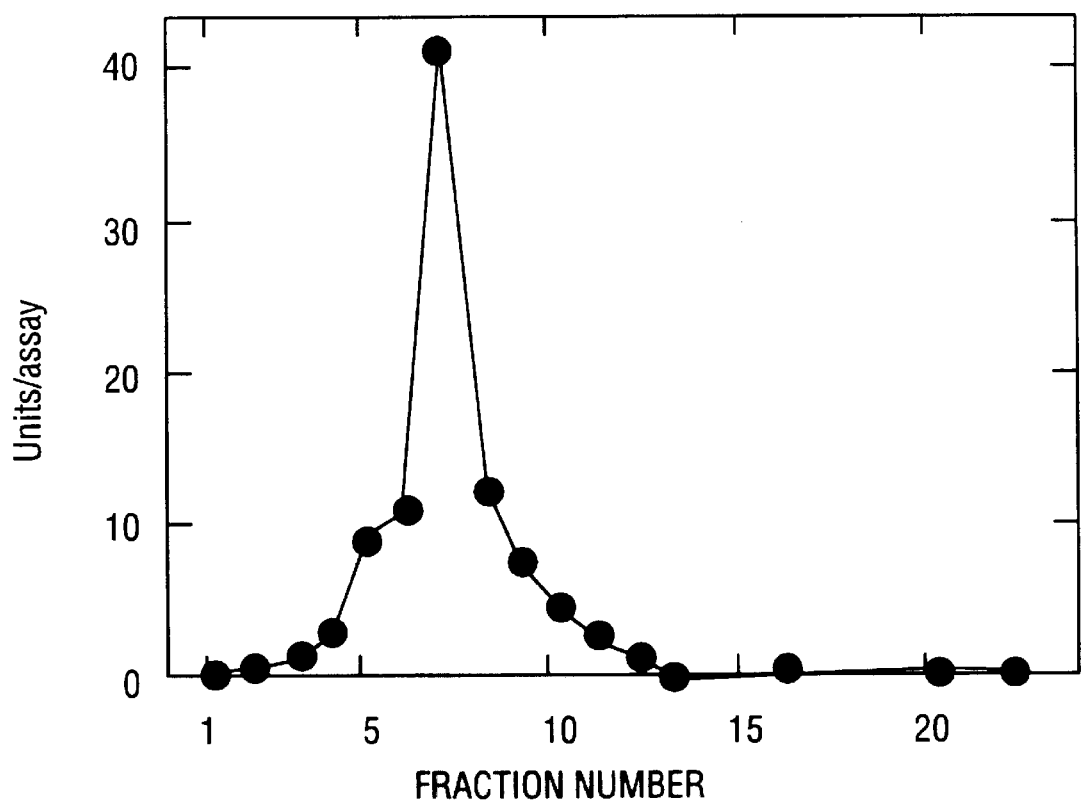
Figure 6C:
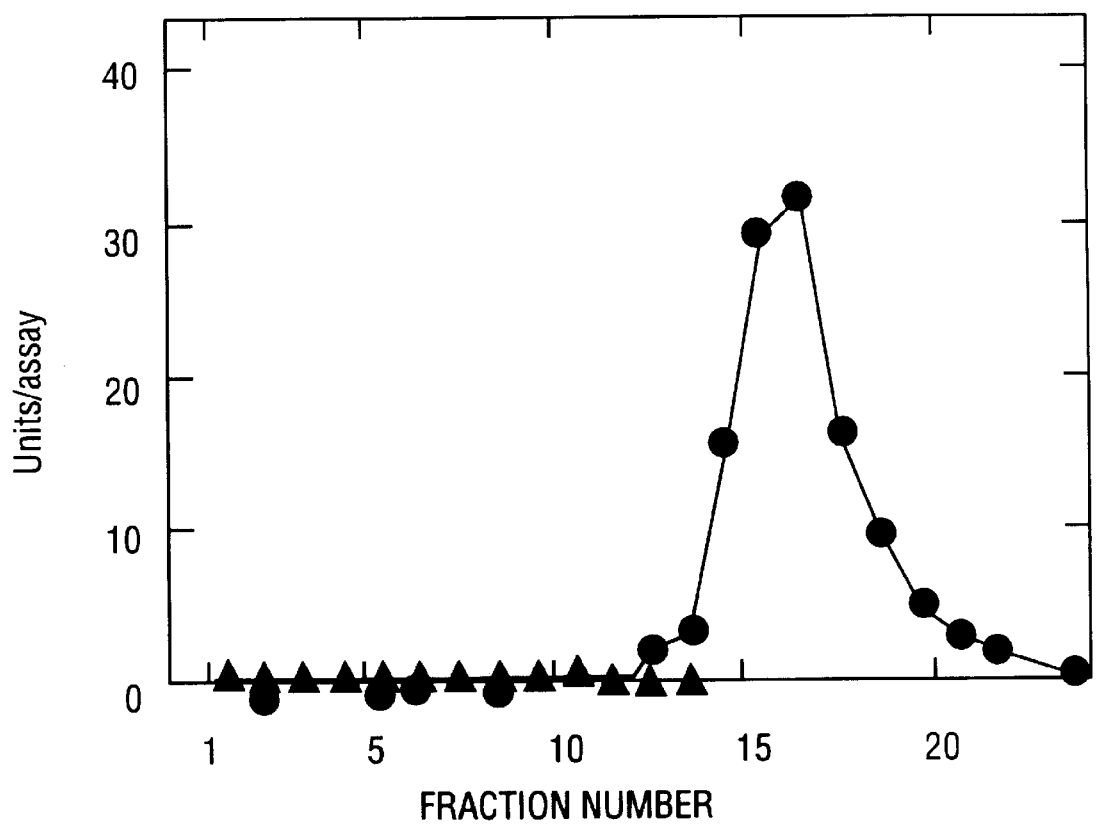
Figure 7A:
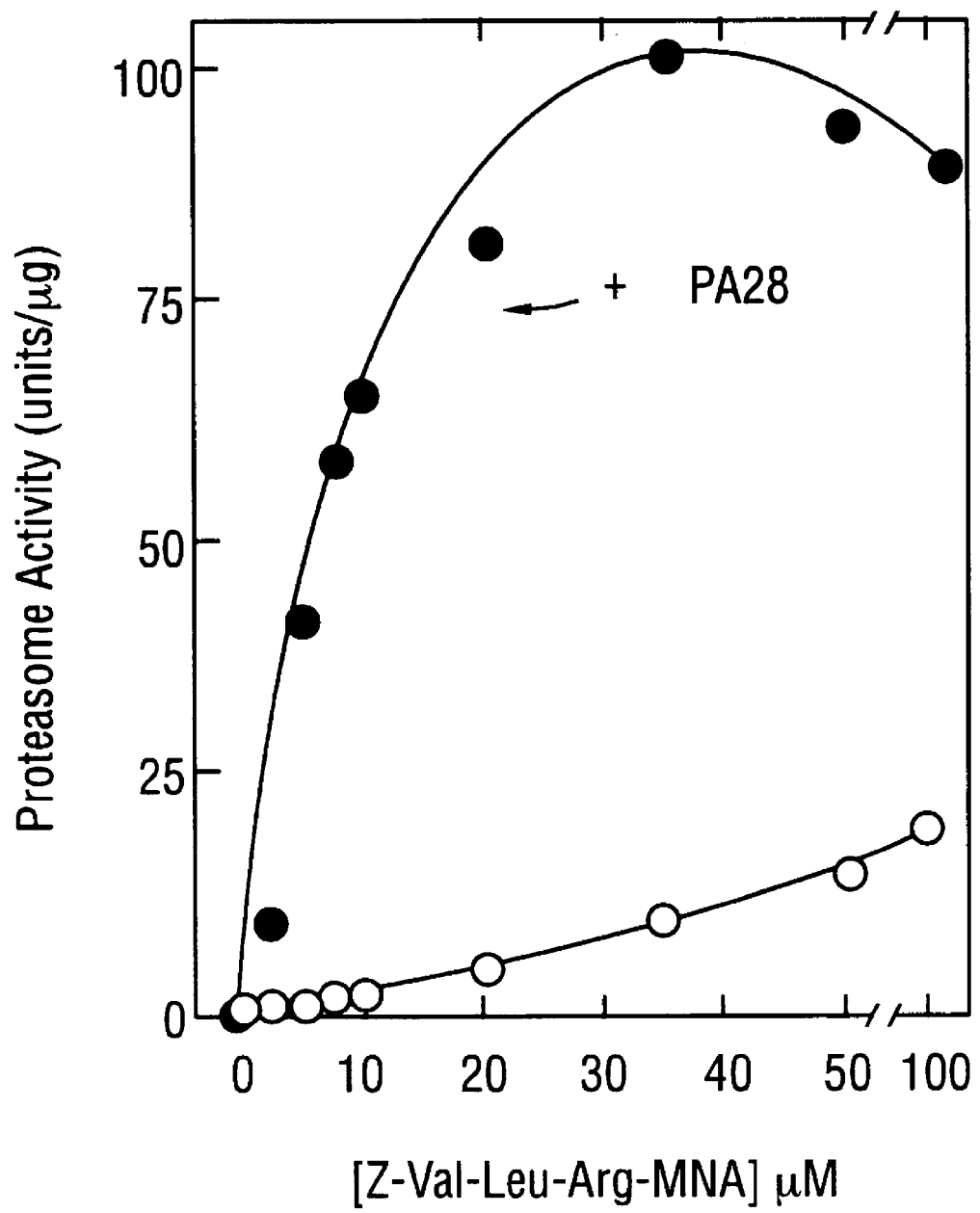
FIG. 7A, FIG. 7B, FIG. 7C and FIG. 7D show the effect of PA28 on substrate versus velocity plots for latent 20 S proteasome. Latent 20 S proteasome was assayed with the indicated substrates in the presence (●) and absence (○) of PA28. Similar results were obtained in two independent experiments.
Figure 7B:
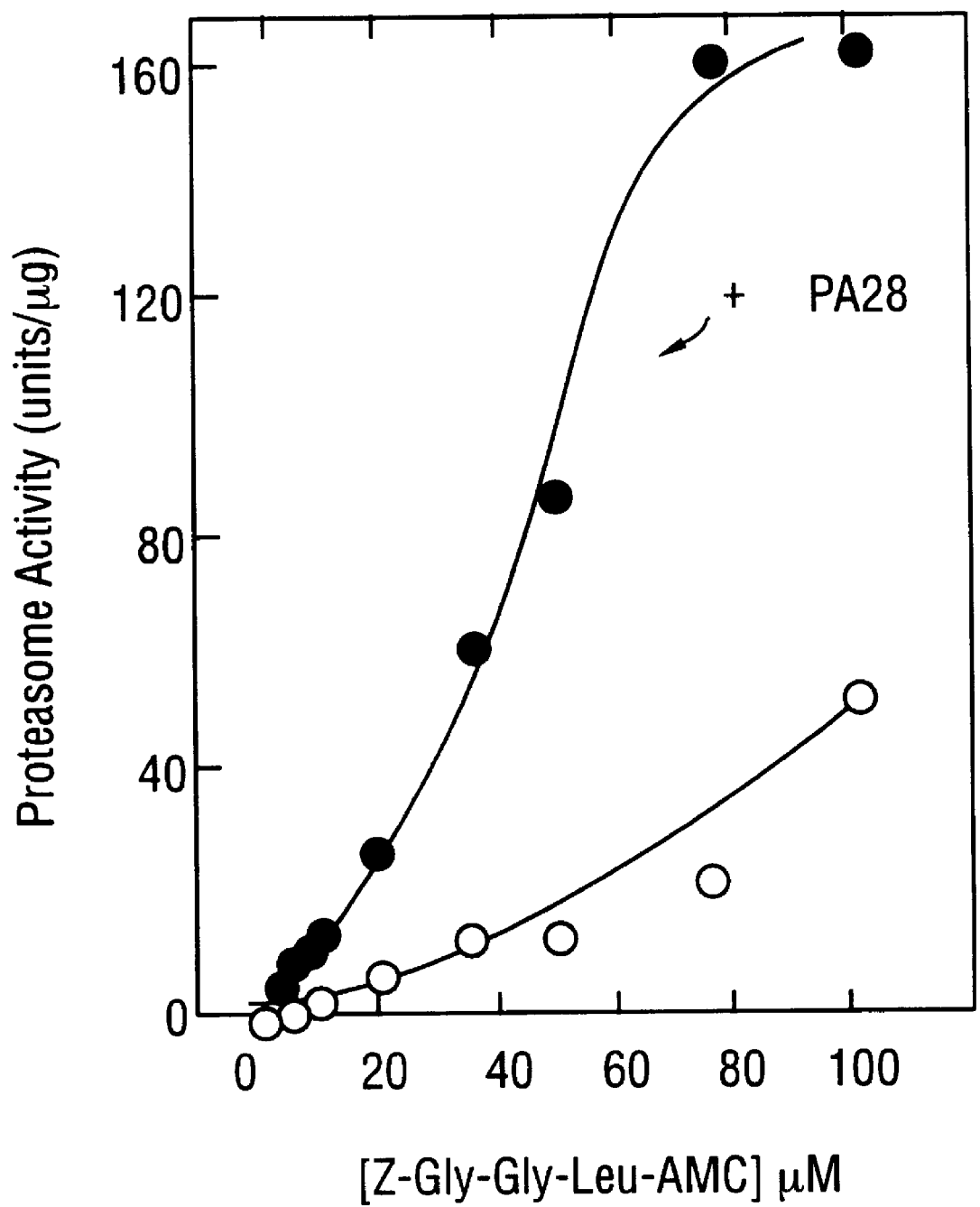
Figure 7C:
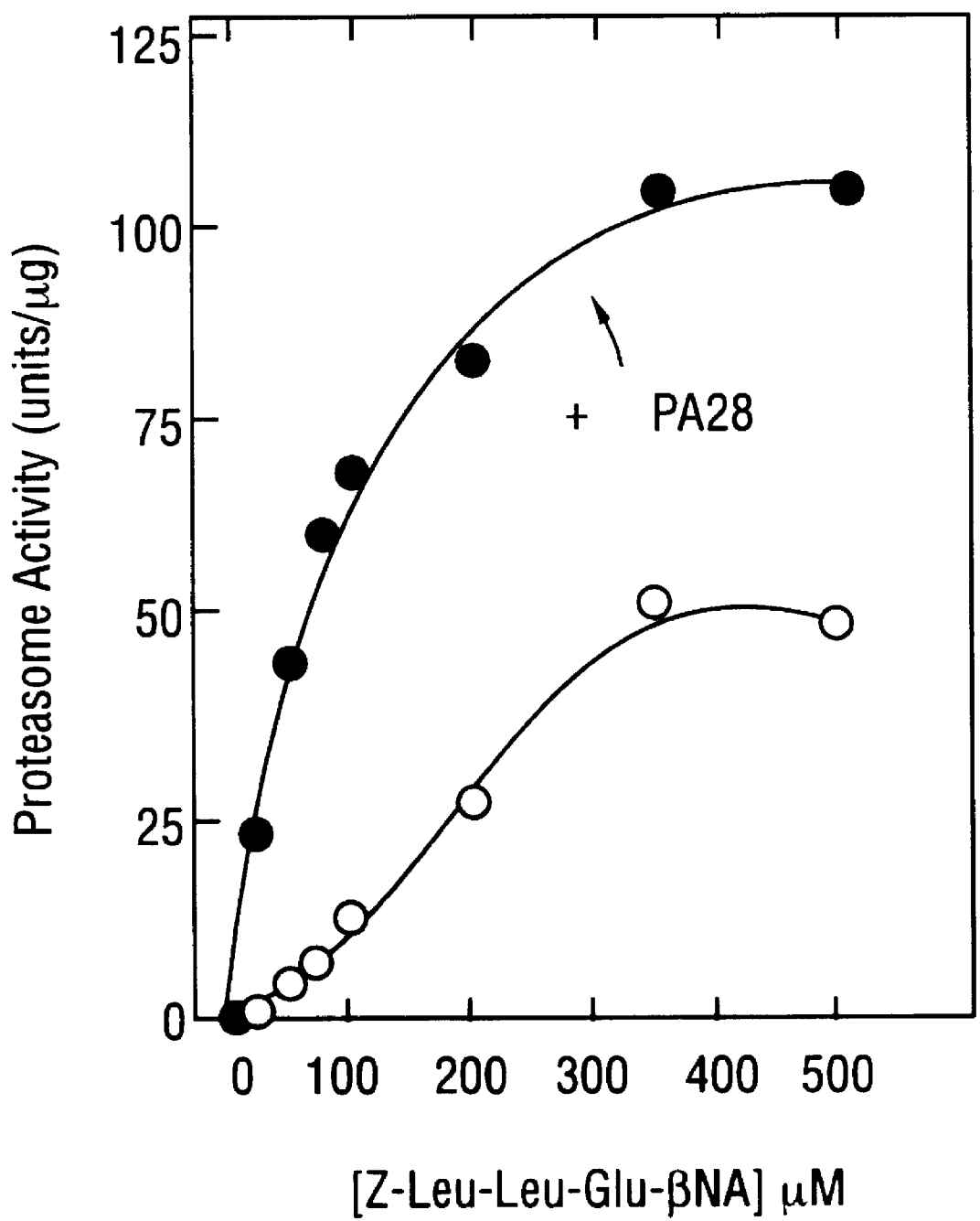
Figure 7D:
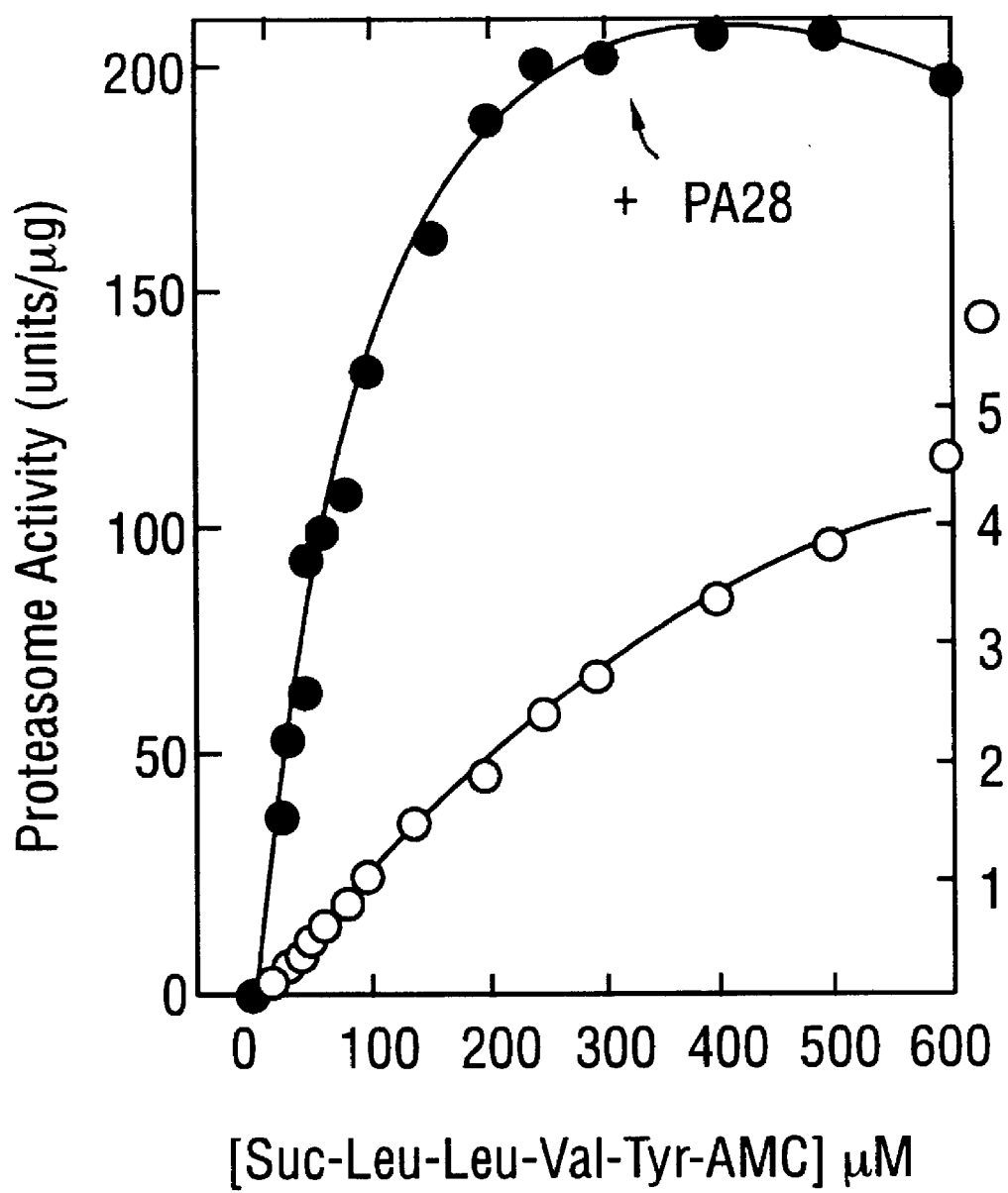
Figure 8A:
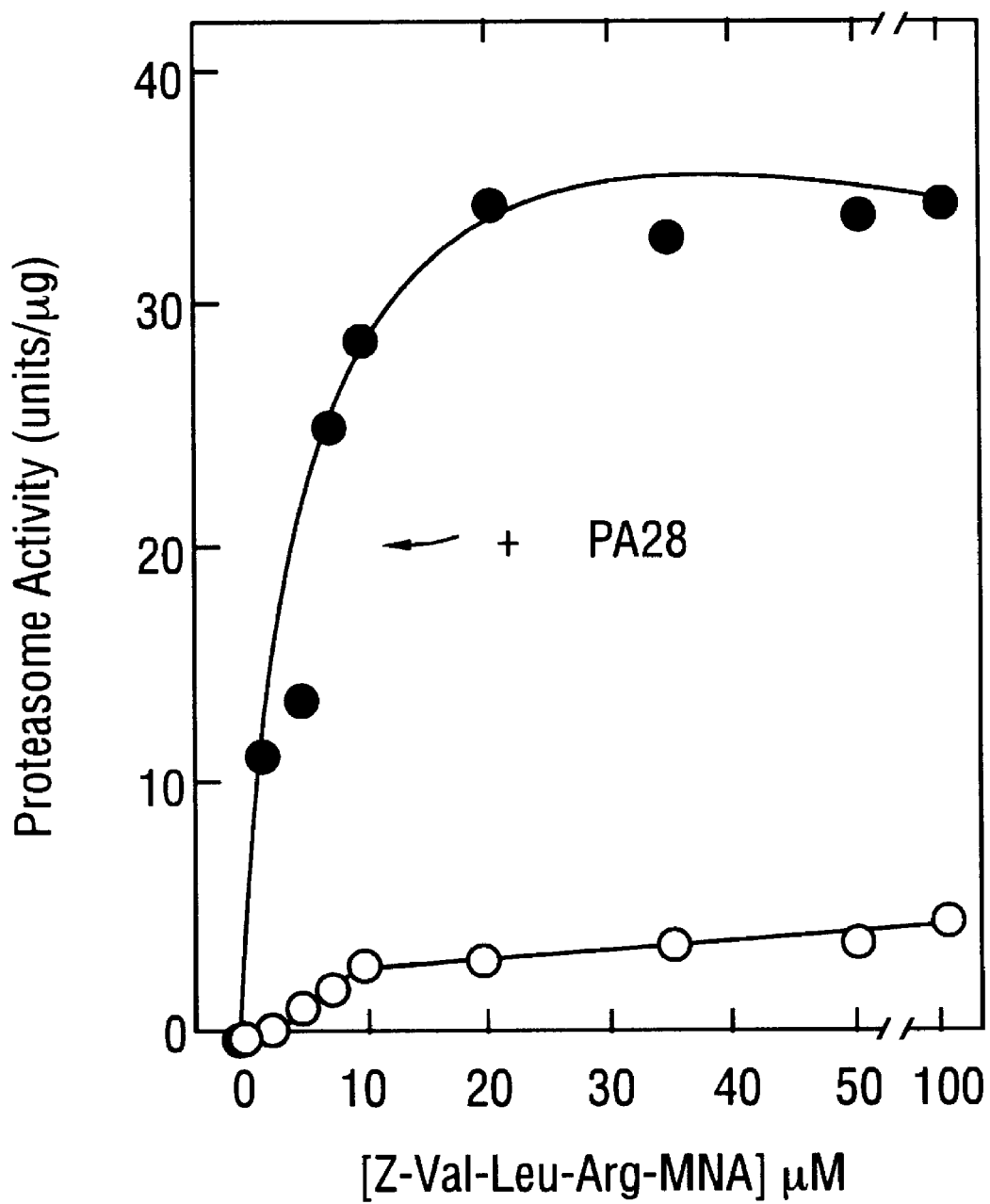
FIG. 8A, FIG. 8B, FIG. 8C and FIG. 8D show the effect of PA28 on substrate versus velocity plots for active 20 S proteasome. Active 20 S proteasome was assayed with the indicated substrates in the presence (●) and absence (○) of PA28. Similar results were obtained in three independent experiments.
Figure 8B:
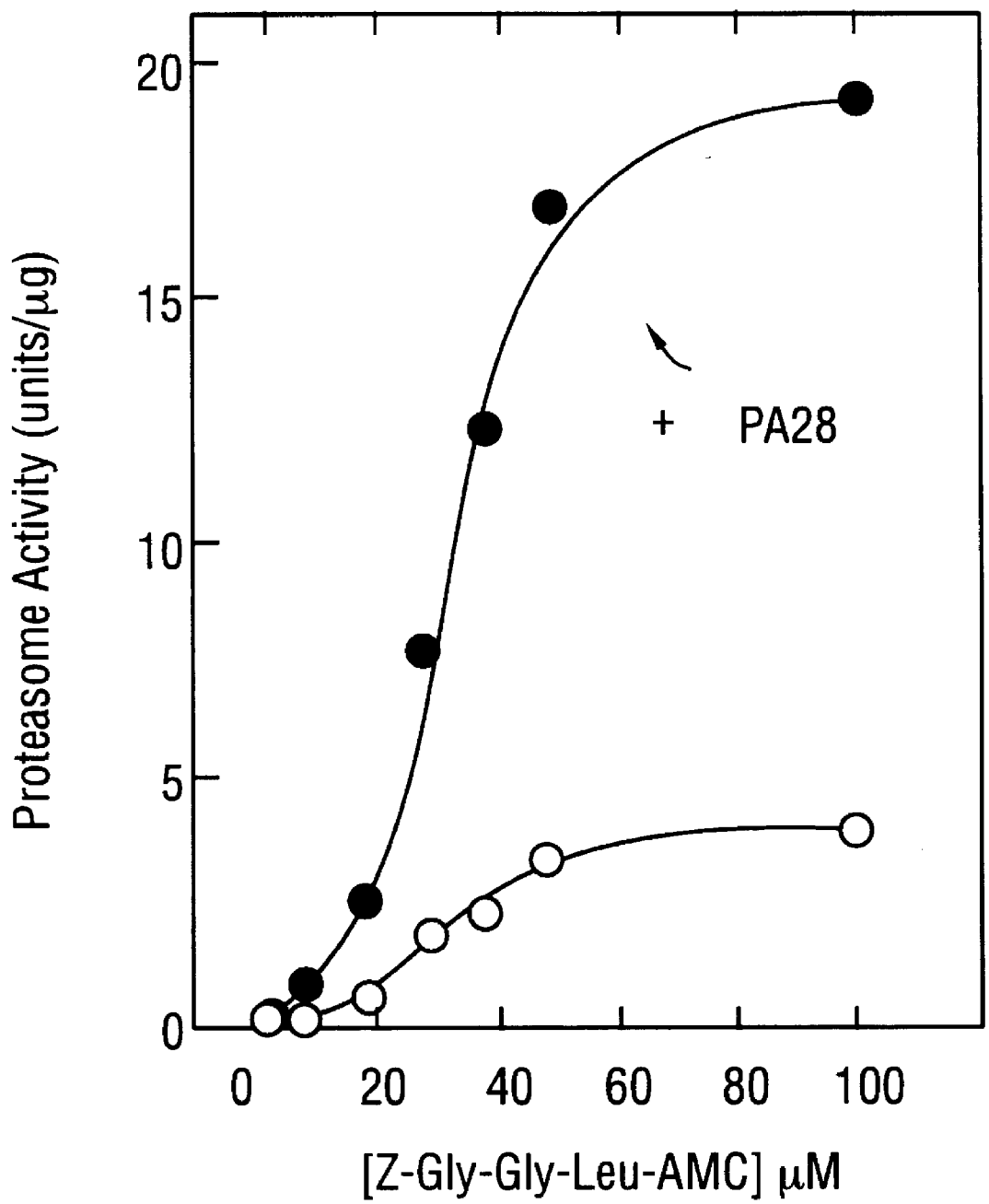
Figure 8C:
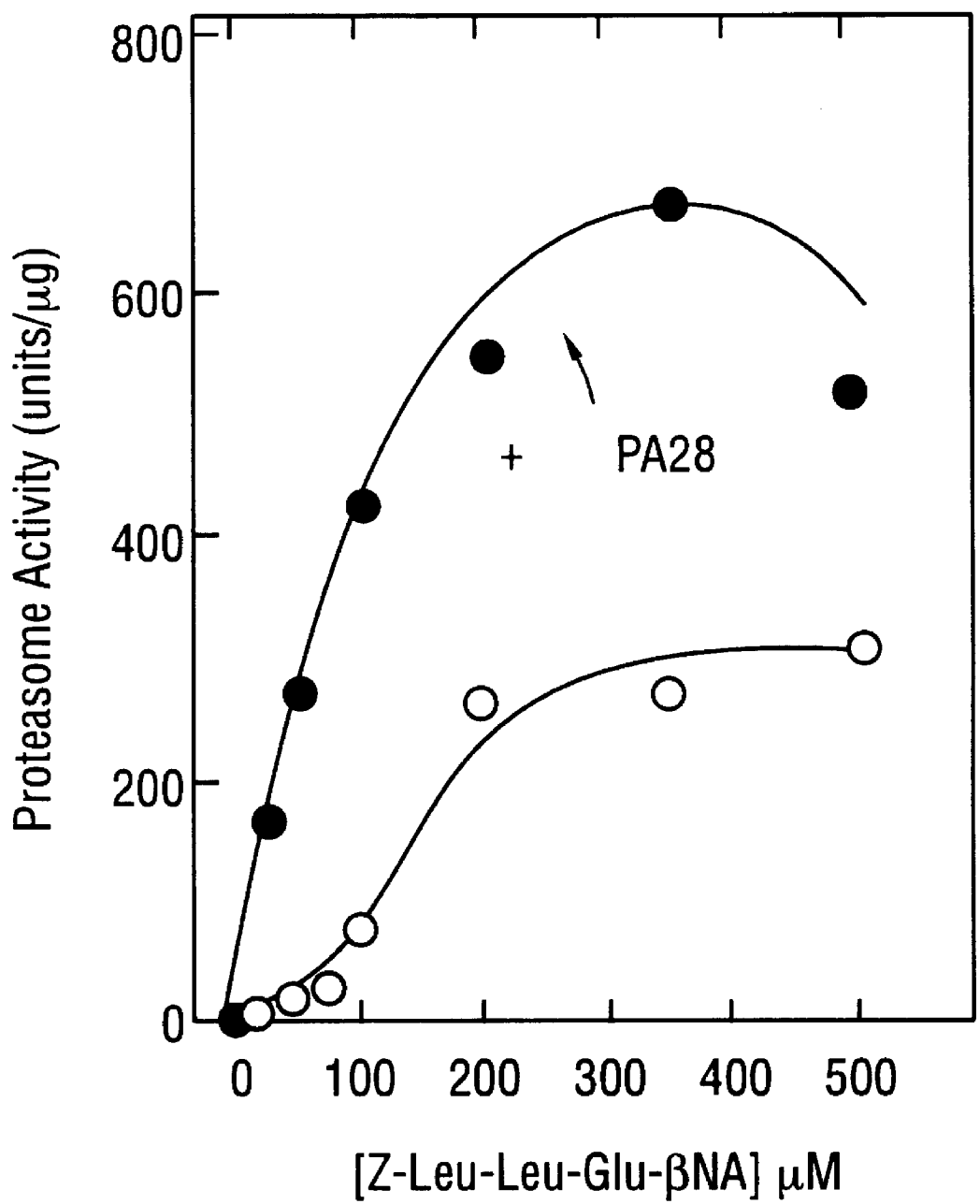
Figure 8D:
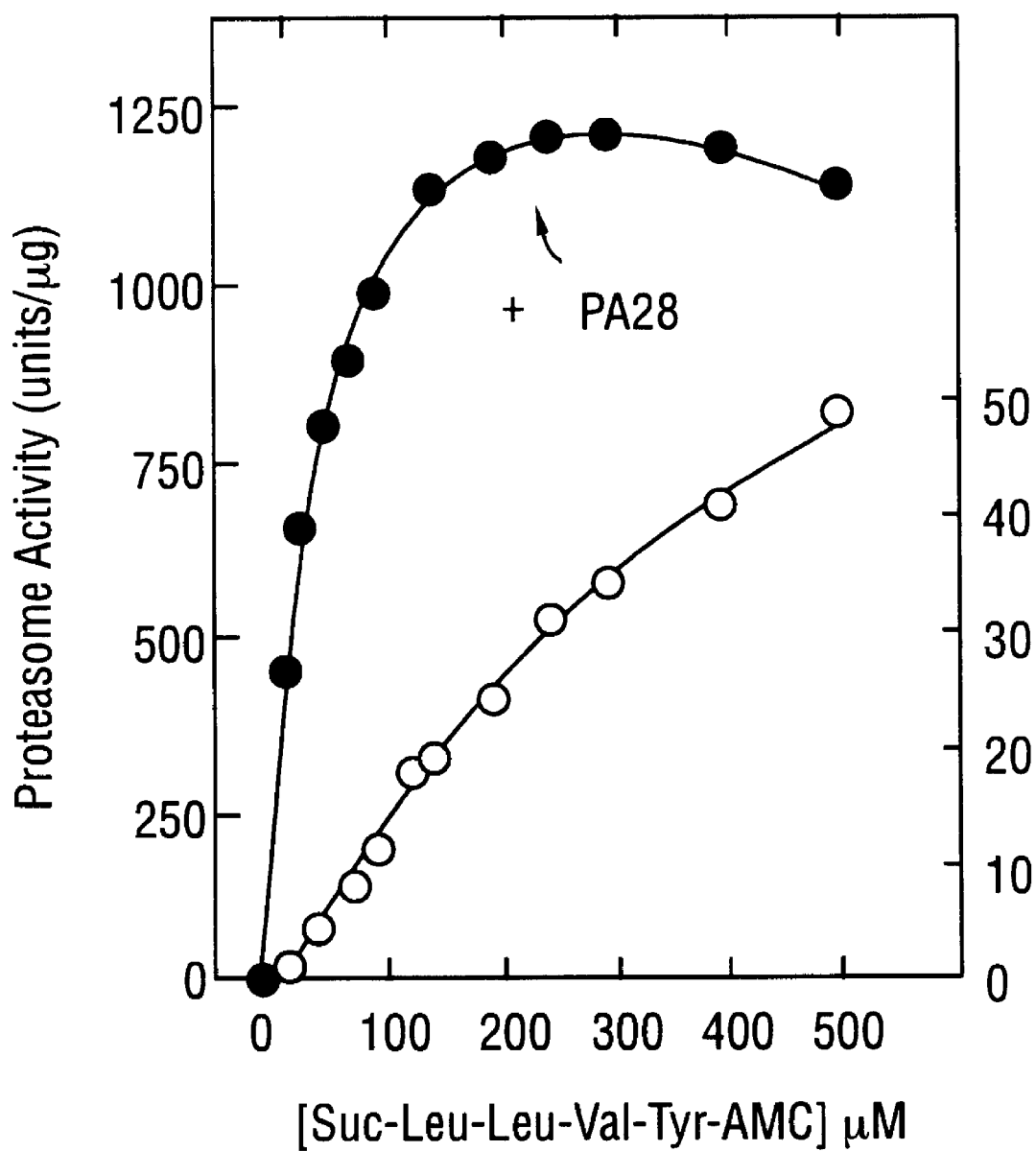
Figure 9A:
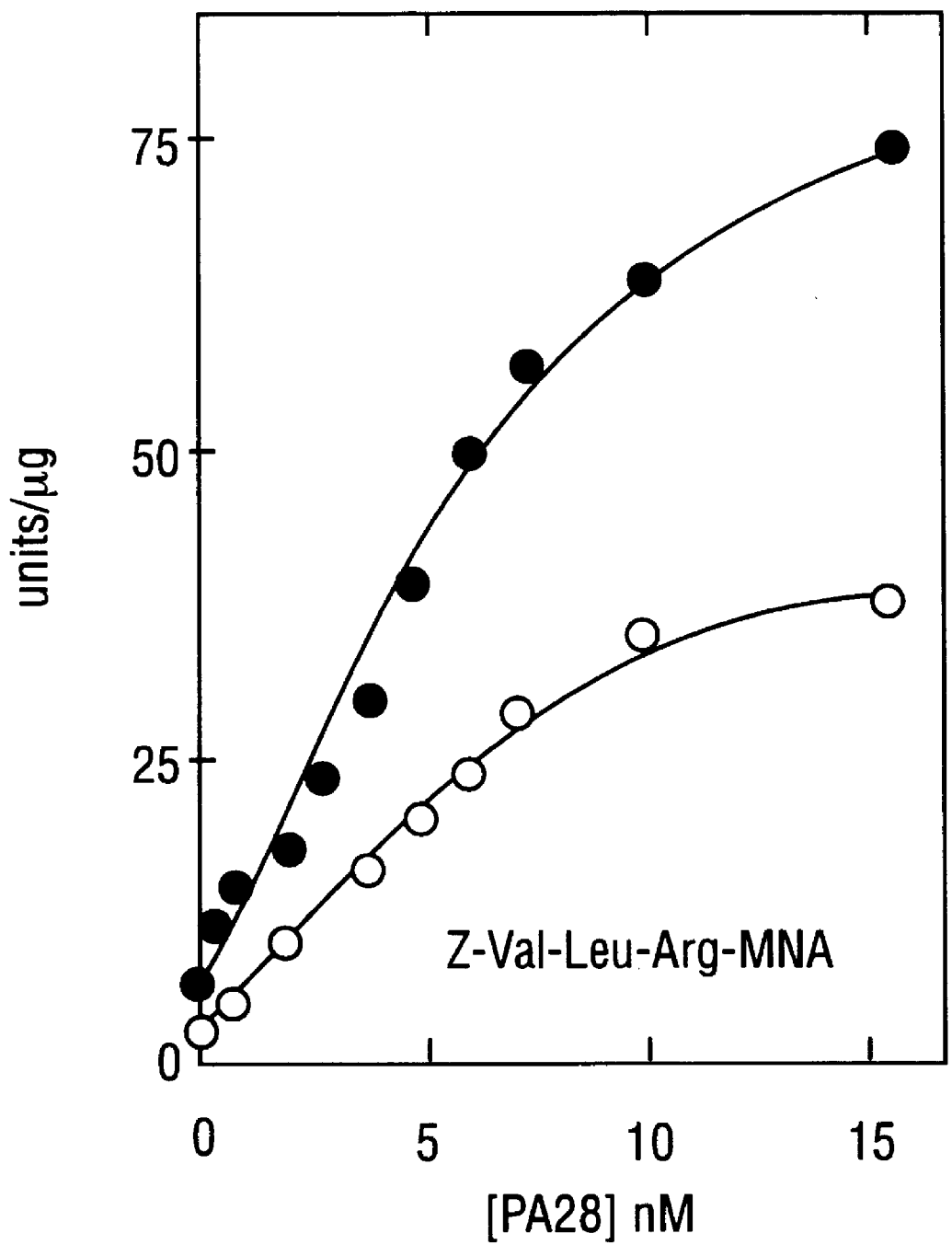
FIG. 9A, FIG. 9B, FIG. 9C and FIG. 9D show the effect of PA28 concentration on hydrolytic activities of latent (●) and active (○) 20 S proteasomes. Similar results were obtained in three independent experiments.
Figure 9B:
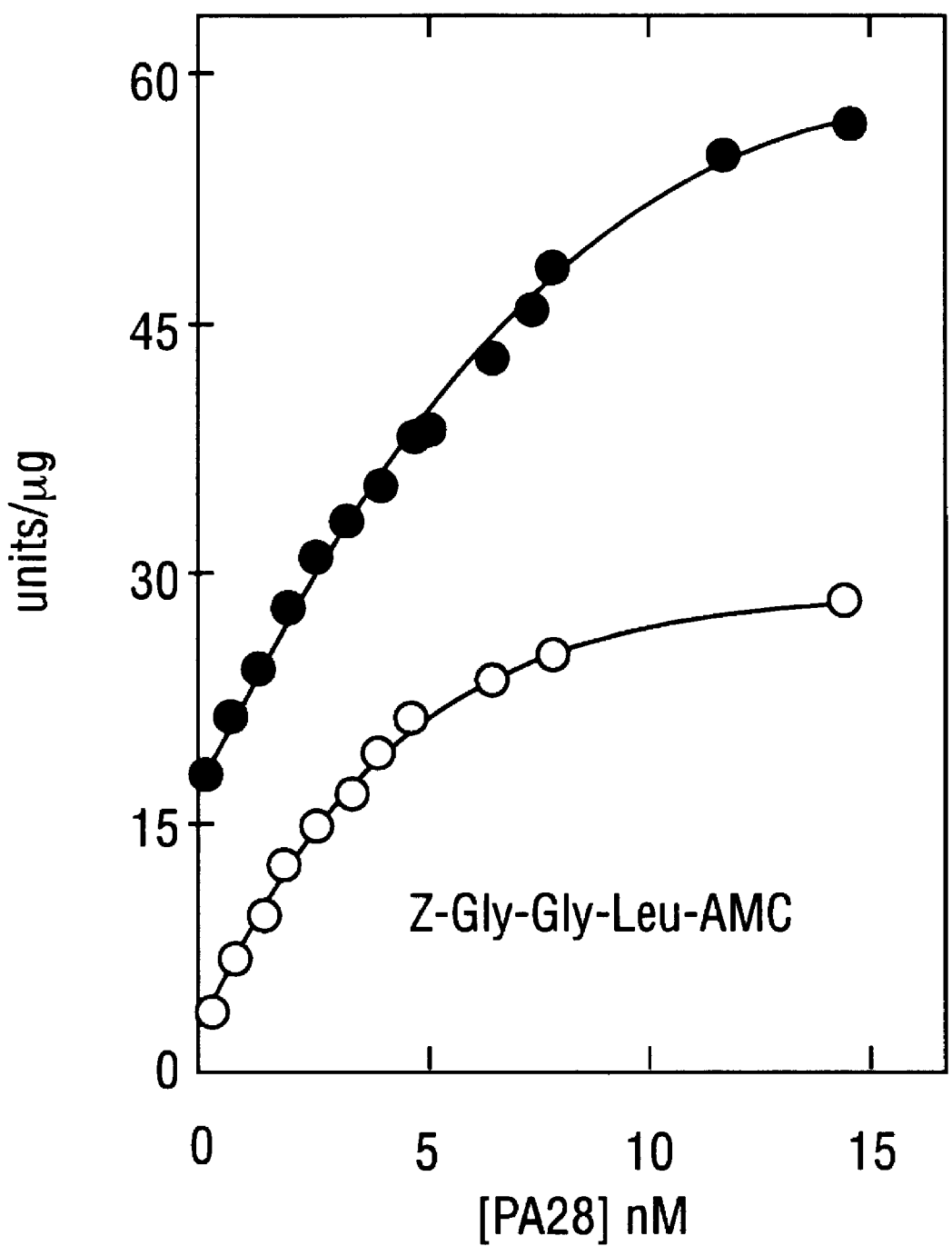
Figure 9C:
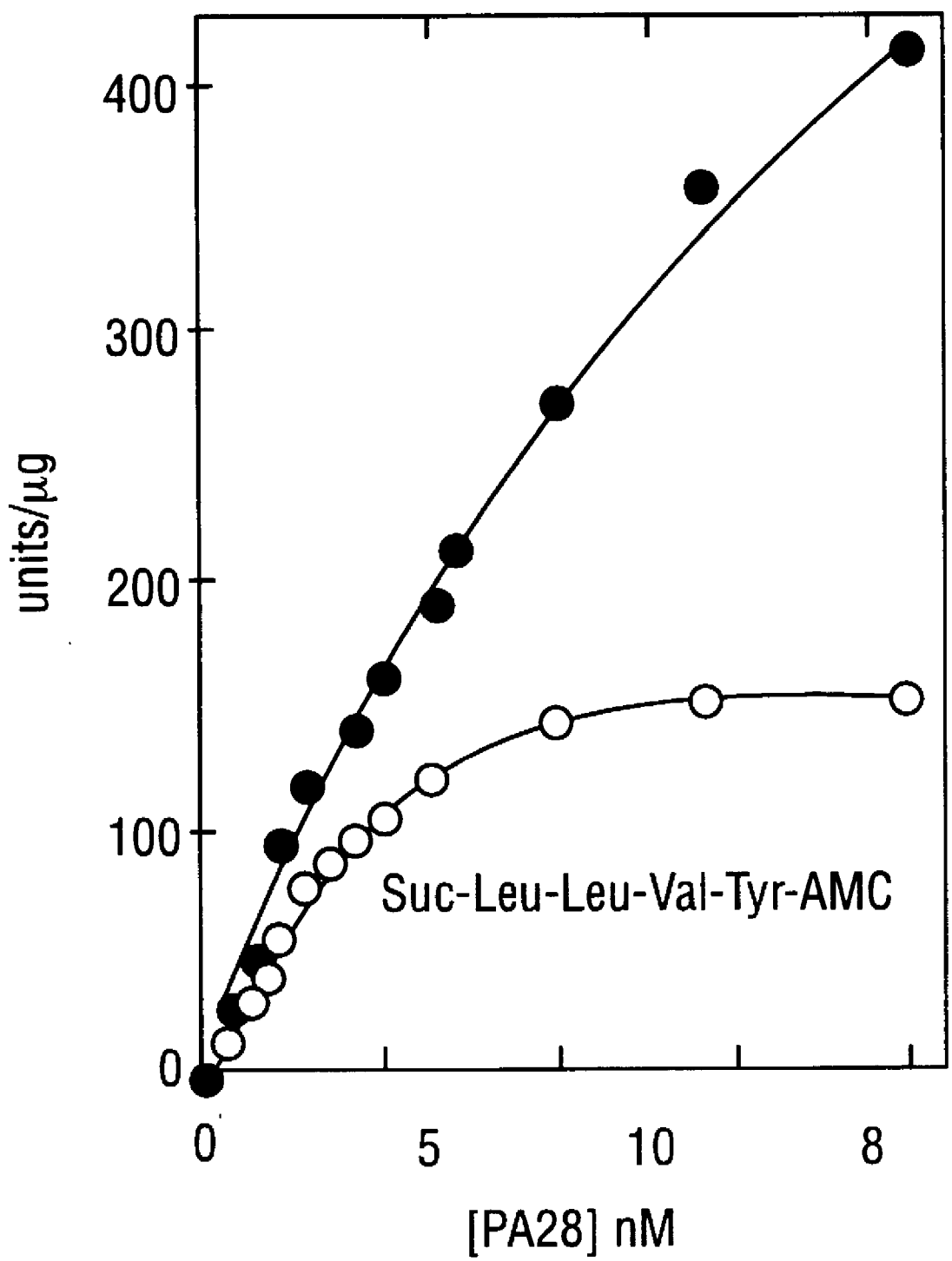
Figure 9D:
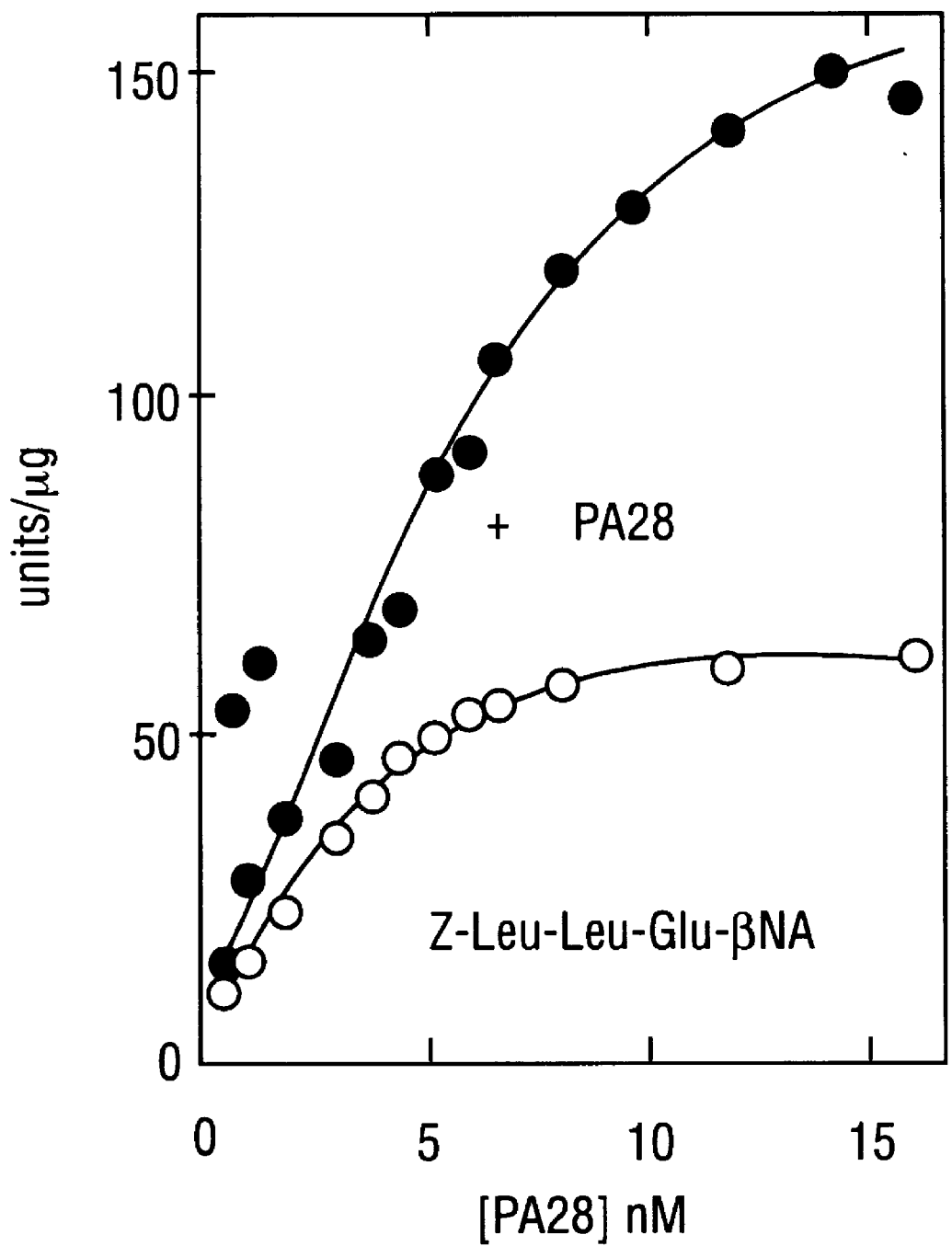

Evidence for a direct interaction between the proteasome and PA28 was obtained by glycerol density gradient centrifugation. Purified active proteasome migrated to a position corresponding to approximately 20 S in glycerol gradients and was clearly distinct from the purified PA28 (FIG. 6A and 6B). However, when the two proteins were preincubated briefly and then centrifuged, the proteasome was recovered in a highly activated state (FIG. 6C). When the preincubation contained a 5-fold molar excess of proteasome, no detectable PA28 activity (FIG. 6C) or protein (judged by SDS-PAGE) was recovered in the gradient fractions expected to contain free PA28. However, when the preincubation contained a 5-fold molar excess of PA28, both activated proteasome and free PA28 were detected in the gradient fractions. These results indicate that the observed proteasome activation most likely resulted from the binding of PA28 to the proteasome and the comigration of the complexed proteins in the gradient. Similar results with glycerol density gradient centrifugation were obtained with the latent proteasome.

Identification of PA28 from Other Sources. All of the data presented in this example were obtained with PA28 from bovine red blood cells. PA28 was also identified in rabbit and bovine heart and was purified from the latter source. Indistinguishable results in terms of the physical and functional properties of PA28 were obtained using the bovine heart protein.

EXAMPLE II

A PA28 Inactivating Protein

The present example shows that PA28 is widely distributed, describes the basis for the lack of detectable PA28 activity in some tissue extracts and indicates an important role of the carboxyl terminus of PA28 in its action on the proteasome. A PA28 inactivating protein is described.

Materials and Methods

Purification of PA28 and the proteasome from bovine red blood cells. PA28 and the proteasome were purified from bovine red blood cells as described in Example I and in reference 21.

Assays for proteasome and PA28 activities. PA28 and proteasome activities were measured as described in Example I. The proteasome was assayed by measuring its hydrolysis of synthetic fluorogenic peptides: Suc-Leu-Leu-Val-Tyr-AMC; Z-ValLeu-Arg-MNA; Z-Leu-Leu-Glu-βNA; or Z-Gly-Gly-Leu-AMC, at pH 8.0, 30° C. One unit of activity is defined as the change in concentration of fluorescent product of 1.0 nM/min. under standard assay conditions (see Example I). The activity of PA28 was measured by its activation of the proteasome in these same assays. One unit of PA28 activity is defined as the increase of 1.0 unit of proteasome activity under the standard assay conditions.

Preparation of antibodies against PA28. Polyclonal antibodies against PA28 from bovine red blood cells were prepared in rabbits. Purified PA28 was subjected to SDS-PAGE and the isolated protein was visualized by briefly soaking the gel in an ice-cold solution of 150 mM KCl. The region of the gel containing the PA28 was isolated and used for antigen injections; small sections of gel were mixed with equal volumes of phosphate-buffered saline and Freund's adjuvant, homogenized vigorously with a Polytron homogenizer and then injected subcutaneously. The initial injections contained 100 μg of PA28 per rabbit; subsequent injections at approximately six week intervals contained 50 μg of PA28 per rabbit. Sera were collected ten days after each injection.

Immunoblotting and electrophoretic methods. Immunoblotting and SDS-PAGE were performed as described (21).

Assay for PA28-inactivating activity. The inactivation of PA28 was assessed by measuring residual PA28 activity after preincubation of purified PA28 with the inactivating protein. The preincubation contained purified bovine red blood cell PA28 (0.2 μg), 100 mM MES buffer, pH 5.2, 2 mM DTT, and inactivating protein or other factors, as described in this example, in a final volume of 15 μl. After preincubation at 300 for 10 min., the reaction was stopped by addition of 1.0 ml of a solution containing 50 mM Trios-HCl, pH 8.0, 1 mM DTT, and 50 μM Suc-LeuLeu-Val-Tyr-AMC (or other proteasome substrate). The activity of the PA28 in this solution was determined by addition of 0.8 μg of purified proteasome, as described in Example I. One unit of PA28-inactivating activity is defined as the inhibition of one unit of PA28 activity. The peptidase activity of the PA28-inactivating protein was also measured directly using various synthetic peptide substrates in assays similar to those described for the proteasome. The assays consisted of 50 mM MES buffer, pH 5.2, 1 mM DTT, 50 μM substrate, and 50 μl of column fractions in a final volume of 1.0 ml. Reactions were carried out at 30° C. and the release of free MNA (or other reporter group) was monitored directly by fluorescence. 1.0 unit of activity is defined as the increase in product concentration of 1.0 nM/min.

Purification of a protein that inactivates PA28. Bovine livers were obtained at a slaughterhouse and cooled on ice. An extract from partially purified lysosomes was prepared. For a given preparation, a 200 g portion of liver, freed of connective tissue, was minced in ice-cold 0.25M sucrose and homogenized with 4 volumes of 0.25M sucrose in a Dounce homogenizer. The homogenate was centrifuged at 600×g for 10 min. The supernatant was recentrifuged at 3,300×g for 10 min. The resulting supernatant was centrifuged at 16,300×g for 20 min. The pellet was gently resuspended in 50 ml of 0.3M sucrose and then centrifuged at 9,500×g for 10 min. The resulting pellet was homogenized in 100 ml of a buffer consisting of 5 mM potassium phosphate, pH 7.6, 1 mM DTT, and centrifuged at 30,000×g for 45 min. The supernatant was dialyzed for 16 hrs against the phosphate buffer.

Figure 13A:
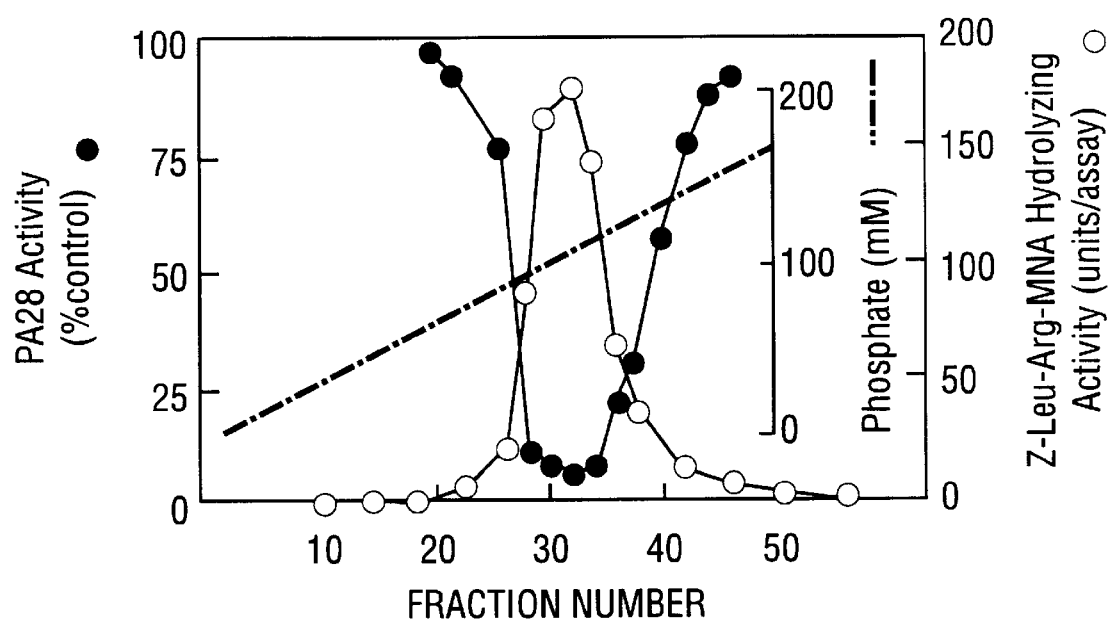
FIG. 13A, FIG. 13B and FIG. 13C show the purification of PA28-inactivating protein. A lysate of partially purified lysosomes from bovine liver was subjected to chromatography on hydroxylapatite (FIG. 13A), DEAE-Fractogel (FIG. 13B), and gel filtration by Sephacryl S-100 (FIG. 13C). The column fractions were assayed for the ability to inactivate PA28 (●) and for the hydrolysis of the synthetic peptide Z-Leu-Arg-MNA (○).

The soluble lysosomal extract was applied to a column containing 10 g of hydroxylapatite. The bound proteins were eluted with 320 ml of a linear phosphate gradient (5–200 mM) composed of the phosphate buffer. Five µl samples of the 5 ml column fractions were assayed for the ability to inactivate purified PA28 by the assay described above. The data are expressed as a percentage of the untreated PA28 activity. PA28-inactivating activity was identified in the eluted column fractions as a homogeneous peak at a position corresponding to approximately 100 mM phosphate. The column fractions were also assayed for protease and peptidase activities against a variety of substrates. Although numerous hydrolytic activities were identified, one of these, hydrolysis of the synthetic peptide Z-Leu-Arg-MNA, showed an elution profile that was coincident with the profile of the PA28-inactivating activity (FIG. 13A).

Figure 13B:
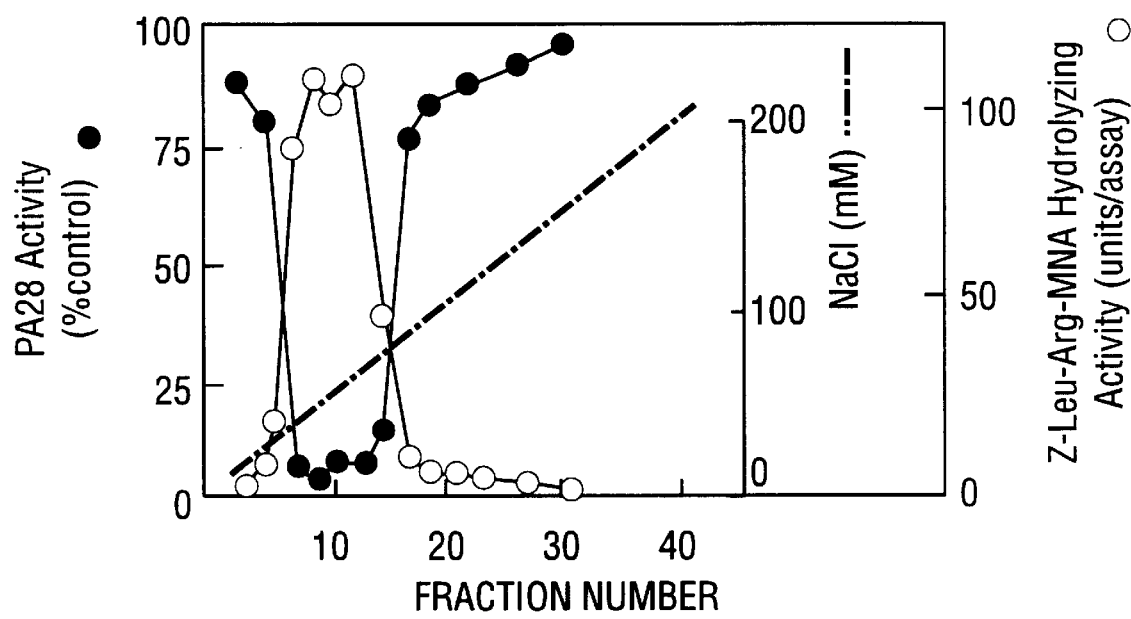

Fractions 28–38 from the hydroxylapatite column were pooled and dialyzed against a buffer containing 20 mM Tris-HCl, pH 7.6, 20 mM NaCl, 1 mM EDTA and 5 mM β-mercaptoethanol. The dialyzed sample was applied to a 13×1.7 cm column of DEAE-Fractogel (EM Separations) equilibrated with the same buffer. The bound proteins were eluted with 200 ml of a linear gradient of NaCl (20–200 mM) prepared in the column buffer. Samples of the 5 ml fractions were assayed for both PA28-inactivating activity and Z-Leu-Arg-MNA hydrolyzing activity. Each activity bound to the ion-exchange resin and eluted coincidently at a position corresponding to approximately 50 mM NaCl (FIG. 13B).

Figure 13C:
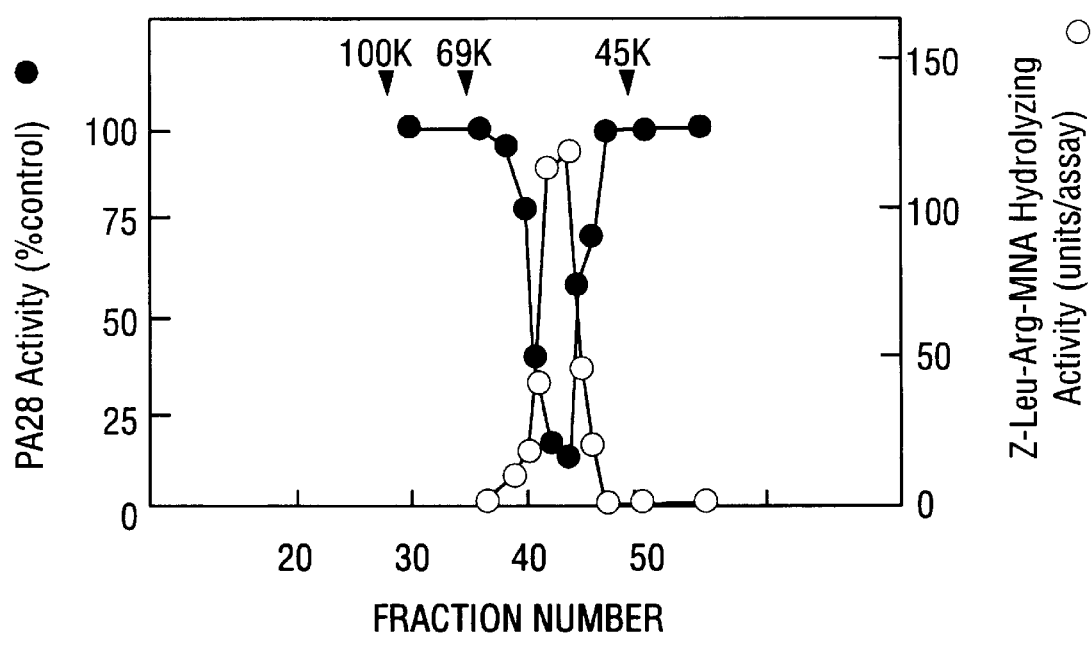

Fractions 8–12 from the DEAE-Fractogel column were pooled and dialyzed against 50 mM sodium acetate buffer, pH 5.5. The dialyzed sample was concentrated to a final volume of 3 ml and applied to a column of Sephacryl S-100 (50×2.5 cm), equilibrated with 50 mM sodium acetate, pH 5.5, 100 mM NaCl. Samples of the 3.5 ml fractions were assayed for PA28-inactivating activity and for Z-Leu-Arg-MNA hydrolyzing activity. These activities eluted coincidently as sharp, homogeneous peaks at a position corresponding to an apparent molecular weight of 50,000 (FIG. 13C). The coincident elution of these two activities on three different chromatographic columns suggests that they are accounted for by the same enzyme. Fractions 40–44 from the Sephacryl column were pooled, concentrated, and stored in column buffer containing 20% glycerol at −70° C. for further characterization.

Results and Discussion

Figure 10:
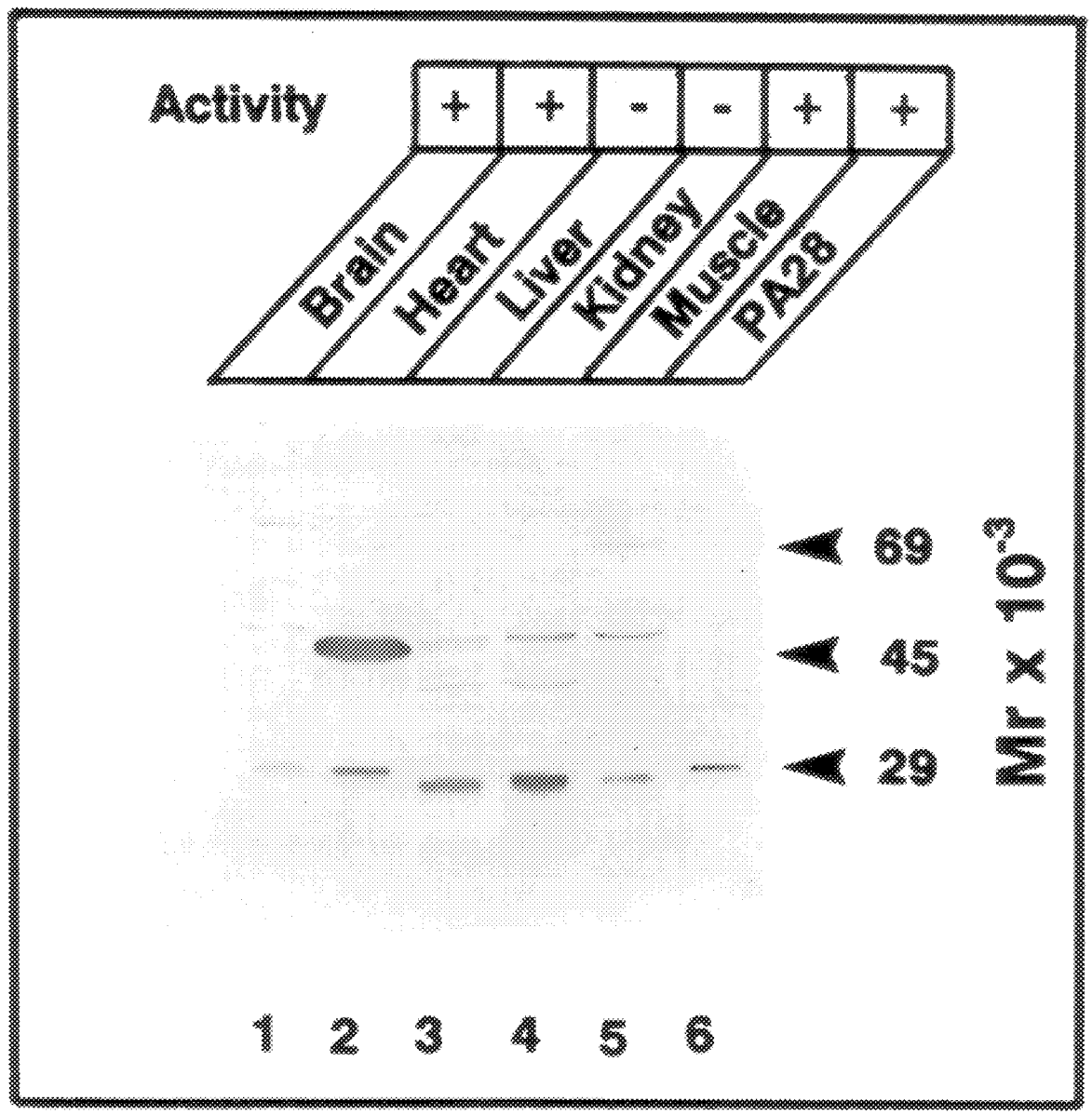
FIG. 10 shows the tissue distribution of PA28. The indicated tissues were removed from a 150 g rat immediately after sacrifice, cooled on ice and homogenized in a buffer consisting of 20 mM Tris-HCl, pH 7.6, 20 mM NaCl, 1 mM EDTA and 5 mM β mercaptoethanol (20% w/v) using a Polytron homogenizer. A supernatant fraction of the homogenate was prepared by centrifugation at 14,500×g for 30 min. Samples of each extract were treated with SDS-sample buffer and subjected to SDS-PAGE and immunoblotting as described under Example I. The box indicates the presence (+) of absence (−) of PA28 activity in these extracts. Similar immunoblot patterns and activity profiles were found in analogous studies using cow and rabbit tissues. Lane 1, Brain (100 μg protein); Lane 2, Skeletal muscle (80 μg protein); Lane 3, Kidney (40 μg protein); Lane 4, Liver (40 μg protein); Lane 5, Heart (40 μg protein); and Lane 6, Purified bovine red blood cell PA28 (0.1 μg).
Figure 11:
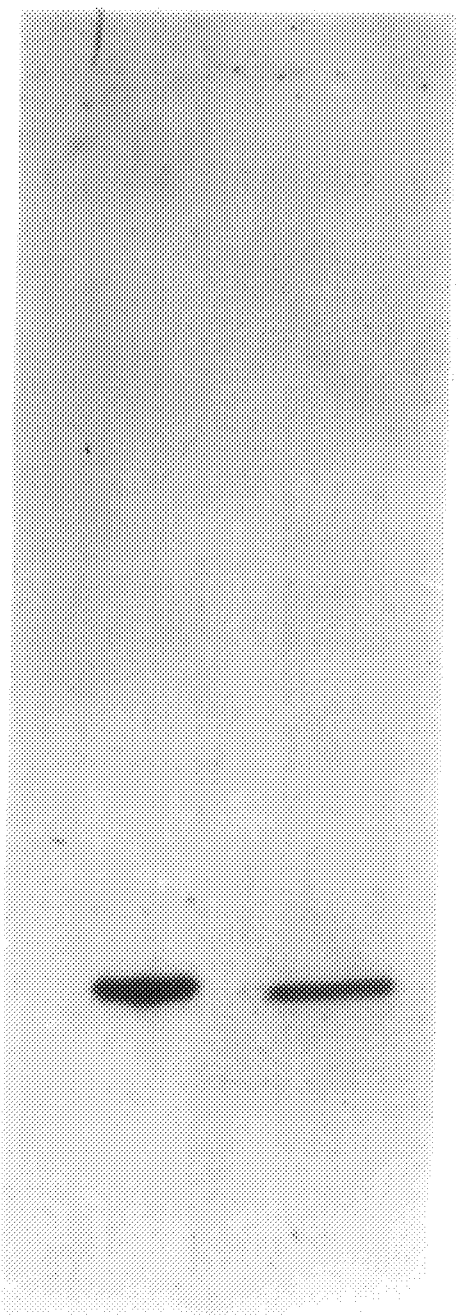
FIG. 11 shows the purification of an inactive form of PA28 from rat liver. PA28 was purified from rat liver using a procedure similar to that described for PA28 from bovine red blood cells. This included successive chromatography on DEAE-Sephacel, hydroxylapatite, phenyl-Sepharose, and Sephacryl S-300 columns, similar to the purification described in Example I; PA28 content was monitored by immunoblotting. The inactive PA28 migrated similarly to active PA28 on all of these columns. Samples of active PA28 from bovine red blood cells (0.1 μg, Lane 1), and inactive PA28 from rat liver (0.1 μg, Lane 2), were subjected to SDS-PAGE and immunoblotting as described in Example I.

Identification of inactive forms of PA28 in tissue extracts. In order to determine the tissue and species distribution of PA28, the content of this protein from different sources was examined by two methods. First, crude soluble extracts of various tissues from rat, cow, and rabbit were subjected to immunoblotting using an antibody prepared against purified bovine red blood cell PA28. Second, small-scale, partial purifications of PA28 from these same extracts were conducted and monitored by assay for PA28 activity. The immunoblotting data, shown in FIG. 10 for rat tissues, indicate that all tissues examined contained an immunoreactive protein at a molecular weight of approximately 28,000. Similar results were obtained for rabbit and bovine tissues. These results indicate that PA28, like the protein that it regulates, the proteasome, is widely distributed. In most of these samples, additional immunoreactive bands with apparent molecular weights of 45,000 and 55,000, were also observed. These bands were detected even after preabsorption of the antisera with the respective tissue extract, but they were not detected when equivalent blots were probed with non-immune or preimmune sera. Furthermore, antibodies that were affinity purified against PA28 also crossreacted with the same higher molecular weight bands. These higher molecular weight bands may represent modified forms of PA28 or proteins distinct from, but immunologically related to, PA28. In contrast to the identification of PA28 protein in all tested tissues, detection of PA28 activity among the same sources varied greatly. In fact, tissue extracts which showed the highest PA28 content by immunoblotting (e.g. kidney and liver) had no detectable PA28 activity. The lack of PA28 activity could be accounted for by an inactive form of the protein. Alternatively, some extracts might contain proteins that interfere with PA28 function in the assay. In order to distinguish between these possibilities, PA28 was purified from rat liver, a tissue in which no PA28 activity could be detected. The same purification scheme employed for active PA28 (see Example I) was used and was monitored by immunoblotting. Inactive PA28 behaved similarly to active PA28 on the various chromatographic columns used for purification. Although the purified liver PA28 had subunit and native molecular weights (28,000 and 180,000, respectively) indistinguishable from those of active PA28, it had no detectable PA28 activity (FIGS. 11, 12A, 12B, 12C and 12D). These results demonstrate that PA28 is present in some tissues extracts as an inactive protein.

Identification, purification and characterization of a protein that inactivates PA28. One explanation for these results is that some tissues contain a factor that inactivates PA28. In order to test for this factor, purified active PA28 was incubated with extracts from bovine liver, a tissue which contained PA28 protein, but had no demonstrable PA28 activity. PA28 activity was lost in a time-dependent fashion during the incubation (only in the presence of the liver extract), even though the amount and apparent molecular weight of PA28 protein, detected by immunoblotting, were not significantly altered. A preliminary characterization of the PA28-inactivating activity indicated that it had an acidic pH optimum, and was inhibited by the sulfhydryl alkylating agent, iodoacetate, and by the protease inhibitor, leupeptin. These results suggested that the inactivating factor might be a lysosomal peptidase. In fact, soluble extracts of a subcellular fraction enriched for lysosomes from bovine or rat liver were also highly enriched for PA28-inactivating activity. Inactivation of purified PA28 was used as an assay for the purification of the responsible protein from bovine liver lysosomes.

Table 3 is a summary of the purification of the PA28 inactivating protein from bovine lysosomes.

TABLE 3

PURIFICATION OF PA28-INACTIVATING PROTEIN FROM BOVINE LIVER LYSOSOMES[1]

| Stage | Volume (ml) | Protein (mg) | Total Activity (units × $10^{-5}$) | Specific Activity units/µg protein | Purification (fold) |
|---|---|---|---|---|---|
| Homogenate | 1,000 | 35,000 | — | — | — |
| Lysosomal Lysate | 100 | 200 | 25.7 | 13 | — |
| Hydroxyapatite | 70 | 32 | 15.6 | 49 | 3.8 |
| DEAE-Fractogel | 45 | 4.5 | 7.65 | 170 | 13.1 |
| Sephacryl S-100 | 3 | 0.09 | 1.53 | 1,700 | 131 |

[1]The PA28-inactivating factor was purified from a subcellular fraction of bovine liver enriched for lysosomes. One unit of activity is defined as the inhibition of one unit of PA28 activity/min.

Figure 14:
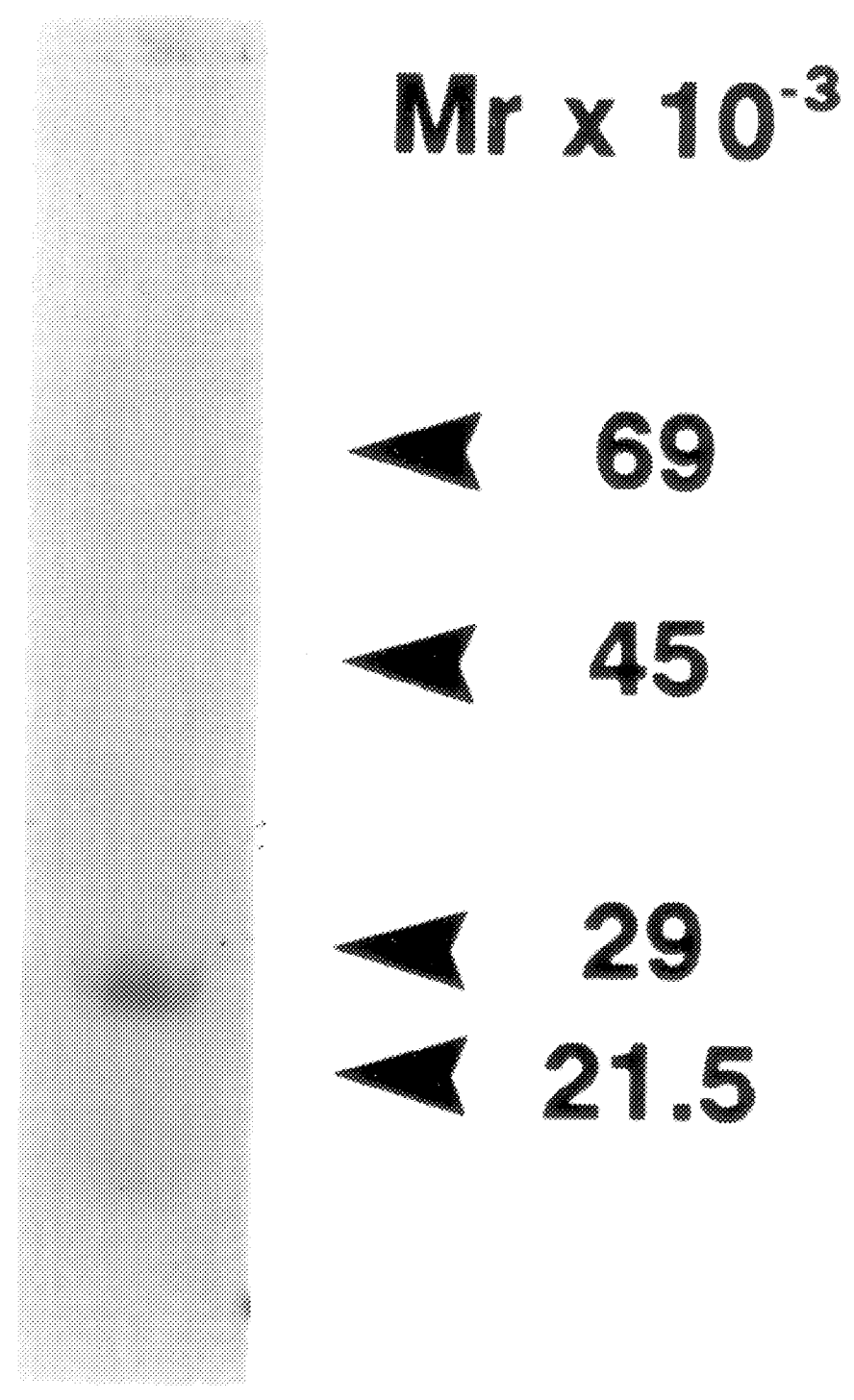

Characterization of the protein that inactivates PA28. The PA28 inactivating activity from the gel filtration column was subjected to SDS-PAGE on 12.5% polyacrylamide gels. The sample consisted of a single band with an apparent molecular weight of 27,000 (FIG. 14). Given the estimated native molecular weight of 50,000 (FIGS. 13A, 13B, and 13C) the protein seems to be composed of a homodimer.

Figure 15:
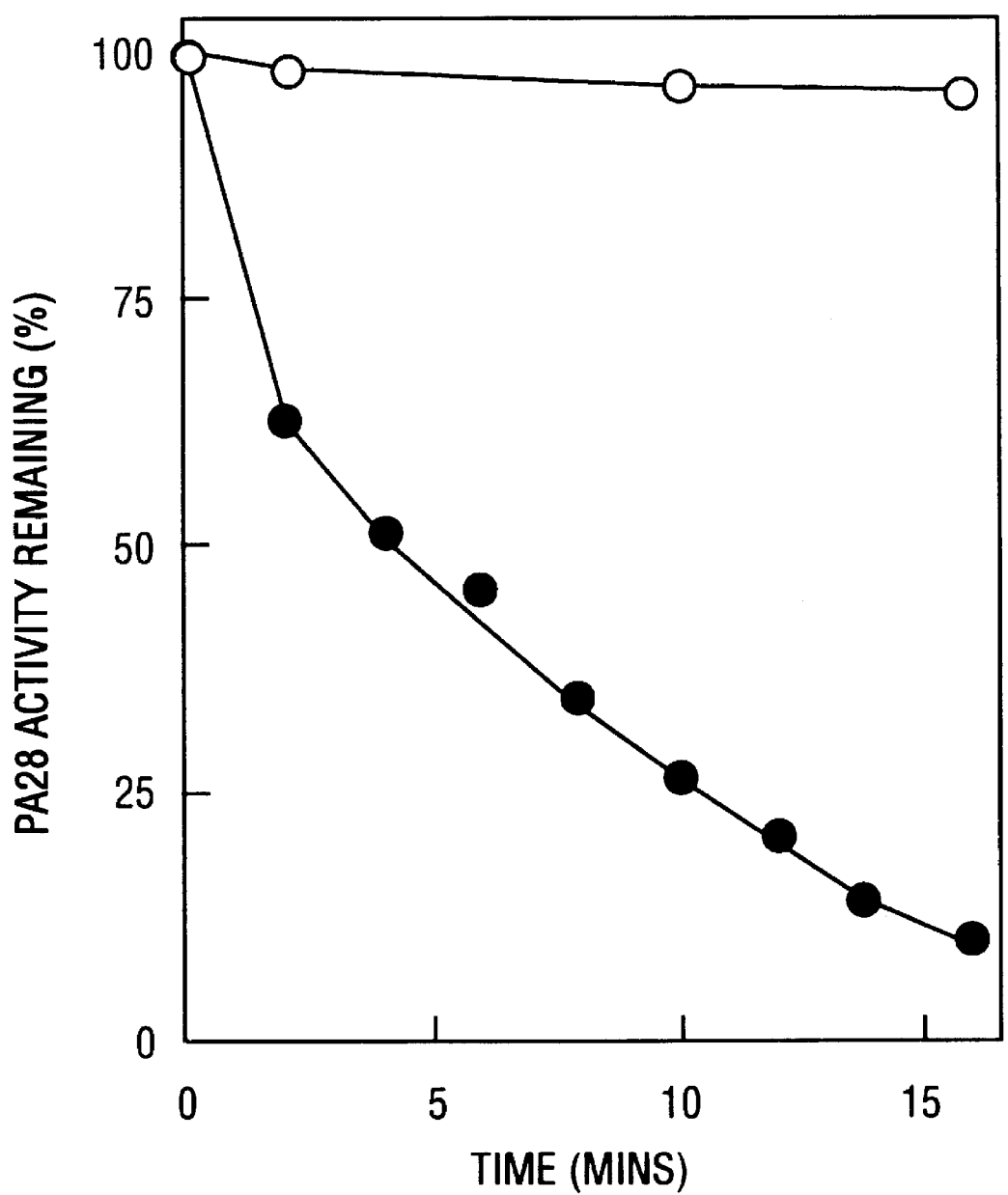
FIG. 15 shows the effects of purified PA28-inactivating protein on PA28. Purified PA28 was incubated in the presence (●) and absence (○) of purified PA28-inactivating protein (0.1 μg) at pH 5.2, 30° C. for the indicated times. Aliquots were assayed for PA28 activity remaining.

PA28 activity was lost in a time-dependent fashion in the presence of the inactivating protein. FIG. 15 shows these data for the Suc-Leu-Leu-Val-Tyr-AMC hydrolyzing activity. Similar rates of PA28 inactivation were observed using other peptidase activities of the proteasome, providing further evidence that PA28 modulates the multiple peptidase activities of the proteasome in a coordinated fashion. A similar experiment was performed to determine the pH optimum of the inactivating factor. The fastest rate of inactivation occurred at pH 5.5.

The co-purification of PA28-inactivating activity with Z-Leu-Arg-MNA hydrolyzing activity indicated that these activities were accounted for by the same enzyme and that PA28 inactivation resulted from proteolytic modification. In order to demonstrate further that the inactivating protein was a proteolytic enzyme, its ability to hydrolyze various synthetic peptide substrates and large protein substrates was assessed. The results, shown in Table 4, demonstrate that the PA28-inactivating protein hydrolyzed various amino-terminally blocked di- and tri-peptides. Of the substrates tested, those with arginine or lysine in the P1 position were cleaved most rapidly. Maximal rates of hydrolysis of all of these substrates required the presence of sulfhydryl reducing agents such as β-mercaptoethanol or DTT, suggesting that the enzyme was a sulfhydryl protease. Additional evidence for this conclusion is provided in Table 5. The pH optimum of peptide hydrolysis was 5.5, the same value as that for PA28 inactivation. No detectable hydrolysis of large protein substrates such as casein or lysozyme was observed under a variety of assay conditions, indicating that the protein had very poor endoprotease activity.

TABLE 4

HYDROLYSIS OF SYNTHETIC PEPTIDES BY PA28-INACTIVATING PROTEIN[1]

| SUBSTRATE | UNITS/μg |
| --- | --- |
| Z—Leu—Arg—MNA | 98 |
| Z—Val—Leu—Arg—MNA | 28 |
| Z—Leu—Leu—Lys—MNA | 19 |
| Z—Gly—Pro—Arg—MNA | 13 |
| Z—Ser—Tyr—MNA | 0 |
| Suc—Phe—Leu—Phe—MNA | 0 |
| Z—Arg—MNA | 0 |
| Z—Gly—Gly—Phe—βNA | 0 |
| Suc—Tyr—AMC | 0 |

[1]Purified PA28-inactivating protein (0.05 μg) was incubated in the presence 50 μM concentrations of the indicated substrates, 50 mM MES buffer, pH 5.2, 1 mM β-mercaptoethanol in a final volume of 1.0 ml. Reactions were carried out at 30° C. and the release of the reporter group was monitored directly by fluorescence. 1.0 unit of activity is defined as the increase in product concentration of 1.0 nM/min.

The effect of various protease inhibitors on the purified PA28-inactivating protein was determined. The results, shown in Table 5, indicate that a variety of protease inhibitors inhibited both PA28-inactivating activity and the hydrolysis of Z-Leu-Arg-MNA. The peptide aldehyde protease inhibitors, leupeptin, antipain, and chymostatin, each inhibited the PA28-inactivating protein at concentrations in the μM range. Several inhibitors of serine-type proteases (aminoethylbenzenesulfonylfluoride, and 3,4-dichloroisocoumarin), had no effect on either PA28-inactivating activity or Z-Leu-Arg-MNA hydrolysis. Sulf-hydryl alkylating agents, such as iodoacetate, inhibited each activity. These various results provide further evidence that the two activities are accounted for by the same enzyme. In total, the data indicate that the PA28-inactivating protein is a peptidase of the sulfhydryl class, in particular, a lysosomal peptidase.

TABLE 5

EFFECT OF PROTEASE INHIBITORS ON THE PA28-INACTIVATING PROTEIN[1]

| | | (% Inhibition) | |
| --- | --- | --- | --- |
| Inhibitor | Concentration | Peptidase Activity | PA28-Inactivating Activity |
| None | — | | |
| Leupeptin | 1 μM | 100 | 100 |
| Antipain | 2 μM | 88 | 90 |
| Chymostatin | 5 μM | 83 | ND |
| Iodoacetate | 100 μM | 83 | 93 |
| TLCK | 50 μM | 88 | ND |
| Z—Phe—Ala—CHN$_2$ | 15 μM | 85 | ND |
| Bestatin | 2 μM | 19 | ND |
| TPCK | 50 μM | 0 | 0 |
| Aminoethylbenzene-sulfonylfluoride | 1 mM | 0 | 0 |
| 3,4-Dichloroisocoumarin | 1 mM | 0 | 0 |

[1]Purified PA28-inactivating protein was preincubated with the indicated compound for 10 min at 30° C. and then assayed for either PA28-inactivating activity or for hydrolysis of Z—Leu—Arg—MNA. The data are presented as a percent inhibition compared to untreated protein. ND, not determined.

A review of the literature indicated that the purified PA28inactivating protein had physical and catalytic properties that closely resemble those of lysosomal carboxypeptidase B (13–19). Several lines of evidence strongly indicate that it inactivated PA28 by catalyzing limited proteolysis of the carboxyl terminus of PA28. First, the protein inactivated PA28 in a time- and concentration-dependent fashion without detectably altering its native or subunit molecular weight (FIGS. 11, 12A, 12B, 12C, 12D and 15). Continued incubation of PA28 with the purified inactivating protein for up to 12 hrs produced no detectable change in PA28's size on SDS-PAGE. These data indicate that the inactivating protein acted as an exopeptidase rather than as an endopeptidase. Second, the inactivating protein seemed to act at the carboxyl terminus of PA28 because both the active and inactivated forms of PA28 were blocked to Edman degradation. Third, two purified carboxypeptidases, bovine pancreatic carboxypeptidase B and yeast carboxypeptidase Y, each inactivated PA28 without detectably altering its molecular weight on SDS-PAGE (Table 6).

TABLE 6

EFFECT OF PEPTIDASES ON PA28 INACTIVATION[1]

| PEPTIDASE | PA28 ACTIVITY (% CONTROL) |
| --- | --- |
| PA28-Inactivating Protein | 5 |
| Carboxypeptidase B | 10 |

TABLE 6-continued

EFFECT OF PEPTIDASES ON PA28 INACTIVATION[1]

| PEPTIDASE | PA28 ACTIVITY (% CONTROL) |
|---|---|
| Carboxypeptidase Y | 6 |
| Aminopeptidase M | 93 |

[1]Inactivation of PA28 by the indicated peptidases was tested and compared to inactivation of PA28 by the purified inactivating protein. The inactivation assay was similar to that described under "Materials and Methods" but was altered for pH optimization of individual peptidases as follows: Purified PA28-inactivating protein from bovine liver, 0.1 μg, pH 5.2; Carboxypeptidase B from bovine pancreas (Sigma C-7261), 0.1 μg, pH 7.5; Carboxypeptidase Y from yeast, (Boehringer, 1111914) 0.1 μg, pH 7.0; and Aminopeptidase M from hog kidney (Boehringer, 102768) 0.5 μg, pH 7.5. For each experiment, PA28 was also preincubated under identical conditions without the respective peptidase. The data are compared to that of the corresponding control. PA28 activity was stable under all of the control conditions.

Aminopeptidase P, on the other hand, had no effect on PA28 activity. The endoprotease, trypsin, rapidly inactivated PA28, but resulted in the extensive degradation of the protein to small peptide fragments. This latter result further demonstrates the limited nature of the action of the carboxypeptidases on PA28. Taken together with the catalytic features of the PA28-inactivating protein, these results strongly indicate that PA28 was inactivated by limited proteolysis at its carboxyl terminus.

Figure 12:
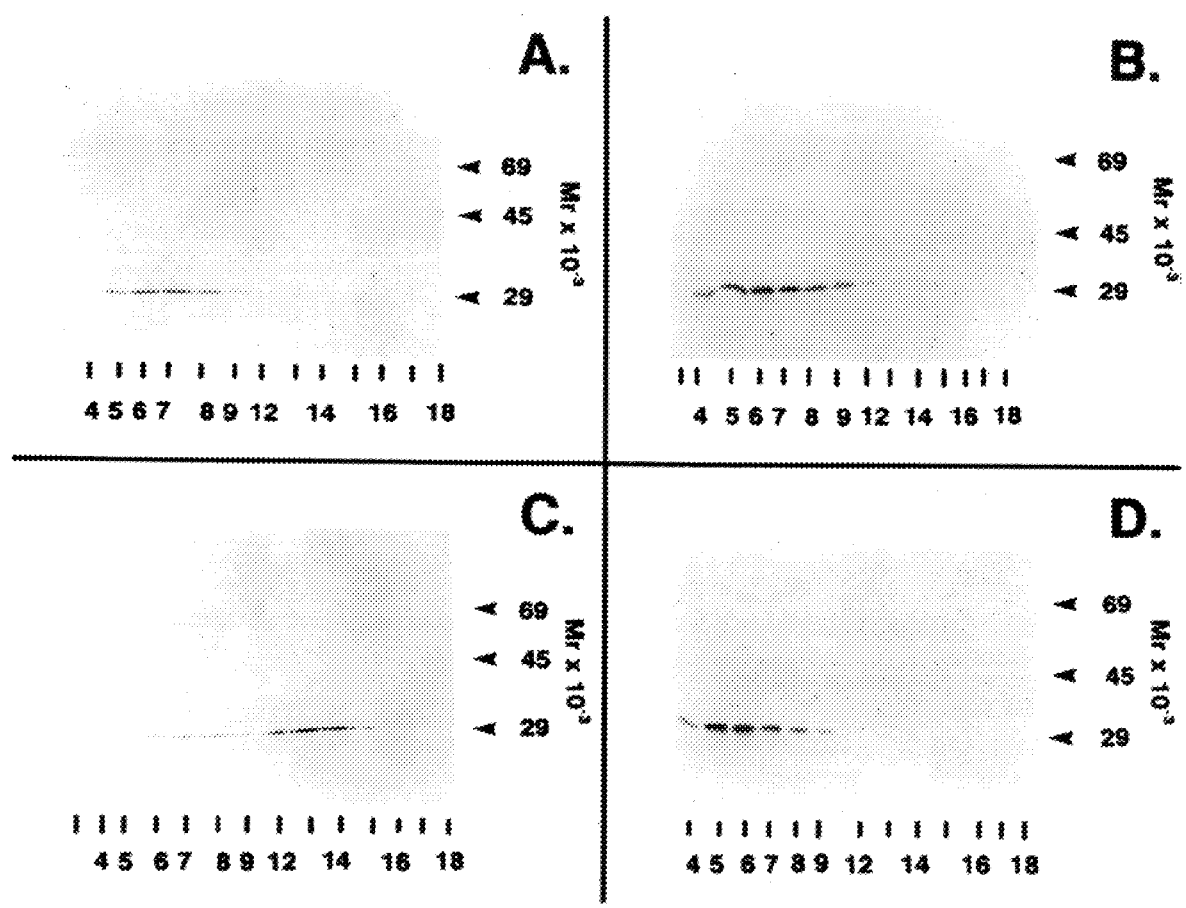
FIG. 12A, FIG. 12B, FIG. 12C and FIG. 12D show that the carboxypeptidase B-treated PA28 fails to bind to the proteasome. Purified PA28 (4 μg) was incubated for 20 min. at 30° C. in 50 mM MES, pH 5.2, 2 mM DDT, in the presence or absence of purified lysosomal carboxypeptidase B (0.1 μg) in a final reaction volume of 120 μl. After the incubation, the treated PA28 had no detectable proteasome stimulatory activity; the untreated control retained greater than 90% of its activity. At the end of the incubation, 1M Tris-HCl, pH 8.0 was added to return the pH to 7.5. The two samples were each divided into equal portions. One portion was mixed with 25 μl of 20 mM Tris-HCl, pH 7.6, 20 mM NaCl buffer, while the other was mixed with approximately 25 μg of purified proteasome in 25 μl of the same buffer. Each portion was incubated at 25° C. for 15 min. and then subjected to velocity sedimentation centrifugation using 10–40% glycerol density gradients. Samples of the fractions were subjected to SDS-PAGE followed by immunoblotting using an anti-PA28 antibody. The normal sedimentation position for purified proteasome is fraction 13. Sedimentation positions of purified protein standards thyroglobulin ($M_r$=660,000), and aldolase ($M_r$=158,000), were determined in parallel tubes and are indicated. Molecular weight standards for SDS-PAGE include: bovine serum albumin ($M_r$=69,000), ovalbumin ($M_r$=45,000), and carbonic anhydrase ($M_r$=29,000).

Inactive PA28 fails to bind to the proteasome. The results presented above indicate that the carboxyterminal region of PA28 is necessary for PA28 activation of the proteasome. To define its role in this function, active and carboxypeptidase-inactivated forms of PA28 were incubated with the proteasome and then subjected to velocity sedimentation centrifugation through glycerol density gradients, a method that was previously shown effective for isolating the proteasome/PA28 complex (see Example I). The gradients were then analyzed for PA28 content using an anti-PA28 antibody. The results of the experiment are shown in FIGS. 12A, 12B, 12C and 12D). In the absence of the proteasome, both active and carboxypeptidase-inactivated PA28s sedimented at similar positions corresponding to their expected native size (FIGS. 12A and 12B). Active PA28 bound to the proteasome and cosedimented with it (FIG. 12C). However, carboxypeptidase-inactivated PA28 did not cosediment with the proteasome, indicating that it could not bind to it. These results indicate that a small region of the carboxyl terminus of PA28 is required for binding to the proteasome.

The purified PA28-inactivating protein had biochemical and catalytic properties very similar to those of lysosomal carboxypeptidase B (49–55). These properties included: 1) a lysosomal localization, 2) an acidic pH optimum, 3) classification in the sulfhydryl protease family, 4) inhibition by peptidase inhibitors such as leupeptin, 5) hydrolysis of synthetic peptides previously shown to be cleaved by lysosomal carboxypeptidase B (54,55), 6) undetectable endopeptidase activity against PA28 and other large proteins, and 7) a native molecular weight of 50,000, with a homodimeric subunit structure (49, 55).

Regardless of the exact identification of the purified inactivating protein with respect to previously described enzymes, the evidence that it acts by proteolytically modifying the carboxyterminus of PA28 is strong. Furthermore, other carboxypeptidases, including pancreatic carboxypeptidase B and carboxypeptidase Y from yeast, also inactivated PA28 by limited proteolysis.

The exposure of PA28 to lysosomal carboxypeptidase B, or related peptidases, likely resulted from the disruption of lysosomes during tissue homogenization. In fact, tissues with high lysosome content such as liver and kidney, had no detectable PA28 despite their high level of PA28 protein. When tissue extracts were prepared by homogenization in buffers that minimized the disruption of lysosomes (for example, by gentle homogenization of 0.25M sucrose), active PA28 could be observed in tissues such as liver. Therefore, the physiological significance of PA28 inactivation by lysosomal carboxypeptidase B is unclear. Nevertheless, peptidases with related specificities may function to inactivate this protein in intact cells.

Regardless of the physiological significance of PA28 inactivation by proteolytic processing, this modification has identified a critical structural requirement of PA28 for its regulation of the proteasome. Specifically, inactivated PA28 failed to bind to the proteasome. This result suggests that the carboxyl terminus of PA28 is necessary for PA28 interaction with the proteasome and that this interaction is required for proteasome activation.

EXAMPLE III

The Cloning, Nucleotide Sequence and Amino Acid Sequence of PA28

Antibodies against PA28 obtained as described in Example II were used to screen a bovine brain expression library. Positive clones were identified and the clone containing the largest cDNA insert was isolated and sequenced. It contains an open reading frame encoding for a protein with a molecular weight of 21,893. The deduced amino acid sequence contains the sequences of a number of tryptic peptides of PA28, sequenced by automated Edman degradation (FIG. 16A and FIG. 16B). Thus, this clone represents about 75% of the expected PA28 sequence. This protein is not homologous to any known protein listed in current data banks including any proteasome subunit. The present inventors have used these cDNA data to construct oligonucleotide probes representing the 5' end of the current sequence to screen additional libraries for the full-length clone. A clone with a larger cDNA insert (1.3 kb) has very recently been identified and is being sequenced.

EXAMPLE IV

PA700, A High Molecular Weight, ATP-Dependent Activator of the Proteasome

Materials and Methods

Cells and preparation of lysates. Bovine blood was collected in the presence of heparin from a meat processing plant. The red cells were collected by centrifugation at 2000×g for 1 hr. The supernatant and the buffy coat were removed by aspiration. The remaining cell pellet was resuspended in phosphate-buffered saline and recentrifuged. The washing procedure was repeated four times.

Cells were lysed by adding three volumes of extract buffer to one volume of the packed cells and stirring the mixture for 10 minutes. The buffer consisted of 20 mM Tris-HCl, pH7.6, 20 mM NaCl, 1 mM EDTA, 1 mM β-mercaptoethanol.

Assay for proteasome. The proteasome assay is described in Example I.

Assay for PA700 activity. PA700 activity was assayed by measuring the increase in proteasome hydrolysis of the synthetic peptide Suc-Leu-Leu-Val-Tyr-AMC after preincubation of the two components in the presence of ATP. The standard preincubation solution consisted of 45 mM Tris-HCl, pH 7.5, 5 mM DTT, 60 μM ATP, 500 μM $MgCl_2$, 0.3 μg purified proteasome, PA700 as indicated in specific experiments, and any other component as specified, in a final volume of 50 μl. This solution was preincubated at 37° C. for 45 min. The preincubation was ended by the addition of 1.0 ml of a solution containing 50 mM Tris-HCl, pH 8.0, 1 mM DTT, and 50 μM Suc-Leu-Leu-Val-Tyr-AMC. The rate of hydrolysis of the substrate was determined directly by fluorescence as described previously. Routine control assays were conducted in parallel and consisted of the complete procedure but without PA700. Additional control assays were performed as described in the text. PA700 activity is defined as the increase in proteasome activity between the two conditions.

Results

Figure 17:
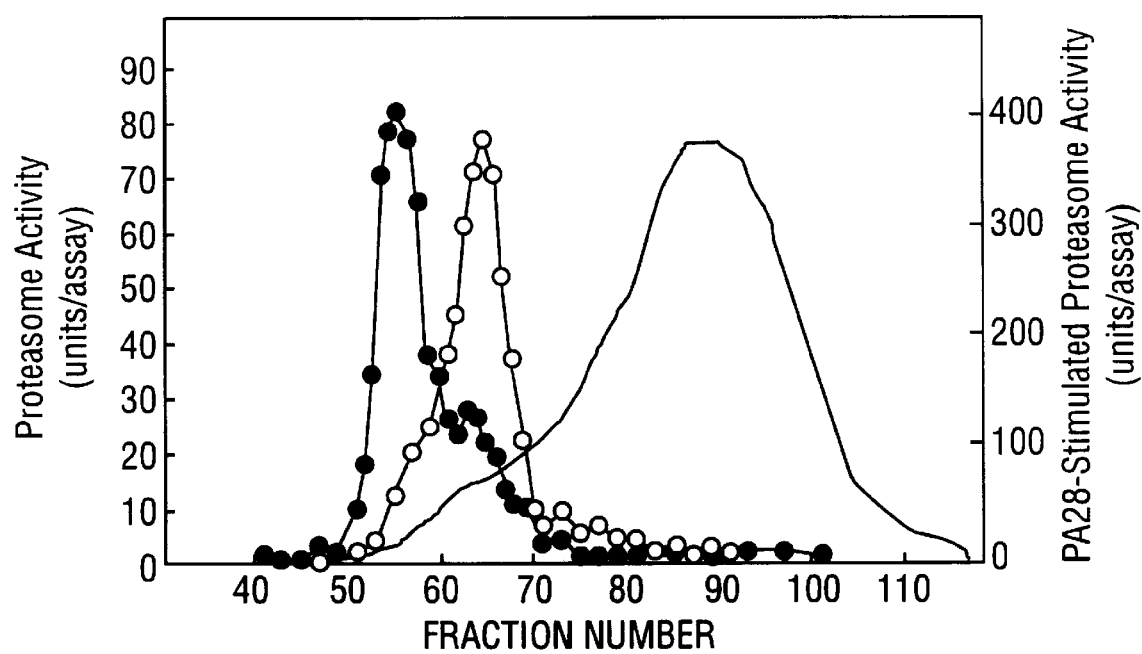
FIG. 17 shows the identification of proteasome/regulator protein complexes in soluble lysates of bovine red blood cells after gel filtration chromatography on Sephacryl S-400. Soluble lysates of bovine red blood cells were prepared as described in Example 4. Four mls of the extract was chromatographed on a column of Sephacryl S-400 (100×2.5 cm) equilibrated and eluted with a buffer containing 50 mM Tris-HCl, pH 7.6, 1 mM β-mercaptoethanol, and 20% glycerol. Total protein (−). The column was calibrated with compounds of known molecular weight: blue dextran ($M_r$=2,000,000); thyroglobulin ($M_r$=669,000); apoferritin ($M_r$=440,000); catalase (240,000); alcohol dehydrogenase ($M_r$=150,000). Proteasome activity: samples of the 4.5 ml fractions were assayed for proteasome activity in the absence (●) and presence (○) of purified PA28 protein (0.6 μg/assay), using Suc-Leu-Leu-Val-Tyr-AMC substrate as described under "Materials and Methods".
Figure 18:
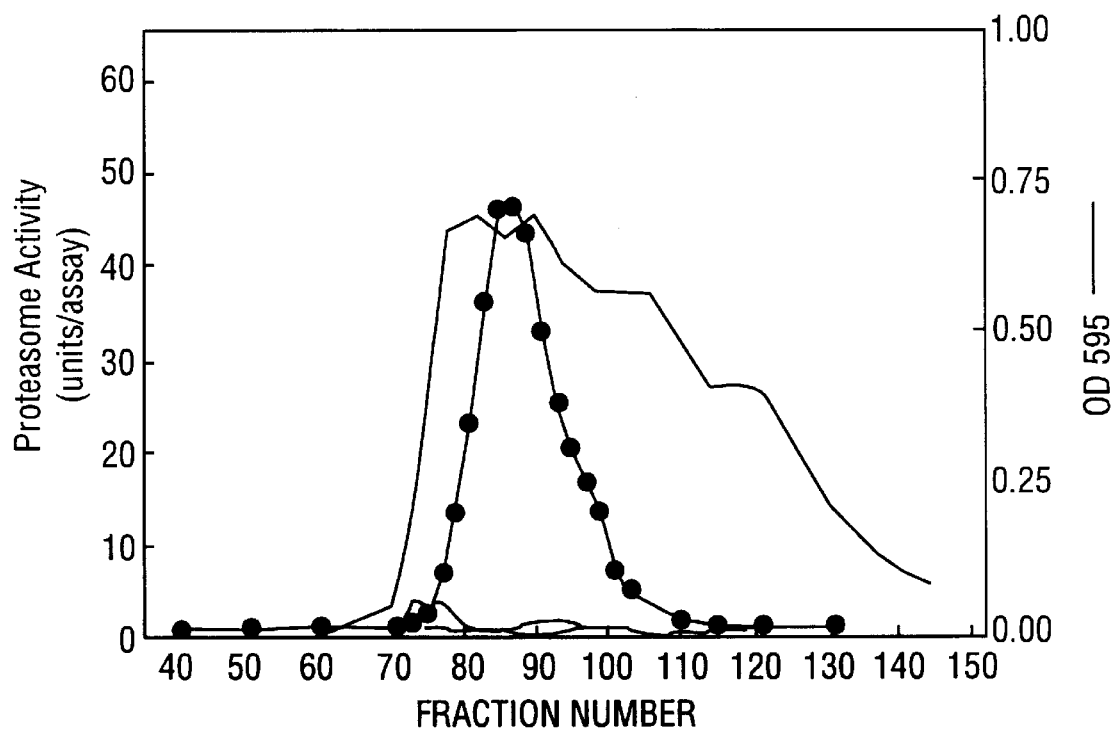
FIG. 18. Identification of a proteasome activator after Sepahacryl S-300 gel filtration chromatography. Fraction II proteins of a red blood cell lysate precipitating between 0–38% saturated ammonium sulfate were chromatographed on Sepahacryl S-300. Five μl of the column fractions were assayed for PA700 activity as described in Example 4. The column was calibrated with the same molecular weight markers as described in the legend to FIG. 17.
Figure 19:
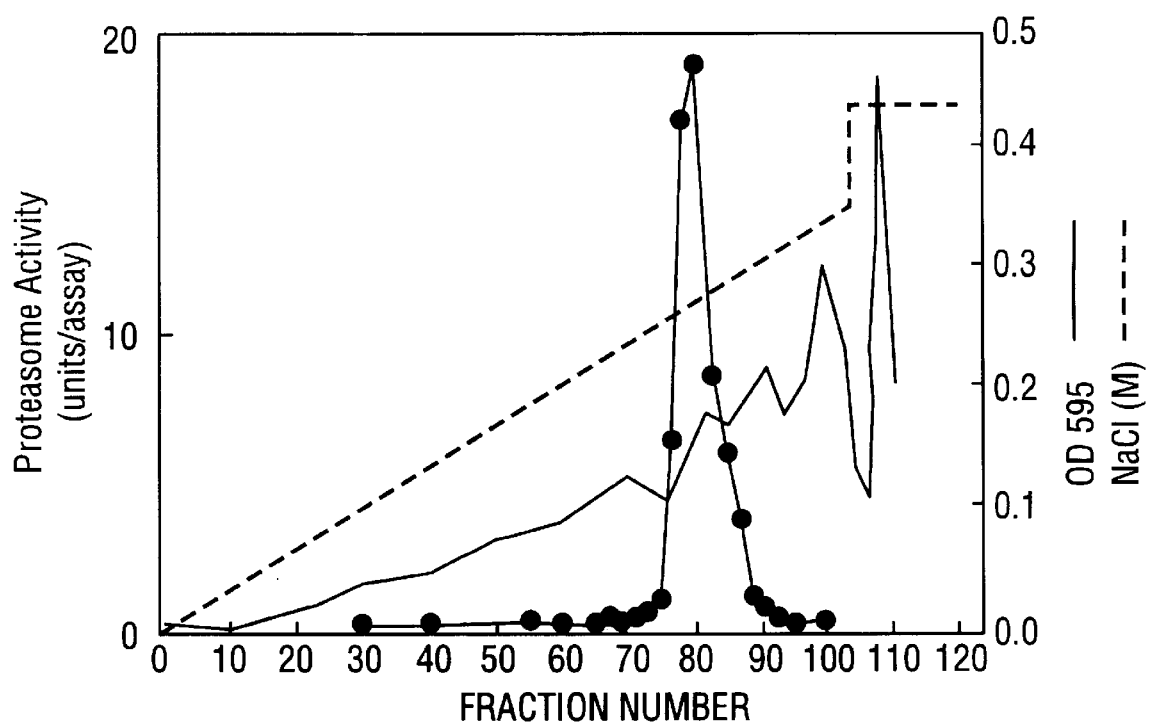
FIG. 19. DEAE-Fractogel ion-exchange chromatography of the proteasome activator. Fractions from the Sephacryl S-300 chromatography (FIG. 18) containing proteasome activating activity (fraction numbers 80–95) were pooled and applied to a column of DEAE-Fractogel (9×2.5 cm) equilibrated in 50 mM Tris-HCl, pH 7.6, 100 mM NaCl, and 1 mM β-mercaptoethanol. The bound proteins were eluted with a linear gradient of NaCl (0.1–0.35M) in the same buffer. Five μl of the 11 ml column fractions were assayed for proteasome activation as described in Example 4. In the absence of column fractions, the proteasome activity was 0.50 units/assay.
Figure 20:
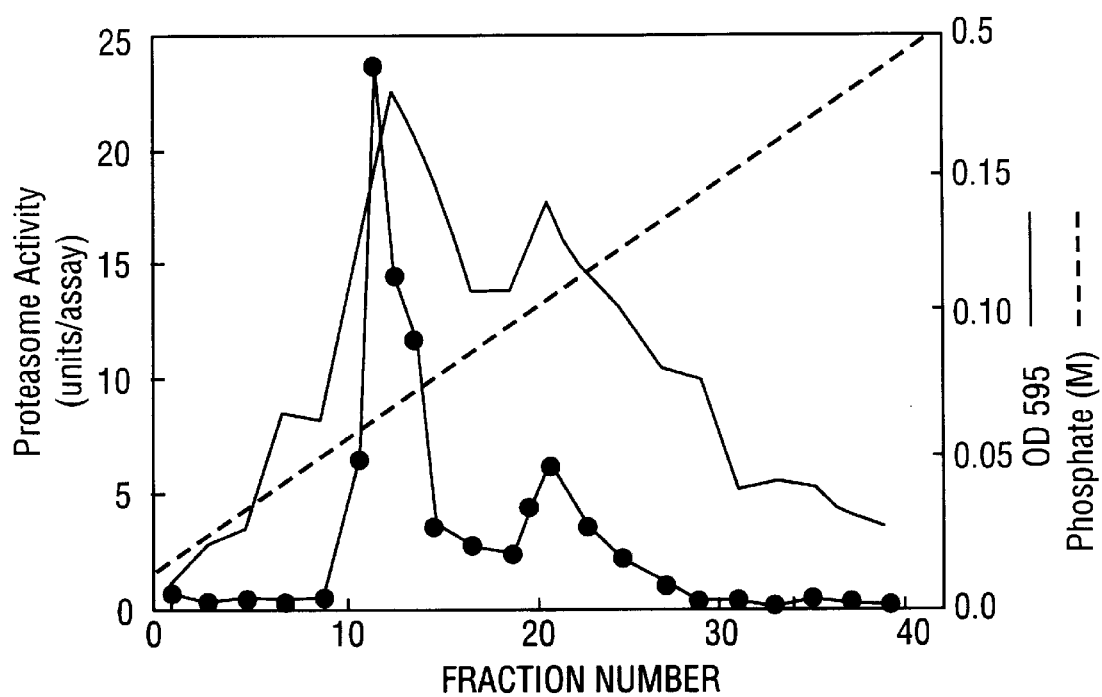
FIG. 20. Hydroxylapatite chromatography of the proteasome activator. Fractions from the DEAE-Fractogel column (FIG. 19) containing proteasome activating activity were pooled, dialyzed against a buffer consisting of 20 mM potassium phosphate, pH 7.6, 1 mM β-mercaptoethanol, 20% glycerol, and applied to a column of hydroxylapatite (10×2.5 cm) equilibrated in the same buffer. The bound proteins were eluted with a linear gradient of increasing phosphate concentration in the same buffer (20–200 mM). Five μl samples of the 9.0 ml fractions were assayed for proteasome activating activity as described in Example 4. In the absence of column fractions, proteasome activity was 0.53 units/assay.
Figure 21:
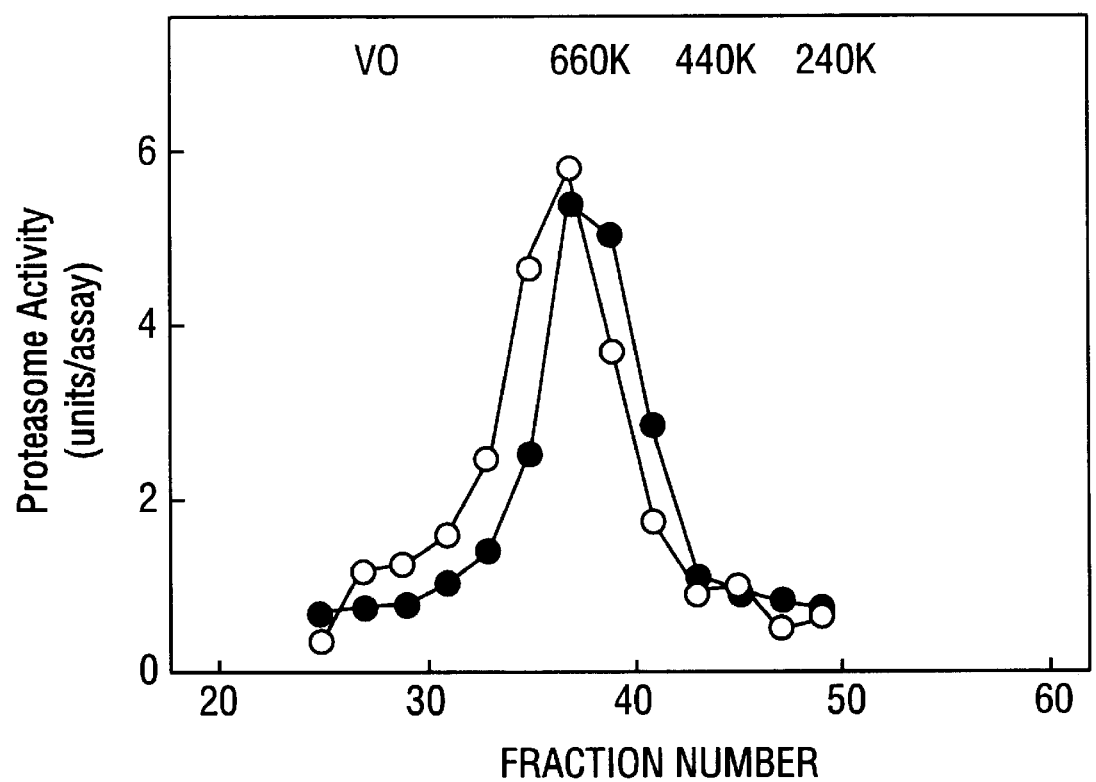
FIG. 21. Sephacryl S-400 gel filtration chromatography of Peak I and Peak II proteasome activators. The two proteasome activators, Peak I and Peak II from the hydroxylapatite chromatography were subjected to gel filtration column chromatography on Sephacryl S-400 (70×2.5 cm).
Figure 22:
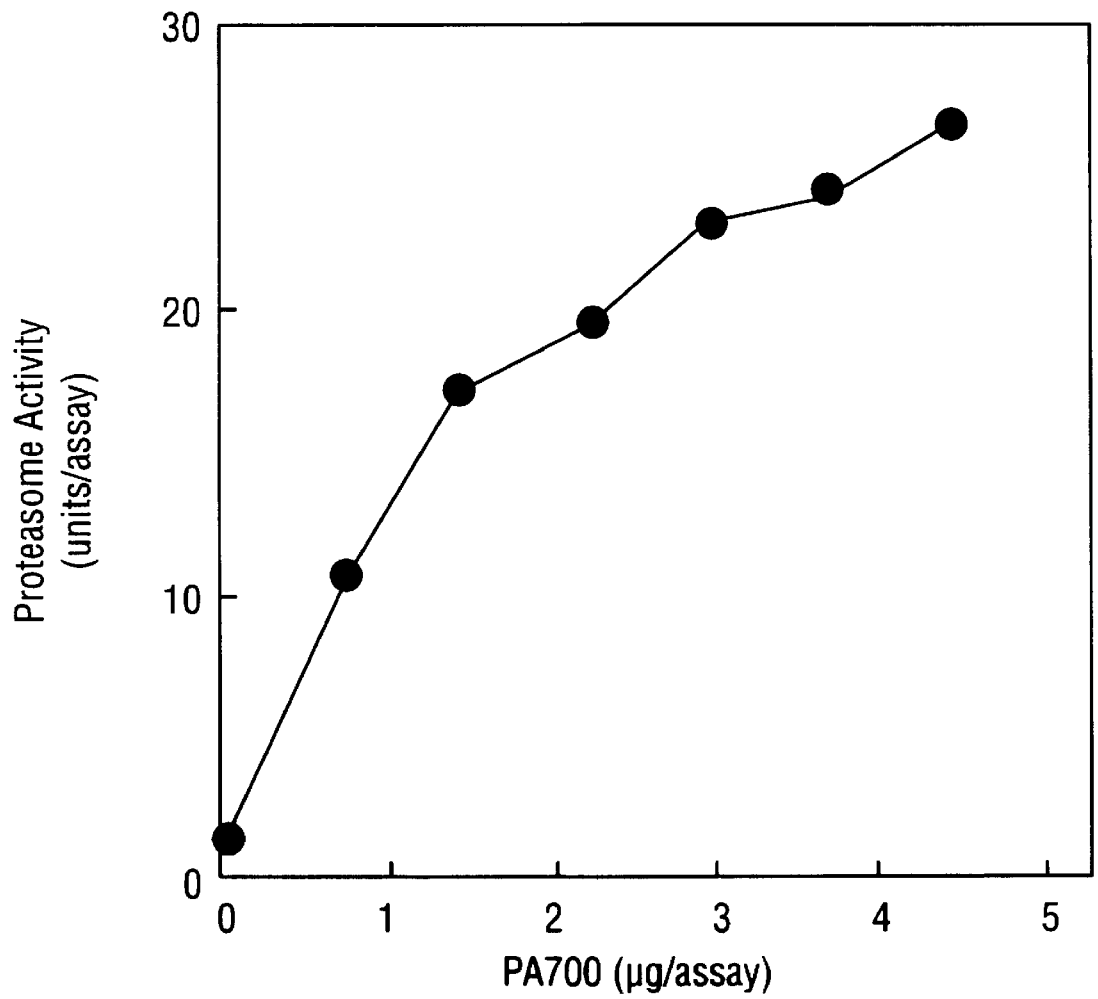
FIG. 22 demonstrates proteasome activity versus increasing concentrations of PA700.
Figure 23:
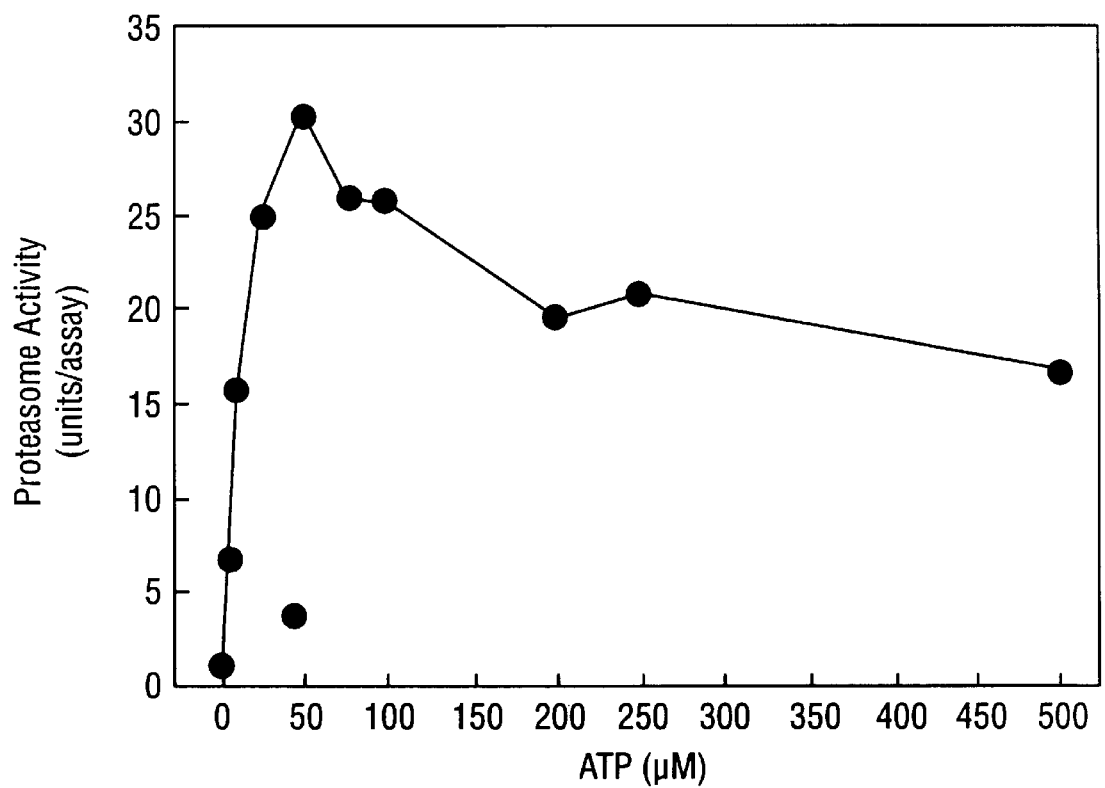
FIG. 23 demonstrates PA700-activated proteasome activity versus increasing concentrations of ATP.
Figure 24:
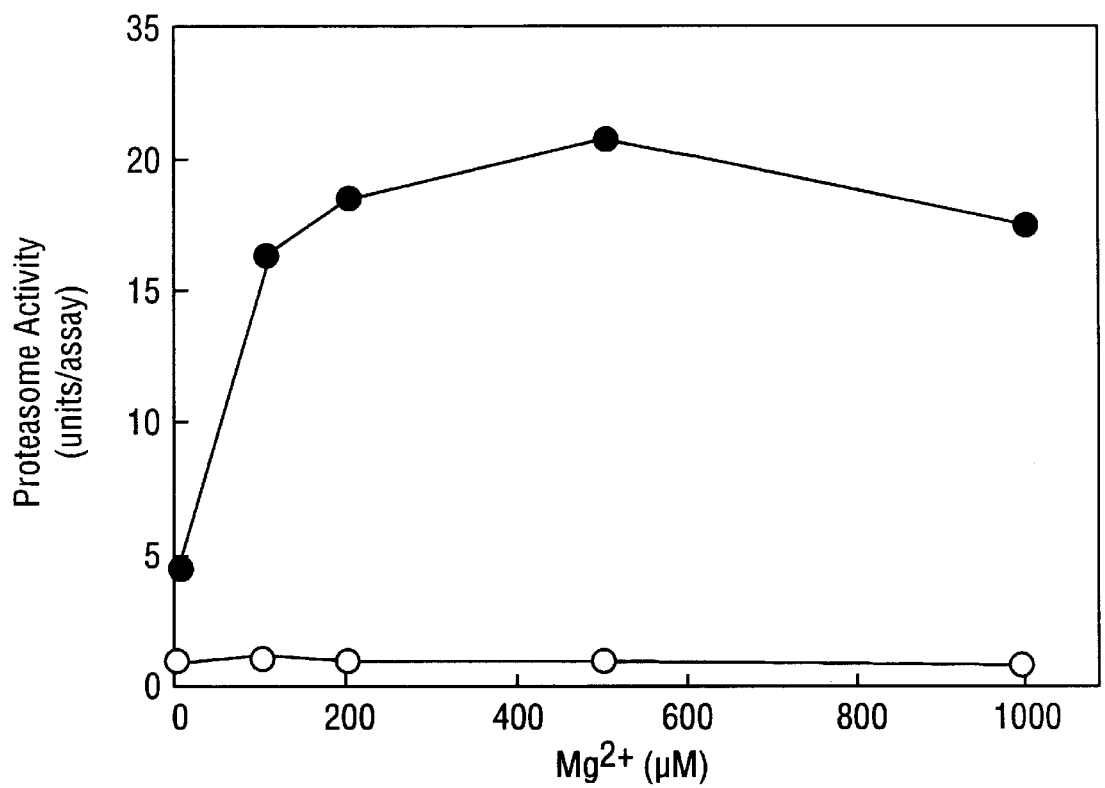
FIG. 24 shows PA700-activated proteasome activity versus increasing concentrations of Mg++. ● with exogenous proteasome, ○ control without exogenous proteasome.
Figure 25:
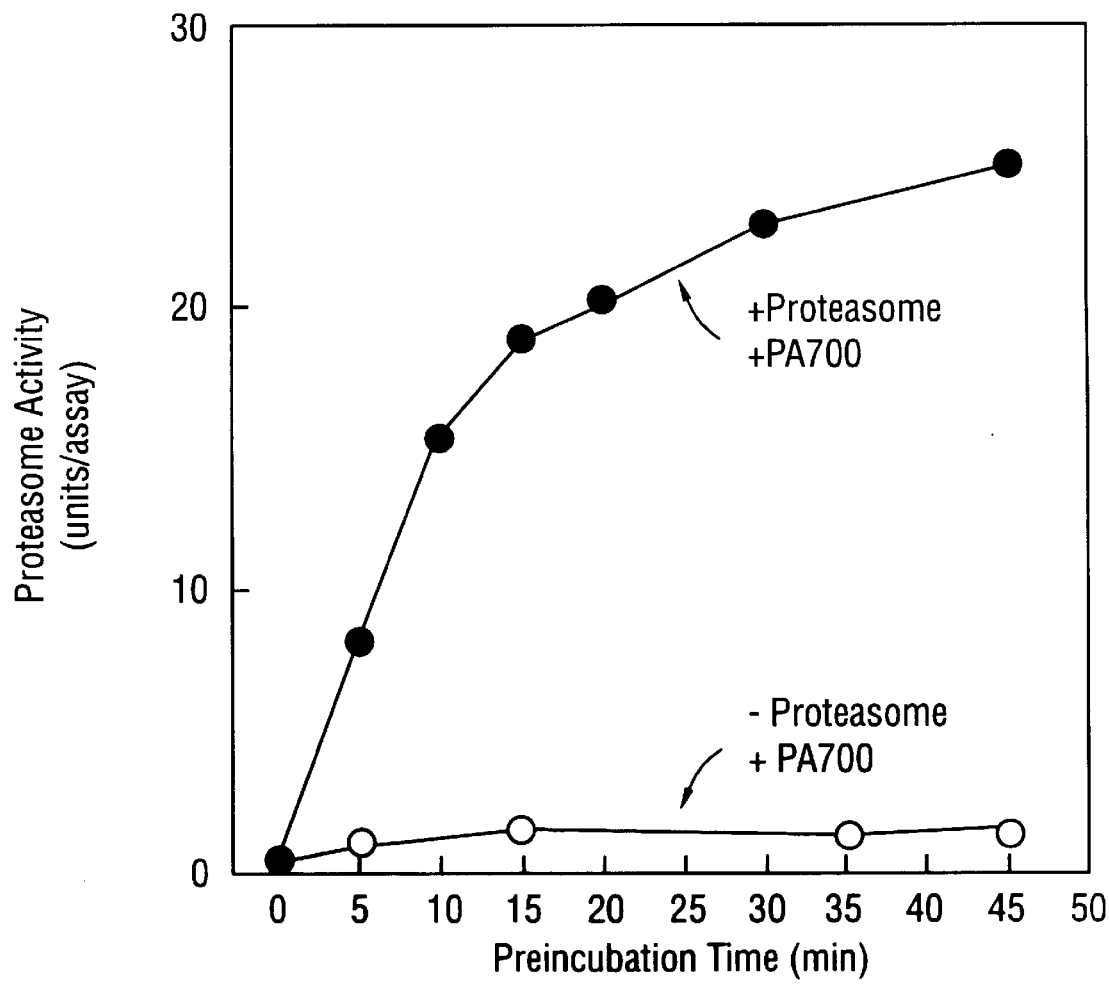
FIG. 25 shows PA700-activated proteasome activity versus preincubation time for (●) proteasome and PA700 and for (○) PA700 alone.

Identification of proteasome complexes in cell extracts. In order to identify protein complexes comprised of the 20S proteasome and specific modulatory proteins, red blood cell lysates which had not been treated with ammonium sulfate or exposed to buffers containing high concentrations of other salts were fractionated by gel filtration chromatography or by velocity sedimentation centrifugation. The proteasome content of the fractionated lysates was assessed by a functional assay with a peptide substrate, Suc-Leu-Leu-Val-Tyr-AMC, specific for the protease, and by an immunoassay with an antibody that recognizes several proteasome subunits. Each fractionation method identified two peaks of proteasome activity (FIG. 17). One peak contained most of the proteasome activity and had a molecular weight much greater than that expected for the purified proteasome. On the gel filtration column this molecular weight was estimated at approximately 1,7500,000, and most likely represents the so-called "26S protease" previously identified in many laboratories. The second peak contained much less activity and a molecular weight similar to that of the purified 20S proteasome, i.e., approximately 700,000. Immunoblotting of column fractions demonstrated that proteasome subunits also had a biomodal distribution. The first peak of proteasome protein was coincident with the higher molecular weight proteasome activity. The second peak of proteasome protein had a similar, but not identical distribution to that of the lower molecular weight proteasome activity. In repeated experiments with numerous independent preparations, the proteasome activity of the second peak always had a slightly greater apparent molecular weight than the corresponding proteasome protein. Most strikingly, the relative levels of proteasome protein in the two peaks were not quantitatively proportional to the corresponding proteasome activities. Thus, even though the 1,750,000-dalton proteasome had 3–4 times more activity than the 7000,000-dalton proteasome, it contained only about 20% as much proteasome protein. One possible explanation for these observations is that one of the proteins comprising the 1,750,000-dalton proteasome complex functions as an activator. In order to test this possibility, the distribution of a specific protein activator of the proteasome, PA28, was assessed by immunoblotting. The results demonstrate that PA28 protein displayed a trimodal distribution. Some of the PA28 was coincident with both the 1,750,000-dalton proteasome activity and the corresponding proteasome protein. Most of the PA 28 protein, however, had a distribution similar to that of the lower molecular weight proteasome activity. Nevertheless, like that activity, the distribution of PA28 protein had an apparent molecular weight that was slightly greater than the proteasome protein. The remainder of PA28 was identified at a position corresponding to an apparent molecular weight of about 200,000, i.e., the value characteristic of the purified PA28 protein. The column fractions were reassayed for proteasome activity after supplementation of the assays with purified Pa28. Exogenous PA28 had little effect on the activity of the 1,750,000-dalton proteasome but greatly stimulated the activity of the smaller proteasome peak. The distribution of proteasome activity that was stimulated by exogenous PA28 had an apparent molecular weight that was slightly but consistently lower than that of the endogenous activity, and its distribution was coincident with that of the proteasome protein in this region of the column. Although these various results have numerous possible interpretations, one that is consistent with the observations, and is supported by experiments described below, involves the differential association of PA28 and other regulatory proteins with the proteasome, and is as follows. The fractionated extract appears to contain at least three forms of the proteasome. The first corresponds to the 20S proteasome unassociated with other proteins. This enzyme has negligible activity, but is greatly stimulated by exogenous PA28. The second form of proteasome is associated with endogenous PA28. This complex has a higher molecular weight than that of the "free" 20S proteasome and accounts for the endogenous proteasome activity in the column fractions of corresponding to an approximate molecular weight of 700,000–800,000. Because this proteasome is already associated with PA28, its activity is not further stimulated by exogenous PA28. Thus, the difference is apparent molecular weight of the endogenous proteasome activity and the activity stimulated by exogenous PA28 represents the difference between bound and unbound PA28. The third form of proteasome is represented by the 1,750,000-dalton activity and likely represents a complex containing the proteasome, PA28, and other regulatory proteins. This analysis does not resolve the apparent discrepancy between the relative activity of the two proteasome peaks with the corresponding concentrations of proteasome and PA28 protein; i.e., the activity of the 1,750,000-dalton proteasome was much greater than expected for the relative concentrations of proteasome and PA28. One possible explanation for these results is that PA28 is not the only activator in the 1,750,000-dalton proteasome complex.

Identification of an ATP-dependent activation of proteasome activity. Based on the results described above, the present inventors initiated a screen for a proteasome activator(s) distinct from PA28. Soluble lysates of bovine red blood cells were fractionated and assayed for the ability to activate purified 20S proteasome. In order to simplify the analysis of such experiments, extracts were prepared that were relatively free of both the proteasome and PA28. Previous work demonstrated that treatment of "Fraction II" (see Materials and Methods) with ammonium sulfate to 38% saturation, precipitated proteins which did not contain significant levels of proteasome or PA28. This faction, however, does contain an inhibitor of the 20S proteasome. In fact, complete inhibition of proteasome activity was observed when samples of the extract were added to assays of the purified 20S proteasome. Therefore the assay conditions were varied in order to identify one that would differentially affect the interaction of proteasome with the inhibitor and hypothetical activators. One specific condition resulted in a large increase in proteasome activity. It involved preincubation of the fraction with purified proteasome in the presence of ATP and $Mg^{2+}$. Preliminary characterization of the activation indicated that it was time-dependent and required the presence of both the proteasome and the crude fraction (Table 7, see complete characterization below).

TABLE 7

EFFECT OF PA700 ON THE ACTIVATION OF PROTEASOME HYDROLYTIC ACTIVITIES[1]

| SUBSTRATE | PA700 − UNITS/ASSAY + | |
| --- | --- | --- |
| Suc—Leu—Leu—Val—Tyr—AMC | 0.51 | 16.60 |
| Z—Leu—Leu—Glu—βNA | 0.02 | 0.20 |
| Z—Val—Leu—Arg—MNA | 0.48 | 1.12 |
| Z—Gly—Gly—Leu—AMC | 2.5 | 6.0 |

[1]All assays have 50 μM substrate, 0.5 μg proteasome, 1.0 μg PA700 and are preincubated for 45 min. with 60 μM ATP.

These results suggest that the fraction contains a protein(s) that activates the proteasome and that this effect is dominant with respect to the action of known proteasome inhibitor in the same fraction.

Purification of a high molecular weight, ATP-dependent proteasome activator (PA700). In order to purify the proteasome activator, Fraction II proteins that precipitated in a solution of 38% saturated ammonium sulfate were subjected to a series of chromatographic procedures and the fractionated proteins were assayed for ATP-dependent activation of the 20S proteasome. Gel filtration chromatography of the extract on Sephacryl S-300 identified a single peak of such activity with an apparent molecular weight of 700,000. Because this molecular weight is very similar to that of the 20S proteasome, a number of control experiments were required to establish that the observed proteasome activity resulted from the activation of the exogenous proteasome by proteins in the column fractions. These controls included assays of column fractions in the absence of exogenous proteasome before and after preincubation. The endogenous proteasome activity of the column fractions was very low, and of that activity, all was accounted for by the 1,750,000-dalton protease. A very similar profile was observed when the assays included preincubation of the column fractions in the presence of ATP. The absence of detectable 20S proteasome in these fractions was confirmed by immunoblotting and by assay with exogenous PA28. These results are consistent with previous observations by us and others regarding the relative distribution of the 20S proteasome after ammonium sulfate fractionation of red cell lysates (i.e., that the 20S proteasome precipitates in solutions saturated to greater than 40% with respect to ammonium sulfate). Furthermore, preincubation of the column fractions with ATP but without exogenous proteasome had no effect on detected proteasome activity. Thus, the observed proteasome activity appeared to result from the ATP-dependent activation of exogenous proteasome by a protein(s) present in the column fractions.

The fractions containing the proteasome activating activity were pooled and subjected to ion-exchange chromatography on DEAE-Fractogel (EM separations). The activator bound this resin and was eluted with a linear gradient of NaCl at a position corresponding to approximately 250 mM NaCl. The sharp, symmetrical peak of activity displayed the same functional characteristics as those described for the activity on the gel filtration column, i.e., there was no detectable proteasome activity or proteasome protein in the column fractions, and all detected activity resulted required activation of exogenous proteasome.

The fractions containing the activator were pooled and subjected to hydroxylapatite chromatography. The activator bound to the resin and was eluted with a linear gradient of phosphate. Most of the activity eluted at a position corresponding to approximately 75 mM phosphate. A second, smaller peak of activity was identified at a position corresponding to approximately 110 mM phosphate. The activities have been termed Peak I and Peak II in order of their elution from the hydroxylapatite column. Peak I and Peak II were concentrated and subjected to gel filtration column chromatography on Sephacryl S400. Each peak eluted at a position corresponding to an apparent molecular weight of 700,000. The elution positions were not significantly different from one another, and the corresponding estimate of molecular weight was indistinguishable from that estimated by Sephacryl S-300 at the beginning of the preparation.

Non-denaturing PAGE of the Peak I and Peak II revealed a single major band for each with mobilities indistinguishable from one another. SDS-PAGE of the two activator proteins indicated that each was composed of approximately 15 peptides. With the exception of several minor proteins considered to be contaminants, the protein composition of Peak I and Peak II was remarkably similar. These included proteins with molecular weights of 100,000, 90,000, 60,000, and 50,000, about nine closely separated bands between 48,000 and 30,000, and several proteins with molecular weights between 25,000 and 30,000. Different preparations of the proteasome activators often contained very low levels of proteins that represent minor contaminants. These proteins did not comigrate with activity and were not consistently observed in all activator preparations.

Several studies indicated that these peptides were components of a single protein complex. First, they comigrated through a variety of chromatographic procedures. Second, when the protein band was excised from the non-denaturing gel and electrophoresed into SDS-PAGE the same characteristic proteins were observed. The structural and biochemical differences between the two forms is unclear. Most of the characterization studies described below have been conducted for each peak and there were no significant differences. For clarity the data are presented for Peak I. This activator has been termed PA700 (for proteasome activator with a molecular weight of 700,000).

When the samples were probed with antibodies against the proteasome and PA28, no detectable cross-reactivity was detected. This is consistent with biochemical data presented below that the activation is distinct from PA28.

Characterization of PA700. Proteasome activation by the purified PA700 was dependent on preincubation of both proteins in the presence of ATP and $Mg^{2+}$. Preincubation of either protein alone (with or without ATP and $Mg^{2+}$) did not result in subsequent proteasome activation when the two proteins were then combined for the hydrolytic assay. PA700 alone had no detectable proteolytic activity in these assays either before or after preincubation. Maximal proteasome activation was achieved after 60 min of preincubation and ranged from 15–100 fold; variation in the calculated stimulation resulted from variations in the low proteasome activities measured in the unactivated samples. The activity of the PA700-activated proteasome was very consistent from experiment to experiment. After preincubation with PA700 and ATP, maximal rates of activated proteasome activity were observed immediately in the incubation.

Proteasome activation depended on the PA700 concentration in the preincubation, and half-maximal levels of activation were achieved at molar ratios of 3:1 (PA700:proteasome).

Maximal proteasome activation by PA700 was achieved at approximately 60 μM ATP. Of the other nucleotide triphosphates tested only CTP could also activate the proteasome, but this required 100-fold higher concentrations. Proteasome activation by ATP appeared to require ATP hydrolysis because a variety of non-hydrolyzable ATP analogs failed to promote activation. Neither ADP, AMP, adenosine, nor $PP_i$ promoted proteasome activation.

The proteasome is a multicatalytic protease, whose various activities can be independently regulated. The effect of PA700 was assessed with other peptide substrates specific for distinct catalytic sites on the protease. PA700 stimulated the hydrolysis of all of these substrates although the degree of stimulation was less than that observed for Suc-Leu-Leu-Val-Tyr-AMC. Interestingly, the hydrolysis of large protein substrates such as casein and lysozyme was not stimulated by PA700. In this regard it regulated the activities of the proteasome similarly to PA28.

Complex formation. In order to examine possible mechanisms by which PA700 affected proteasome activity, the activation solution was subjected to gel filtration column chromatography or velocity sedimentation centrifugation. In each case an activated form of the proteasome was isolated and was characterized by an apparent molecular weight that was much larger than that of the purified proteasome. These results indicate that the proteasome and PA700 formed a complex and that the complex was characterized by increased proteasome activity. The size of the complex was similar to that observed for the 1,750,000-dalton proteasome identified in crude red cell extracts. The activated proteasome isolated in these experiments also functioned as such in the absence of additional ATP. Addition of ATP to the assay produced no additional increase in proteasome activity. These results suggest that the ATP functions by a mechanism that results in increased hydrolytic activity of the proteasome but is not continuously required to maintain this activation for the hydrolysis of peptide substrates.

In order to investigate the biochemical mechanism of proteasome activation by PA700, the activated protein was subjected to velocity sedimentation centrifugation and to gel filtration chromatography. An activated proteasome was identified, suggesting that the activator and the proteasome formed a complex which was stable under the separation conditions. The size of the complex was indistinguishable from the proteasome isolated from crude, unfractionated cell extracts. Similar results were obtained when the complex was isolated by gel filtration chromatography and after non-denaturing PAGE. No complex was identified when the proteasome and PA700 were preincubated in the absence of ATP. These results indicated that activation and complex formation are closely linked.

In order to examine the function of ATP in the regulation of the proteasome by PA700, PA700 was assayed for ATPase activity. The purified protein hydrolyzed ATP at a rate that did not increase when measured in the presence of the proteasome under the standard preincubation conditions.

EXAMPLE V

A Peptide Inhibitor of Proteasome Activation

An 18 amino acid peptide corresponding to the carboxylterminus of PA28 was synthesized.

Peptide Synthesis. Continuous-flow solid-phase peptide synthesis was performed on a 430 peptide syunthesizer from Applied Biosystems Inc. (Foster City, Calif.) using fluorenylmethoxycarbonyl (Fmoc) protected amno acids with N-methylpyrrolidone as a solvent system and 1-hydroxybenzotriazole (HOBT)/2-(1-benzotriazol-1-, 1,3,3-tetramethyluronium hexafluorophosphate (HBTU) activation of the amino acids. Amino acid side-chain protections were selected to be removable during trifluoroacetic acid (TFA) cleavage. P-hydroxymethylphenoxymethyl polystyrene resin was used as a solid support.

Figure 26:
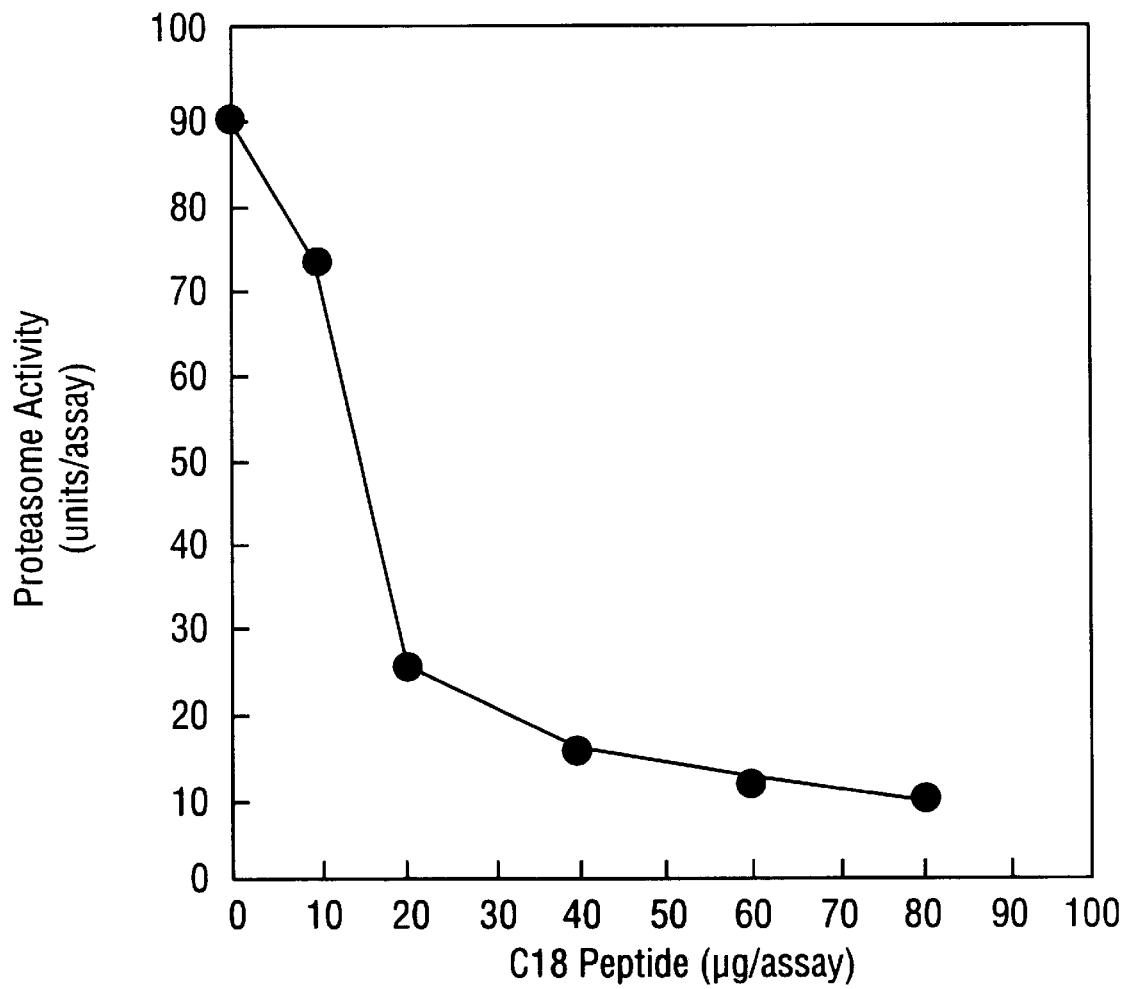
FIG. 26 shows the inhibition of PA28-activated proteasome by C18, an 18 amino acid peptide corresponding to the carboxyterminal 18 amino acids of PA28. Proteasome activity in the absence of PA28 was 1.2 units/assays. Assays contained 0.5 μg of proteasome and 1 μg of PA28. A control peptide containing 18 amino acids of similar composition, but different sequence, had no effect on proteasome activity.
Figure 27:
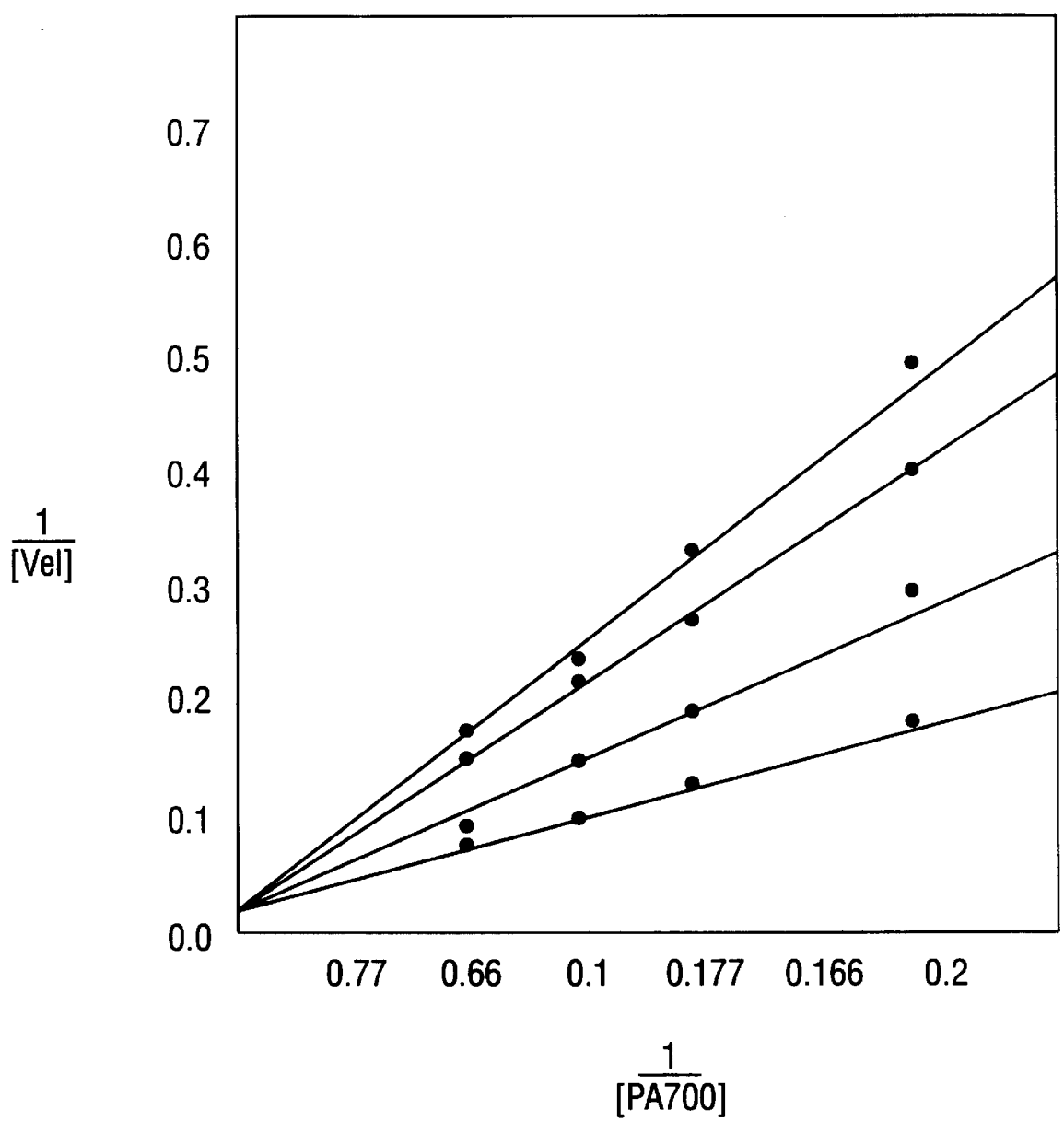
FIG. 27 shows that the C18 peptide competitively inhibits activation of the proteasome by PA700. Activation of the proteasome by PA700 was performed in the presence of the indicated concentrations of purified C18 peptide. The data demonstrate that C18 competitively inhibits proteasome activation by PA700. C18, alone, had no effect on baseline proteasome activity.

This peptide does not activate the proteasome, but does bind to it. It competitively inhibits binding and activation of PA28 (FIG. 26). It also competitively inhibits the binding and activation of proteasome activator, PA700 (FIG. 27). Therefore, this peptide or a compound with similar properties may be used to block the action of the proteasome in intact cells. Such a compound or analogs having similar binding activity may be used to control accelerated rates of intracellular protein degradation. The peptide has the sequence: Acetyl-KNFEKLKKPRGETKGMIY (SEQ ID NO. 3). The N-terminal lysine may be acetylated if needed for stability. The dipeptide Ile-Tyr by itself has very weak activity, however, if the C-terminal Ile-Tyr is removed from the 18 amino acid peptide, the resultant 16-mer did not measurably bind to the proteasome. Therefore, the C-terminal Ile-Tyr amino acids or their functional equivalents appear to be important for binding of the 18-mer to the proteasome and for inhibition of the activation of the proteasome by activating factors PA28 and PA700. An equivalent of the 18-mer may comprise less than 18 amino acids or may comprise functionally equivalent amino acid replacements which allow similar binding activity.

EXAMPLE VI

Synergistic Activation of Proteasome Hydrolysis of Large Protein Substrates by PA28, PA700, ATP and $Mg^{++}$ Surprisingly, the 20S proteasome has been observed to degrade large protein substrates such as casein, especially ubiquinated casein, for example, in the presence of PA28, PA700, ATP and $Mg^{++}$. This synergistic activator alters the substrate specificity of the proteasome to hydrolyze large protein substrates rather than peptide substrates.

The following references are incorporated in pertinent part by reference herein for the reasons cited above.

REFERENCES

1. Rivett, A. J., (1989) *Arch. Biochem. Biophys.* 268:1–8.
2. Orlowski, M. (1990) *Biochemistry* 29:10289–10297.
3. Wilk, S., and Orlowski, M. (1983) *J. Neurochem.* 40:842–849.
4. Dahlmann, B. et al., (1985) *Biochem. J.* 228: 171–177.
5. McGuire, M. J., and DeMartino, G. N. (1986) *Biochem. Biophys. Acta* 873:279–289.
6. Lee, L. W. et al., (1990) *Biochem. Biophys. Acta.* 1037:178–185.
7. DeMartino, G. N. et al., (1991) *Biochem Biophys. Acta.* 1079:29–38.
8. Fujiwara, T. et al., (1989) *Biochemistry* 28:7332–7340.
9. Sorimachi, H. et al., (1990) *Eur. J. Biochem.* 193:775–781.
10. Tamura, T. et al., (1990) *FEBS Lett.* 264:91–94.
11. Tanaka, K. et al., (1990) *Biochem. Biophys. Res. Commun.* 171:676–683.
12. Haass, C. et al., (1989) *EMBO J.* 8:2373–2379.
13. Haass, C. et al., (1990) *Gene (Amst.)* 90:235–241.
14. Haass, C. et al., (1990) *Nucleic Acids Res.* 18:4018.
15. Fujiwara, T. et al., (1990) *J. Biol. Chem.* 265:16604–16613.
16. Heinemeyer et al., (1991) *EMBO J.*, 10:555–562.
16. McGuire, M. J. et al.,(1988) *Arch. Biochem. Biophys.* 262:272–285.
18. McGuire, M. J. et al., (1989) *Biochim. Biophys. Acta* 967:195–203.
19. McGuire, M. J. and DeMartino, G. N. (1989) Biochem. Biophys.

Res. Commun. 160:911–916.
20. DeMartino, G. N. et al., (1991) *Biochim. Biophys. Acta* 1073:299–308.
21. McGuire, M. J. et al., (1989) *Biochim. Biophys. Acta* 995:181–186.
22. Tanaka, K. et al., (1986) *J. Biol. Chem.* 261:15197–15203.
23. Driscoll, J. and Goldberg, A. L., (1989) *Proc. Natl. Acad. Sci., U.S.A.* 86:787–791.
24. Hough, R. et al., (1987) *J. Biol. Chem.* 262:8303–8313.
25. Waxman, L. et al., (1987) *J. Biol. Chem.* 262:2451–2457.
26. Eytan, E. et al., (1989) *Proc. Natl. Acad. Sci. U.S.A.* 86:7751–7755.
27. Ma, C. P. et al., (1992) *Biochim. Biophys. Acta* 1119:303–311.
28. Bradford, M. M. (1976) *Anal. Biochem.* 7:248–254.
29. Orlowski, M and Michaud, C., (1989) *Biochemistry* 28:9270–9278.
30. Orlowski M. et al., (1991) *Biochemistry* 30:5999–6005.
31. Arribas J. and Castano, J. C., (1990) *J. Biol. Chem.* 265:13969–13973.
32. Dick, L. R. et al., (1991) *Biochemistry* 30:2725–2734.
33. Shanklin, J. et al., (1987) *Proc. Natl. Acad. Sci. U.S.A.* 84:359.
34. Hershko, A. et al., (1991) *J. Biol. Chem.* 266:16376–16379.
35. Ciechanover, A. et al., (1986) *Cell* 37:57–66.
36. Glynne, R. et al., (1991) *Nature* 353:357–360.
37. Ortiz-Navarrete, V. et al., (1991) *Nature* 353:662–664.
38. Martinez, C. K. and Monaco, J. J., (1991) *Nature* 353:664–667.
39. Rivett, A. J. (1985) *J. Biol. Chem.* 260:12600–12606.
40. Yu, B. et al., (1991) *J. Biol. Chem.* 266:17396–17400.
41. Tanaka, K. et al., (1992) *New Biologist* 4:173–187.
42. Goldberg, A. L., (1992), *Eur. J. Biochem.* 205:9–23.
43. Gottesman S. and Maurizi, M. R., (1992) *Micro. Rev.* 56:592–621.
44. Hershko, A. and Ciechanover, A., (1992) *Ann. Rev. Biochem.* 61:761–807.
45. Goldberg, A. L. and Rock, K. L., (1992), *Nature* 357:375–379.
46. Dubiel, W. et al., (1992) *J. Biol. Chem.* 267:22369–22377.
47. Li, X. S. et al., (1991) *Biochemistry* 30:9709–9715.
48. Driscoll J. and Goldberg, A. L. (1990), *J. Biol. Chem.* 265:4789–4792.
49. McDonald, J. K. and Schwabe, C., (1977) IN *Proteinases in mammalian cell and tissues* (Barrett, A. J., ed) North-Holland Publishing Co., Amsterdam, pp. 311–391.
50. Ninjoor, V. et al., (1974) *Biochim. Biophys. Acta* 370:308–321.
51. McDonald, J. K. and Ellis, S., (1975) *Life Sci.* 17:1269–1276.
52. Otto, K. and Riesenkonig, H., (1975) *Biochim Biophys. Acta* 379:462–475.
53. Afroz, H. et al., (1976) *Biochim Biophys Acta* 452:503–509.
54. Lones, M. et al., (1983) *Arch Biochem. Biophys.* 221:64–78.
55. Lipperheide, C. and Otto, K., (1986) *Biochim. Biophys. Acta* 880:171–178.
56. Li, X. S. and Etlinger, J. D., (1992) *Biochemistry* 31:11963–11967.
57. Hershko, A., and Ciechanover, A. (1982) *Ann. Rev. Biochem.* 51:335–364.
58. Yukawa et al., (1991) *Biochem. Biophys. Res. Commun.* 178(1):256–262.
59. Vinitsky et al., (1992) *Biochemistry* 31:9421–9428.
60. Driscoll et al., (1992) *Proc. Natl. Acad. Sci. USA* 89:4986–4990.

It is understood that the examples and embodiments described herein are for illustrative purposes only and that various modifications in light thereof will be suggested to persons skilled in the art and are to be included within the spirit and purview of this application and scope of the appended claims.

---

What is claimed is:

1. A proteasome activating factor, comprising the amino acid sequence of SEO ID NO:2, separated from proteasome, which activates hydrolysis by proteasomes of substrates comprising Z-Arg-Arg-AMC.

2. The factor of claim 1 defined further as eluting from a DEAE ion-exchange column at a sodium chloride concentration of about 100 mM.

3. The factor of claim 1 wherein the activation is ATP-independent.

4. A purified ATP-independent proteasome activating factor separated from proteasome, wherein said proteasome activating factor:
   a) has a subunit molecular weight of about 28,000 daltons and a native molecular weight of about 180,000 daltons;
   b) precipitates in a 40–85% ammonium sulfate fraction;
   c) elutes from a DEAE ion-exchange column at a sodium chloride concentration of about 100 mM; and
   d) has activating activity for proteasome hydrolysis of trypsin-like, chymotrypsin-like and peptidylglutamyl-like substrates.

5. The proteasome activating factor of claim 4 defined further as consisting of the amino acid sequence of FIG. 16.

6. A purified ATP-dependent proteasome activating factor, separated from proteasome, wherein said proteasome activating factor:
   a) has a native molecular weight of about 700,000 daltons;
   b) precipitates in a 0–38% ammonium sulfate fraction;
   c) elutes from a DEAE ion-exchange column at a sodium chloride concentration of about 250 mM; and
   d) has activating activity for proteasome hydrolysis of trypsin-like, chymotrypsin-like and peptidylglutamyl-like substrates.

7. The ATP-dependent proteasome activating factor of claim 6, wherein said factor is purified from red blood cells.

8. The ATP-dependent proteasome activating factor of claim 7, wherein said red blood cells are bovine red blood cells.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 720 base pairs
        ( B ) TYPE: nucleic acid
        ( C ) STRANDEDNESS: double
        ( D ) TOPOLOGY: linear ( i i ) MOLECULE TYPE: genomic DNA ( x i ) SEQUENCE DESCRIPTION: SEQ ID NO:1:

```
GGAATTCCGA  CATCCCAGTG  CCTGATCCAG  TCAAGGAGAA  AGAGAAGGAG        50

GAGCGGAGGA  AACAGCAGGA  GAAGGAAGAC  AAGGATGAAA  AGAAGAAAGG       100

GGAAGATAAG  GACAAAGGTC  CTCCATGTGG  CCCAGTGAGC  TGCAATGAGA       150

AGATTGTGGT  CCTCCTGCAG  CGGGTAAAGC  CTGAGATCAA  GGATGTCATT       200

GAGAAGCTCA  ACCTGGTCAC  CACCTGGCTG  CAGCTGCAAA  TACCTCGGAT       250
```

|  |  |  |  |  |
|---|---|---|---|---|
| TGAGGATGGG | AATAATTTTG | GAGTGGCTGT | CCAGGAGAAG | GTGTTTGAGC | 300 |
| TGATGACTGC | TCTTCACACC | AAGCTGGAAG | GCTTCCACAC | TCAAATTTCC | 350 |
| AAGTATTTCT | CTGAGCGCGG | TGATGCTGTA | ACCAAAGCAG | CCAAGCAGCC | 400 |
| CCATGTGGGT | GATTATCGGC | AACTGGTACA | CGAGCTGGAT | GAGGCAGAGT | 450 |
| ACCGGGATAT | CCGGCTGATG | GTCATGGAGA | TCGCAACGTA | CGCTGTGTTA | 500 |
| TATGACATCA | TCCTGAAGAA | CTTCGAGAAG | CTCAAGAAGC | CAGGGGAGA | 550 |
| AACAAAGGGA | ATGATCTATT | GAGACCCTCC | TCTCATTCTG | TGATGGCTCC | 600 |
| AACAGAGACC | TTCTGACTTT | TACAGGGGAC | TCCAGACTTT | CCCCACCTTC | 650 |
| TGCCTGTTGG | TTTCTCCCTC | ACCTTACCTC | CCAGGCACAA | TAAATATAGT | 700 |
| CATACCATTG | CCAAAAAAAA |  |  |  | 720 |

(2) INFORMATION FOR SEQ ID NO:2:

(i) SEQUENCE CHARACTERISTICS:
       (A) LENGTH: 189 amino acid residues
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:2:

```
Asn Ser Asp Ile Pro Val Pro Asp Pro Val Lys Glu Lys Glu Lys Glu
 1               5                  10                  15
Glu Arg Arg Lys Gln Gln Glu Lys Glu Asp Lys Asp Glu Lys Lys Lys
             20                  25                  30
Gly Glu Asp Glu Asp Lys Gly Pro Pro Cys Gly Pro Val Ser Cys Asn
         35                  40                  45
Glu Lys Ile Val Val Leu Leu Gln Arg Val Lys Pro Glu Ile Lys Asp
     50                  55                  60
Val Ile Glu Lys Leu Asn Leu Val Thr Thr Trp Leu Gln Leu Gln Ile
 65                  70                  75                  80
Pro Arg Ile Glu Asp Gly Asn Asn Phe Gly Val Ala Val Gln Glu Lys
                 85                  90                  95
Val Phe Glu Leu Met Thr Ala Leu His Thr Lys Leu Glu Gly Phe His
                100                 105                 110
Thr Gln Ile Ser Lys Tyr Phe Ser Glu Arg Gly Asp Ala Val Thr Lys
            115                 120                 125
Ala Ala Lys Gln Pro His Val Gly Asp Tyr Arg Gln Leu Val His Glu
        130                 135                 140
Leu Asp Glu Ala Glu Tyr Arg Asp Ile Arg Leu Met Val Met Glu Ile
145                 150                 155                 160
Ala Thr Tyr Ala Val Leu Tyr Asp Ile Ile Leu Lys Asn Phe Glu Lys
                165                 170                 175
Leu Lys Lys Pro Arg Gly Glu Thr Lys Gly Met Ile Tyr
                180                 185
```

(2) INFORMATION FOR SEQ ID NO:3:

(i) SEQUENCE CHARACTERISTICS:
       (A) LENGTH: 18 amino acid residues
       (B) TYPE: amino acid
       (C) STRANDEDNESS: single
       (D) TOPOLOGY: linear (ii) MOLECULE TYPE: peptide ( x i ) SEQUENCE DESCRIPTION: SEQ ID NO:3:

```
Lys Asn Phe Glu Lys Leu Lys Lys Pro Arg Gly Glu Thr Lys Gly Met
 1           5                   10                  15
Ile Tyr
```